(12) United States Patent
Hasegawa et al.

(10) Patent No.: US 7,981,589 B2
(45) Date of Patent: Jul. 19, 2011

(54) FLUORINATED MONOMER, FLUORINATED POLYMER, RESIST COMPOSITION AND PATTERNING PROCESS

(75) Inventors: Koji Hasegawa, Joetsu (JP); Takeshi Kinsho, Joetsu (JP); Katsuhiro Kobayashi, Joetsu (JP); Tsunehiro Nishi, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 377 days.

(21) Appl. No.: 12/146,375

(22) Filed: Jun. 25, 2008

(65) Prior Publication Data

US 2009/0035699 A1 Feb. 5, 2009

(30) Foreign Application Priority Data

Jul. 30, 2007 (JP) ................................ 2007-196907

(51) Int. Cl.
 *G03F 7/004* (2006.01)
 *C08F 32/04* (2006.01)
 *C08F 32/08* (2006.01)
(52) U.S. Cl. .................. 430/270.1; 430/907; 430/910; 526/247; 526/281
(58) Field of Classification Search ........... 430/270.1, 430/907, 910; 526/247, 281
See application file for complete search history.

(56) References Cited

U.S. PATENT DOCUMENTS

| 5,714,625 | A | 2/1998 | Hada et al. | |
| 6,004,724 | A | 12/1999 | Yamato et al. | |
| 6,063,953 | A | 5/2000 | Hada et al. | |
| 6,261,738 | B1 | 7/2001 | Asakura et al. | |
| 6,312,867 | B1 | 11/2001 | Kinsho et al. | |
| 6,512,020 | B1 | 1/2003 | Asakura et al. | |
| 6,686,123 | B2 * | 2/2004 | Lee et al. | 430/270.1 |
| 6,800,418 | B2 | 10/2004 | Yoon et al. | |
| 6,830,866 | B2 | 12/2004 | Kobayashi et al. | |
| 6,916,591 | B2 | 7/2005 | Ohsawa et al. | |
| 6,964,840 | B2 | 11/2005 | Nishimura et al. | |
| 7,094,850 | B2 | 8/2006 | Miyazawa et al. | |
| 2004/0142279 | A1 * | 7/2004 | Bok et al. | 430/271.1 |
| 2006/0246377 | A1 | 11/2006 | Yamato et al. | |
| 2007/0179309 | A1 | 8/2007 | Hasegawa et al. | |
| 2007/0231741 | A1 * | 10/2007 | Nishi et al. | 430/270.1 |
| 2009/0202943 | A1 * | 8/2009 | Ohsawa et al. | 430/285.1 |

FOREIGN PATENT DOCUMENTS

| JP | 9-95479 | A | 4/1997 |
| JP | 9-208554 | A | 8/1997 |
| JP | 9-230588 | A | 9/1997 |
| JP | 9-301948 | A | 11/1997 |
| JP | 2906999 | B2 | 4/1999 |
| JP | 2000-314956 | A | 11/2000 |
| JP | 2000-336121 | A | 12/2000 |
| JP | 2002-72484 | A | 3/2002 |
| JP | 2003-40840 | A | 2/2003 |
| JP | 2003-66612 | A | 3/2003 |
| JP | 2003-192729 | A | 7/2003 |
| JP | 2006-22319 | A | 1/2006 |
| WO | WO-2004/074242 | A2 | 9/2004 |

OTHER PUBLICATIONS

Wallraff et al., "Active Fluororesists for 157nm Lithograohy: IBM's Favorite Platforms", 2nd International Symposium on 157nm Lithography, (May 14-17, 2001).
Lin., Semiconductor Foundry, Lithography, and Partners, Micropatterning Division, TSMC, Inc. ,Proc. SPIE vol. 4690, xxix.
Owa et al., "Immersion lithography; its potential performance and issues", Proc. SPIE vol. 5040, p. 724.
Hirayama, "Resist and Cover Material Investigation for Immersion Lithography" 2nd Immersion Workshop, Jul. 11, 2003.
Kanna et al., "Study and Control of the Interfacial Mass Transfer of Resist Components in 193nm Immerison Lithography", Journal of Photopolymer Science and Technology, vol. 18, No. 5, (2005), pp. 603-613.
Journal of Photopolymer Science and Technology, vol. 8 No. 1; (1995), pp. 43-46.
Arimitsu et al., "Effect of Phenolic Hydroxyl Residues on the Improvement of Acid-Proliferation-Type Photoimaging Materials", Journal of Photopolymer Science and Technology, vol. 9 No. 1 (1996); pp. 29-30.

* cited by examiner

*Primary Examiner* — John S Chu
(74) *Attorney, Agent, or Firm* — Birch, Stewart, Kolasch & Birch, LLP

(57) ABSTRACT

Fluorinated monomers of formula (1) are useful in producing polymers for the formulation of radiation-sensitive resist compositions. $R^1$ is H or monovalent $C_1$-$C_{20}$ hydrocarbon group, $R^2$ is H, F, methyl or trifluoromethyl, $R^3$ and $R^4$ are H or a monovalent $C_1$-$C_8$ hydrocarbon group, or $R^3$ and $R^4$ may form an aliphatic hydrocarbon ring, and A is a divalent $C_1$-$C_6$ hydrocarbon group (1)

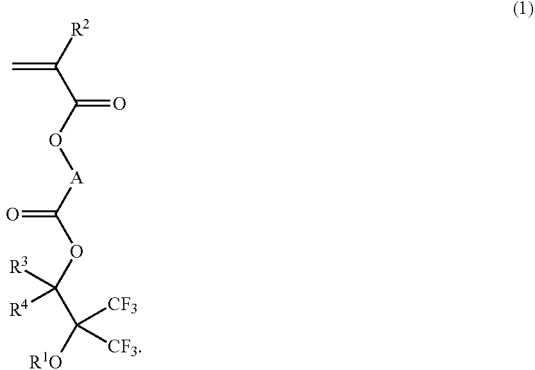

5 Claims, No Drawings

FLUORINATED MONOMER, FLUORINATED POLYMER, RESIST COMPOSITION AND PATTERNING PROCESS

CROSS-REFERENCE TO RELATED APPLICATION

This non-provisional application claims priority under 35 U.S.C. §119(a) on Patent Application No. 2007-196907 filed in Japan on Jul. 30, 2007, the entire contents of which are hereby incorporated by reference.

TECHNICAL FIELD

This invention relates to fluorinated monomers (or polymerizable fluorinated compounds) which are useful as raw materials for the synthesis of functional materials, pharmaceutical and agricultural chemicals, and particularly in producing polymers for use in the manufacture of radiation-sensitive resist compositions which are fully transparent to radiation having a wavelength of up to 500 nm, especially up to 300 nm, typically KrF, ArF or $F_2$ laser, and have good development characteristics.

The invention also relates to polymers comprising recurring units derived from the fluorinated monomers, photoresist compositions comprising the polymers, and a patterning process using the photoresist compositions.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 µm or less. Various alkali-soluble resins are used as the base resin in such resists.

For KrF laser resists, a polyhydroxystyrene resin having phenolic hydroxyl groups as the alkali-soluble functional group is, in fact, a standard base resin. For ArF laser resists, poly(meth)acrylate resins using carboxyl groups as the alkali-soluble group and resins comprising polymerized units of cycloaliphatic olefin such as norbornene are under investigation. Of these, the poly(meth)acrylate resins are regarded, due to ease of polymerization, as a promising candidate that will find practical use. For these resist resins using as the alkali-soluble functional group carboxyl groups having a higher acidity than phenolic hydroxyl groups, however, an outstanding issue is difficulty of dissolution control, often leading to pattern collapse caused by swelling or the like.

Functional groups having an acidity comparable to phenolic hydroxyl groups are desired. It was proposed to use an alcohol having a plurality of fluorine atoms substituted at α- and α'-positions (e.g., having a partial structure: —$C(CF_3)_2$OH) as the alkali-soluble functional group, as described in G. Wallraff et al., Active Fluororesists for 157 nm lithography in 2nd International Symposium on 157 nm Lithography. Styrene and norbornene derivatives having fluoroalcohol —$C(CF_3)_2$OH incorporated therein are proposed as monomers used in the manufacture of base resins. Similar examples of fluoroalcohol-substituted norbornene are found in JP-A 2003-192729 and JP-A 2002-72484. For the polymerization of norbornene monomers, however, radical polymerization of monomers of the same type is difficult, and instead, special polymerization techniques such as coordinate polymerization using unique transition metal catalysts and ring-opening metathesis polymerization are necessary. Although alternating copolymerization between a norbornene monomer and a comonomer such as maleic anhydride or maleimide can be implemented by radical polymerization, the presence of comonomer imposes a substantial limit on the freedom of resin design.

JP-A 2003-040840 describes fluoroalcohol-substituted acrylate monomers. Although the method of preparing these monomers is not definite, the starting reactant used is hexafluoroacetone (boiling point −27° C.) which is awkward to handle because it is gaseous at room temperature. The synthesis of polymerizable compound must follow many steps, leaving the problems of an increased cost and difficult commercial implementation.

There is a strong demand to develop a polymerizable compound (or monomer) having both a polymerizable unsaturated group such as a (meth)acrylate structure and a functional group having an acidity comparable to phenolic hydroxyl, which compound can be prepared and polymerized both in an industrially acceptable and economic manner.

Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the postponement of $F_2$ lithography and the early introduction of ArF immersion lithography were advocated (see Proc. SPIE Vol. 4690 xxix).

In the ArF immersion lithography, the space between the projection lens and the wafer is filled with water. Since water has a refractive index of 1.44 at 193 nm, pattern formation is possible even using a lens with NA of 1.0 or greater. Theoretically, it is possible to increase the NA to 1.44. The resolution is improved by an increment of NA. A combination of a lens having NA of at least 1.2 with ultra-high resolution technology suggests a way to the 45-nm node (see Proc. SPIE Vol. 5040, p 724).

Several problems associated with the presence of water on resist were pointed out. For example, projection lens contamination and pattern profile changes occur because the acid once generated from a photoacid generator and the amine compound added to the resist as a quencher can be dissolved in water. Inversely, swelling and circular defects known as water marks occur because water can penetrate into the resist film. For overcoming these problems, it was proposed to provide a protective coating between the resist and water (see the 2nd Immersion Workshop, Jul. 11, 2003, Resist and Cover Material Investigation for Immersion Lithography); and to prevent resist materials from dissolution in water or water penetration by controlling the water repellency of resist materials, typically photoacid generators (PAG) or base resins (see J. Photopolymer Sci. and Technol., Vol. 18, No. 5, p 603 (2005)).

DISCLOSURE OF THE INVENTION

An object of the present invention is to provide fluorinated monomers which are useful for the preparation of polymers to be formulated in resist compositions, the resist compositions exhibiting a high resolution and preventing dissolution in immersion media and penetration of immersion media when processed by photolithography using high-energy radiation such as ArF excimer laser radiation as a light source, especially immersion lithography; polymers obtained from the fluorinated monomers; resist compositions comprising the polymers as a base resin; and a patterning process using the resist compositions.

The inventor has found that a fluorinated monomer of the general formula (1) shown below can be readily prepared, and that a resist composition comprising a polymer derived from the fluorinated monomer as a base resin exhibits a high resolution and an anti-swelling effect, and prevents dissolution in water as an immersion medium and penetration of water when processed by photolithography, especially immersion lithography so that the polymer is advantageously used in resist form for precise micropatterning.

Accordingly, the present invention provides a fluorinated monomer, polymer, resist composition, and patterning process, as defined below.

A first embodiment of the invention relates to a fluorinated monomer having the general formula (1).

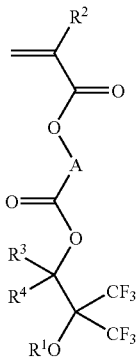

(1)

Herein $R^1$ is hydrogen or a straight, branched or cyclic monovalent hydrocarbon group of 1 to 20 carbon atoms in which any constituent —$CH_2$— moiety may be replaced by —O— or —C(=O)—, $R^2$ is hydrogen, fluorine, methyl or trifluoromethyl, $R^3$ and $R^4$ are each independently hydrogen or a straight, branched or cyclic monovalent hydrocarbon group of 1 to 8 carbon atoms, or $R^3$ and $R^4$ may bond together to form an aliphatic hydrocarbon ring with the carbon atom to which they are attached, and A is a straight, branched or cyclic divalent hydrocarbon group of 1 to 6 carbon atoms.

A second embodiment of the invention relates to a fluorinated monomer having the general formula (2).

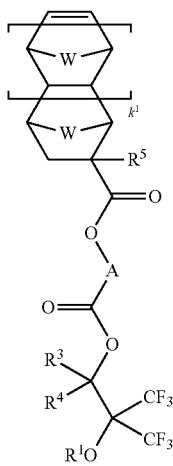

(2)

Herein $R^1$, $R^3$, $R^4$ and A are as defined above, $R^5$ is hydrogen, fluorine, methyl or trifluoromethyl, W is —$CH_2$— or —O—, and $k^1$ is 0 or 1.

A third embodiment of the invention relates to a polymer comprising recurring units derived from the fluorinated monomer of the first or second embodiment, and more specifically, a polymer comprising recurring units having any one of the general formulas (1a) to (1c).

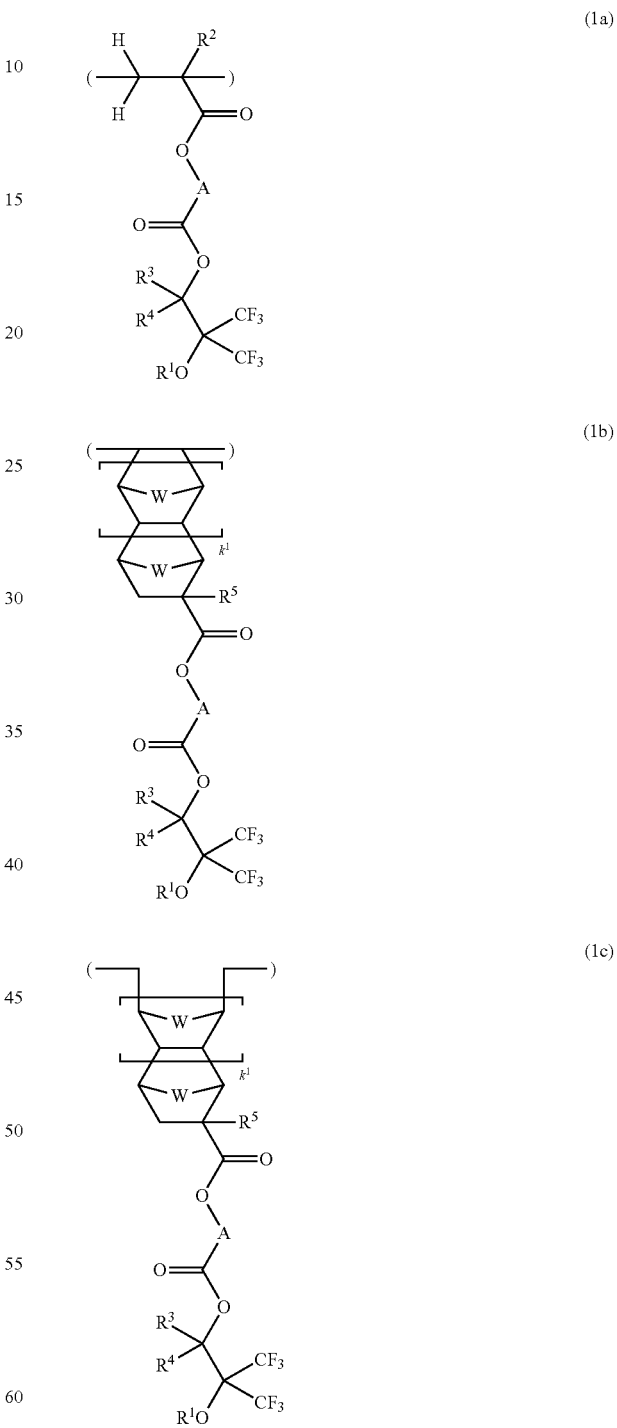

Herein $R^1$ to $R^5$, A, W and $k^1$ are as defined above.

In a preferred embodiment, the polymer may further comprise recurring units of at least one type selected from the general formulas (3) to (6).

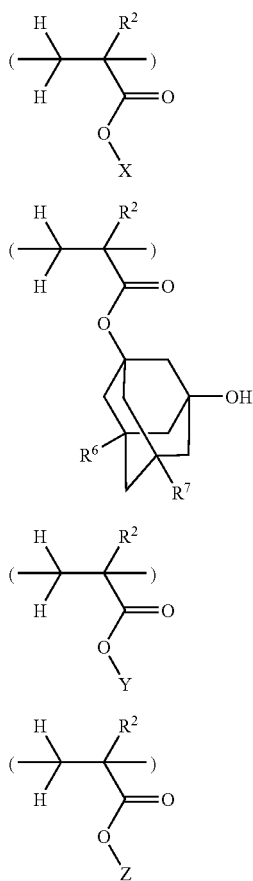

Herein $R^2$ is as defined above, $R^6$ and $R^7$ are each independently hydrogen or hydroxyl, X is an acid labile group, Y is a substituent group having a lactone structure, and Z is hydrogen, a fluoroalkyl group of 1 to 15 carbon atoms or a fluoroalcohol-containing substituent group of 1 to 15 carbon atoms.

A fourth embodiment of the invention relates to a resist composition comprising the polymer defined above as a base resin.

A fifth embodiment of the invention relates to a pattern forming process comprising the steps of applying the resist composition defined above onto a substrate to form a coating; heat treating the coating and exposing it to high-energy radiation or electron beam through a photomask; optionally heat treating the exposed coating, and developing it with a developer. In a preferred embodiment, the exposing step is immersion lithography with a liquid having a high refractive index of at least 1.0 interposed between the resist coating and a projection lens. In another preferred embodiment, the process further comprising the step of applying a protective coating on the resist coating, and the exposing step is immersion lithography with a liquid having a high refractive index of at least 1.0 interposed between the protective coating and a projection lens.

BENEFITS OF THE INVENTION

The fluorinated monomers of the invention are useful as raw materials for the synthesis of polymers, functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, and exhibit good development characteristics. Radiation-sensitive resist compositions comprising the polymers as base resin exhibit high resolution and an anti-swelling effect, and prevent dissolution in water as an immersion medium and penetration of water when processed by photolithography, especially immersion lithography. The polymers are advantageously used in resist form for precise micropatterning.

DESCRIPTION OF THE PREFERRED EMBODIMENTS

As used herein, the singular forms "a," "an" and "the" include plural referents unless the context clearly dictates otherwise. The notation (Cn-Cm) means a group containing from n to m carbon atoms per group. Me stands for methyl.

While a certain compound is herein represented by a chemical formula, many compounds have a chemical structure for which there can exist enantiomers or diastereomers. Unless otherwise stated each chemical formula collectively represents all such stereoisomers. Such stereoisomers may be used alone or in admixture.

Fluorinated Monomer

In a first embodiment of the invention, the fluorinated monomer has the general formula (1).

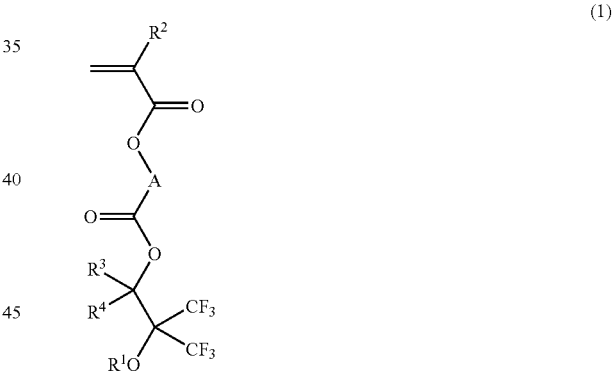

Herein $R^1$ is hydrogen or a straight, branched or cyclic monovalent hydrocarbon group of 1 to 20 carbon atoms in which any constituent —$CH_2$— moiety may be replaced by —O— or —C(=O)—, $R^2$ is a hydrogen atom, fluorine atom, methyl group or trifluoromethyl group, $R^3$ and $R^4$ are each independently hydrogen or a straight, branched or cyclic monovalent hydrocarbon group of 1 to 8 carbon atoms, or $R^3$ and $R^4$ may bond together to form an aliphatic hydrocarbon ring with the carbon atom to which they are attached, and A is a straight, branched or cyclic divalent hydrocarbon group of 1 to 6 carbon atoms.

The monovalent hydrocarbon groups represented by $R^1$ include a variety of protective groups for alcoholic hydroxyl groups. Suitable hydrocarbon groups include groups of the following general formulae (R1-1) and (R1-2), tertiary alkyl groups of 4 to 15 carbon atoms, trialkylsilyl groups in which each alkyl moiety has 1 to 5 carbon atoms, oxoalkyl groups of 4 to 15 carbon atoms, and acyl groups of 1 to 10 carbon atoms.

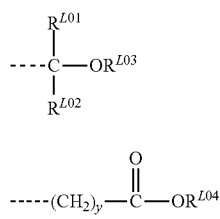

(R1-1)

(R1-2)

In these formulae and throughout the specification, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

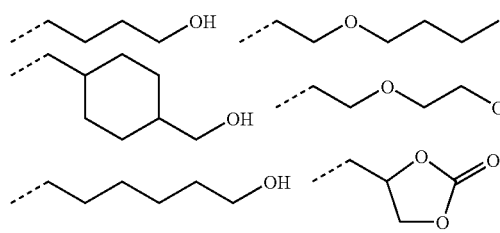

A pair of $R^{L01}$ and $R^{L02}$, $R^{L01}$ and $R^{L03}$, or $R^{L02}$ and $R^{L03}$ may bond together to form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (R1-1).

Examples of suitable tertiary alkyl groups represented by $R^1$ or $R^{L04}$ include tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Exemplary acyl groups include formyl, acetyl, ethylcarbonyl, pivaloyl, methoxycarbonyl, ethoxycarbonyl, tert-butoxycarbonyl, trifluoroacetyl, and trichloroacetyl. Letter y is an integer of 0 to 6.

Of the protective groups of formula (R1-1), the straight and branched ones are exemplified by the following groups.

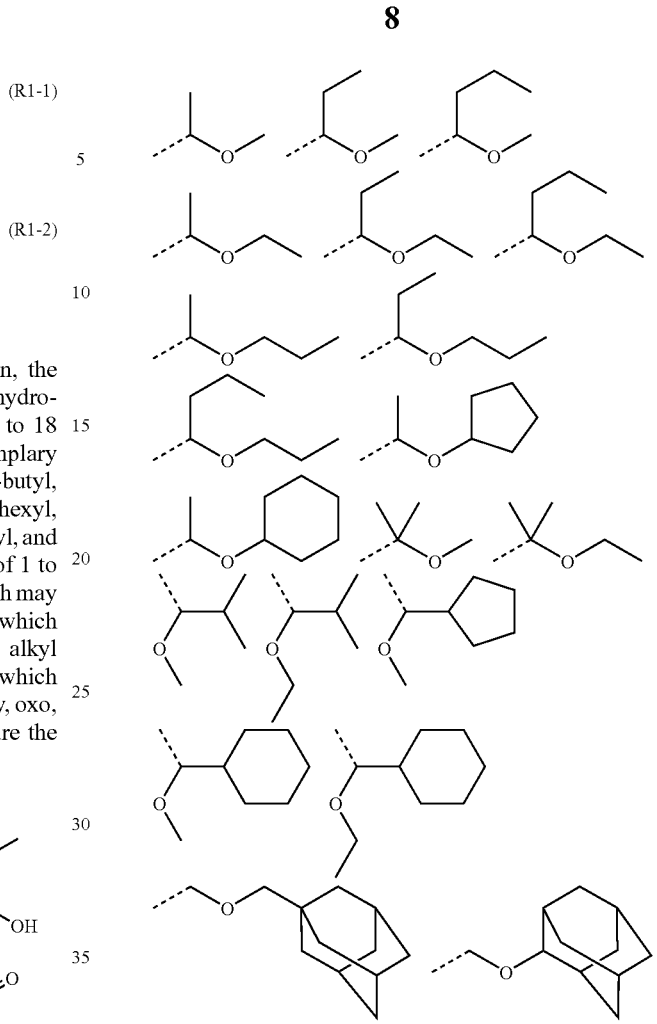

Of the protective groups of formula (R1-1), the cyclic ones are, for example, tetrahydrofuran-2-yl, 2-methyltetrahydrofuran-2-yl, tetrahydropyran-2-yl, and 2-methyltetrahydropyran-2-yl.

Examples of the protective groups of formula (R1-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

In formula (1), examples of the straight, branched or cyclic monovalent hydrocarbon groups of 1 to 8 carbon atoms represented by $R^3$ and $R^4$ include methyl, ethyl, n-propyl, isopropyl, n-butyl, sec-butyl, isobutyl, tert-butyl, cyclopentyl, cyclohexyl, 2-ethylhexyl, and n-octyl. $R^3$ and $R^4$ may be the same or different. Where $R^3$ and $R^4$ bond together to form an aliphatic hydrocarbon ring with the carbon atom to which they are attached, the ring specifically has 3 to 16 carbon atoms, and more specifically 4 to 12 carbon atoms.

Examples of the straight, branched or cyclic divalent hydrocarbon group of 1 to 6 carbon atoms represented by A are shown below.

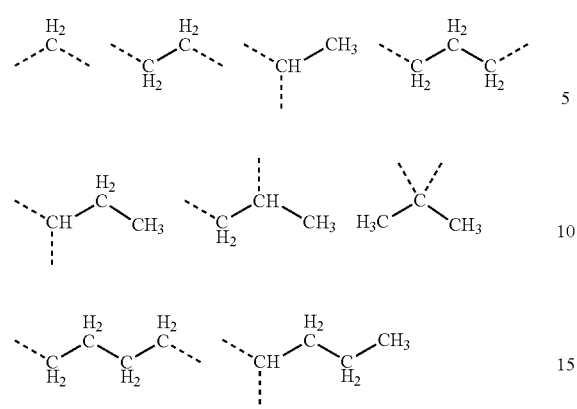
Illustrative, non-limiting examples of the compound having formula (1) are given below.
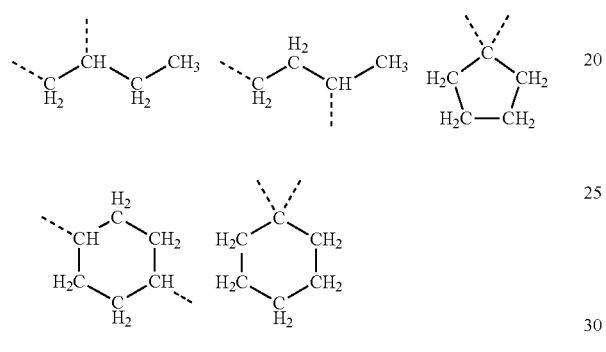
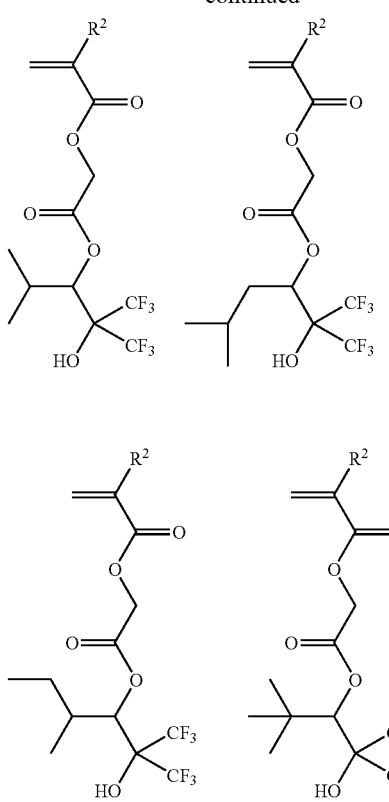
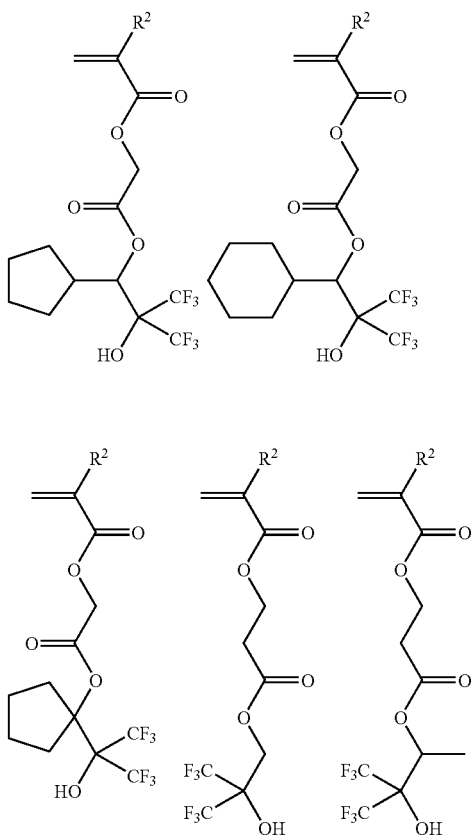

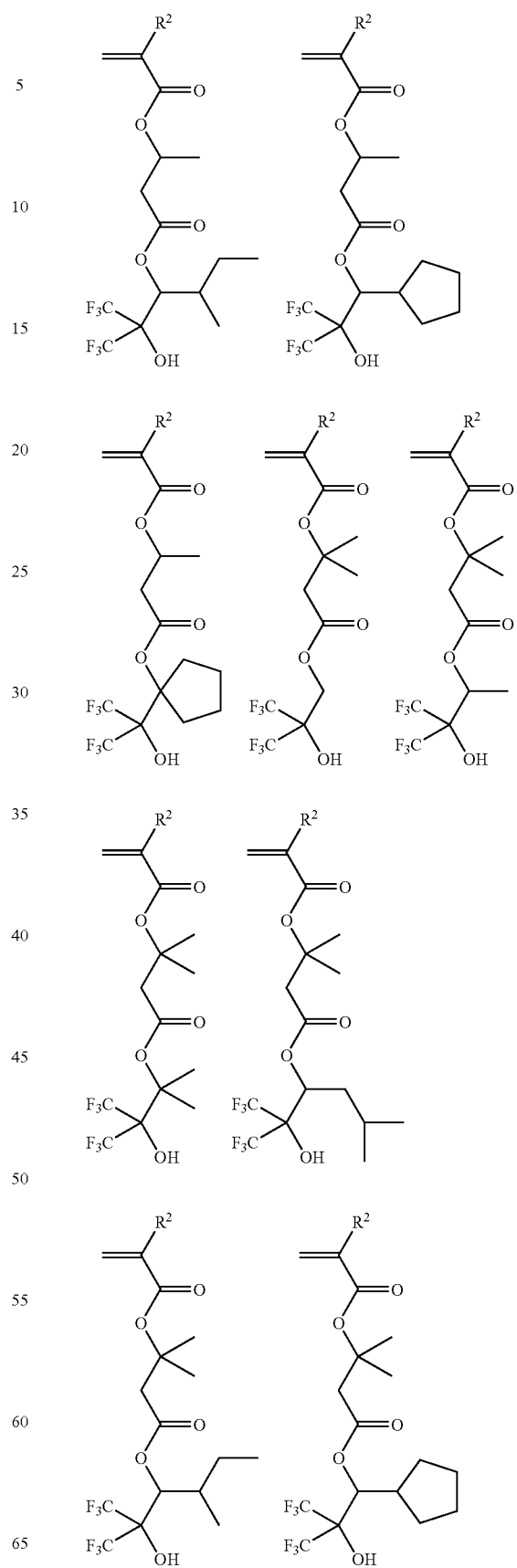

-continued
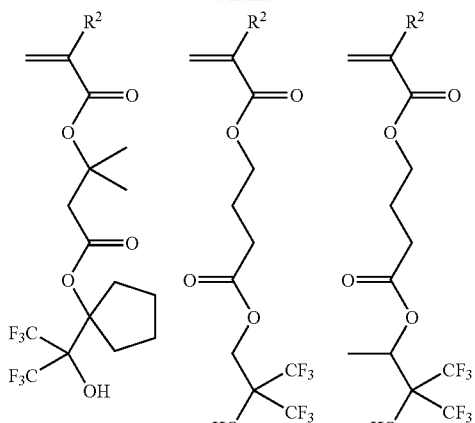
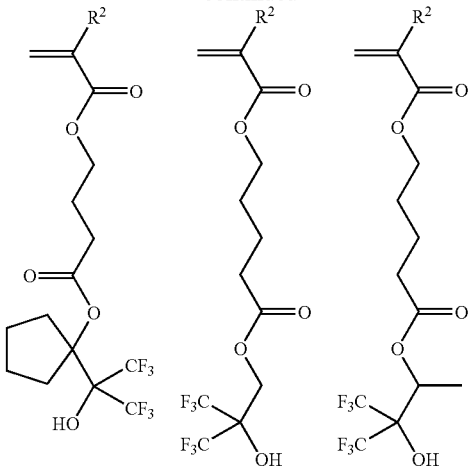
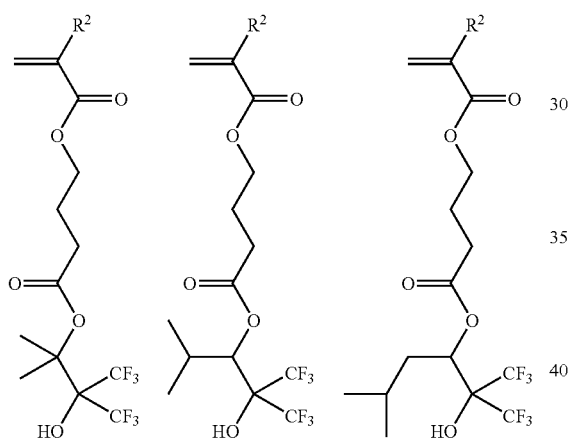
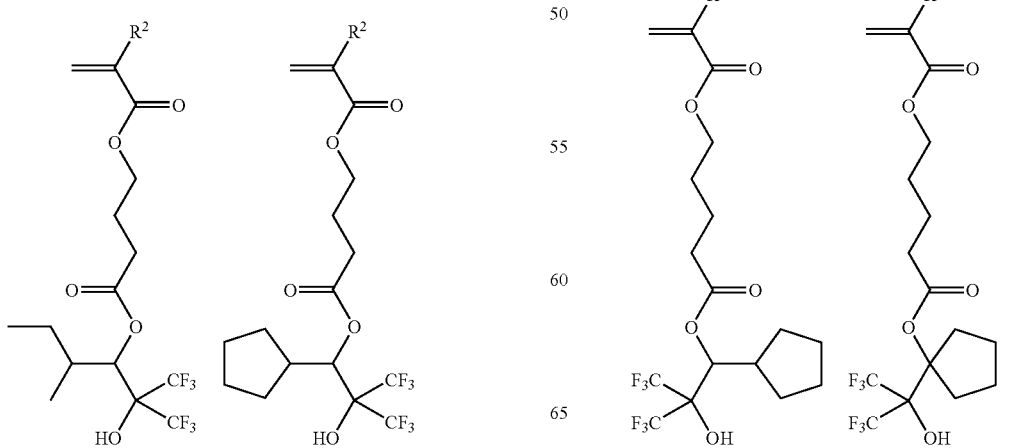

-continued
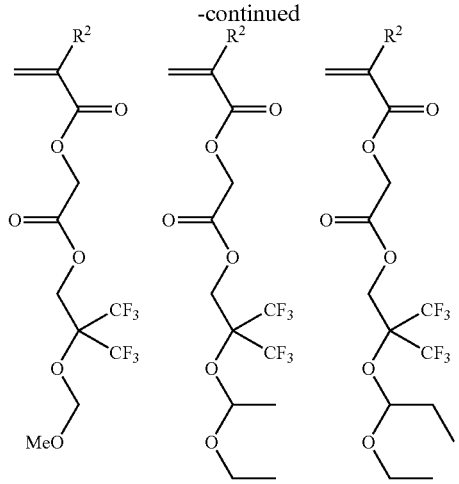
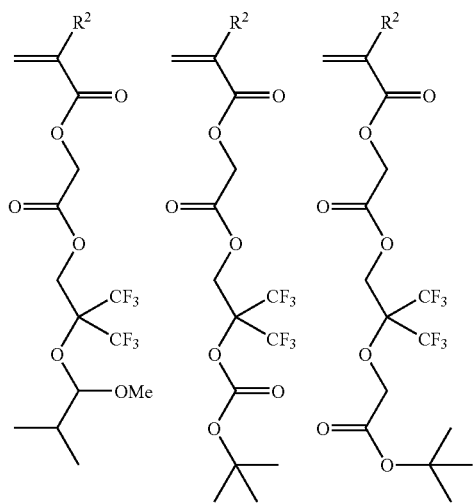
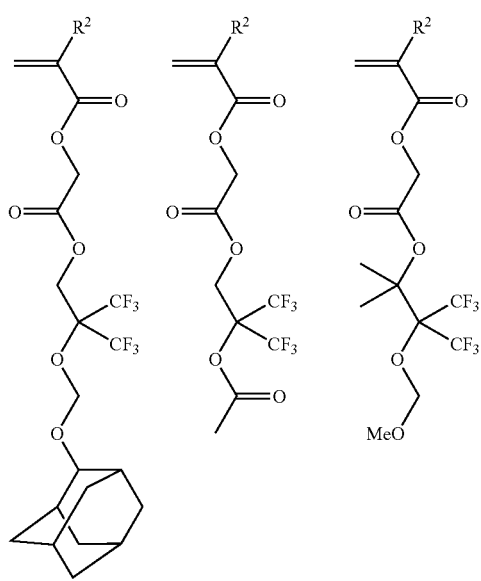
-continued
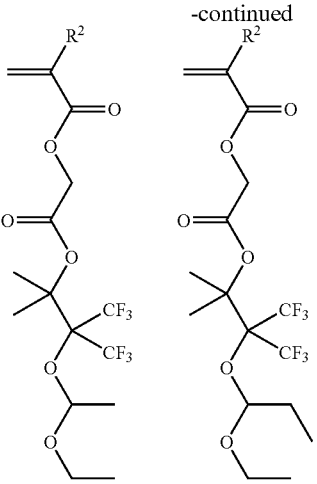
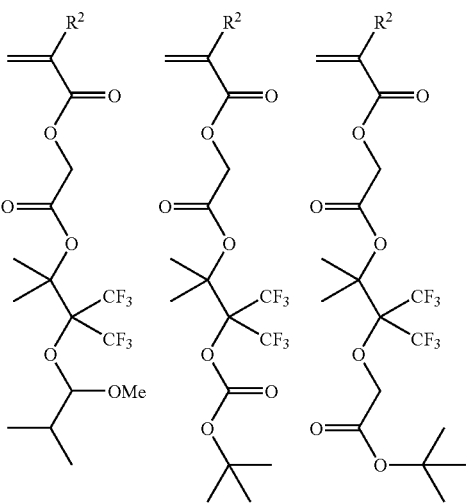
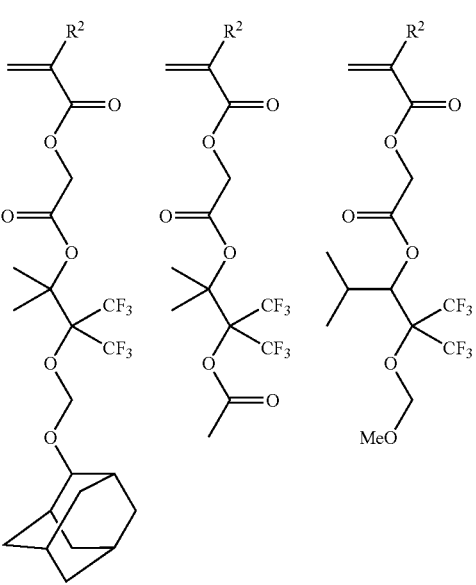

-continued
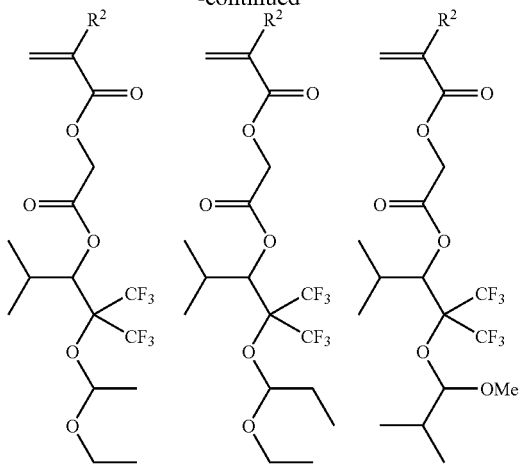
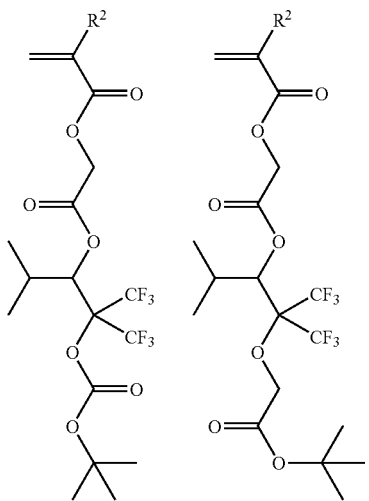
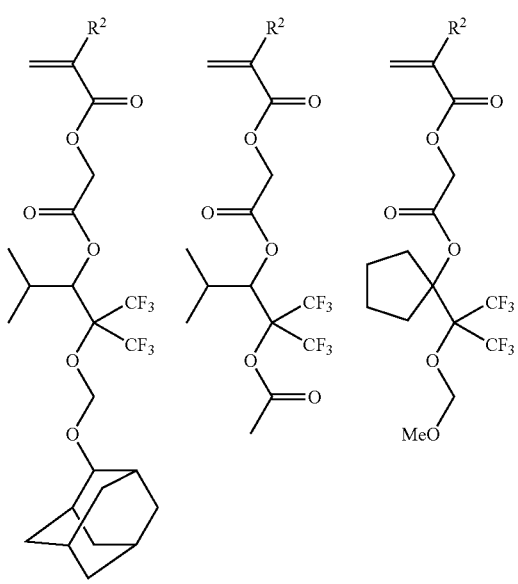
-continued
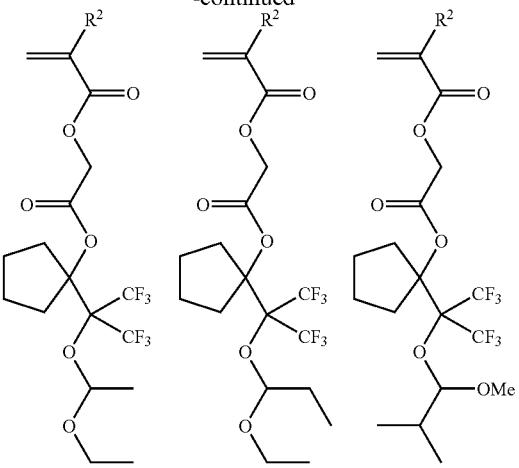
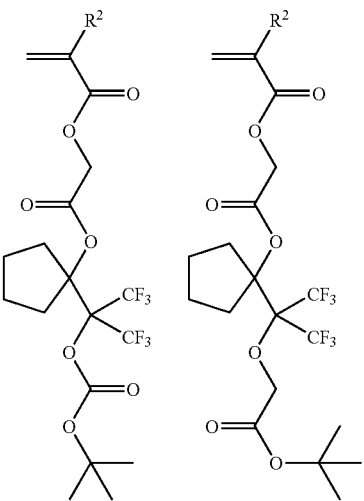
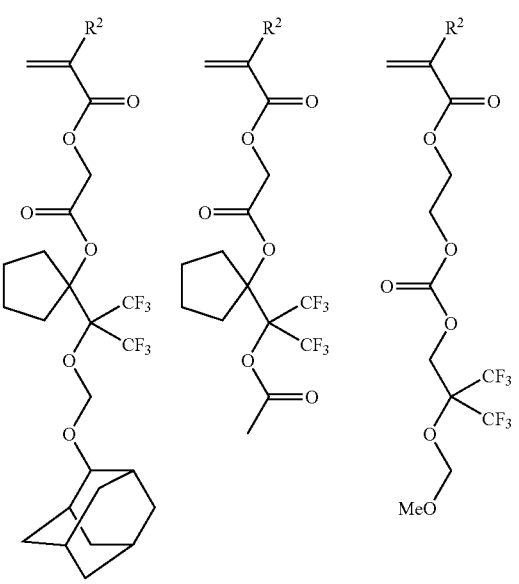

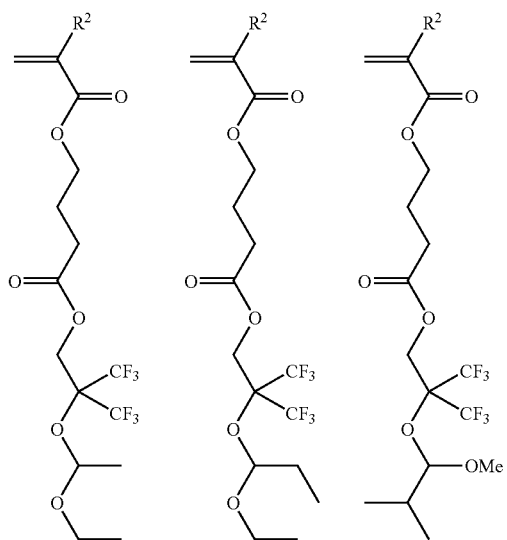
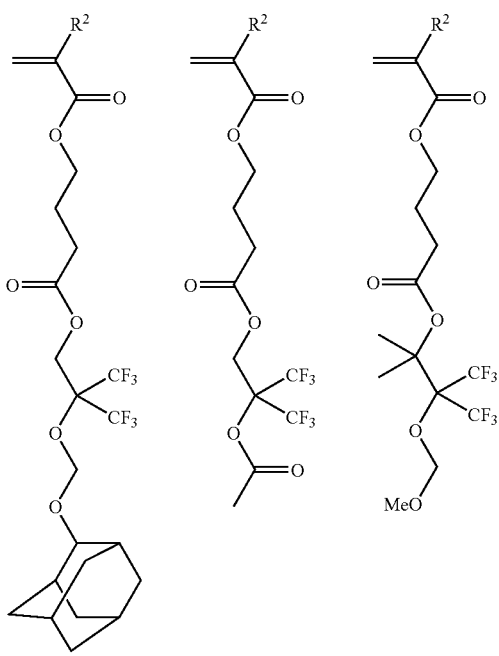
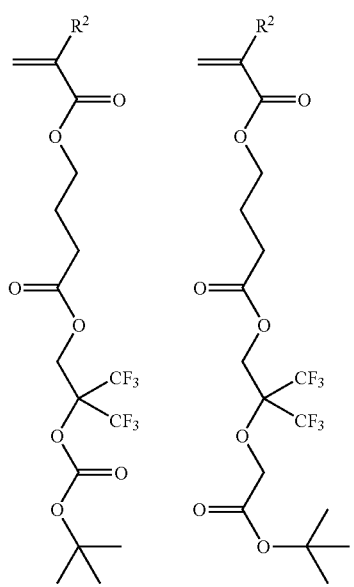
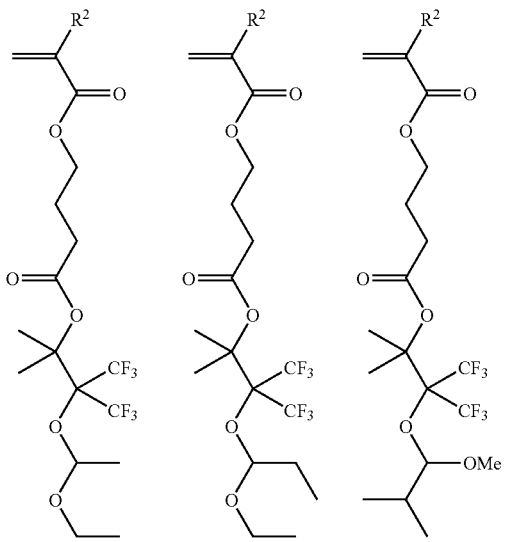

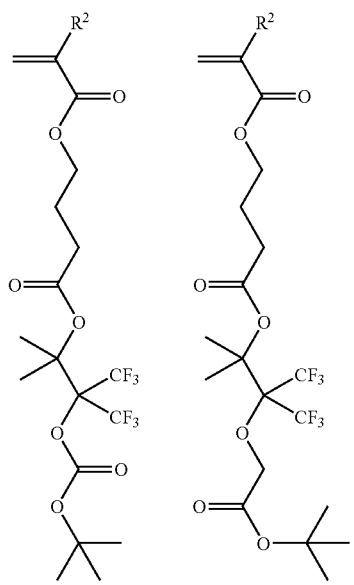
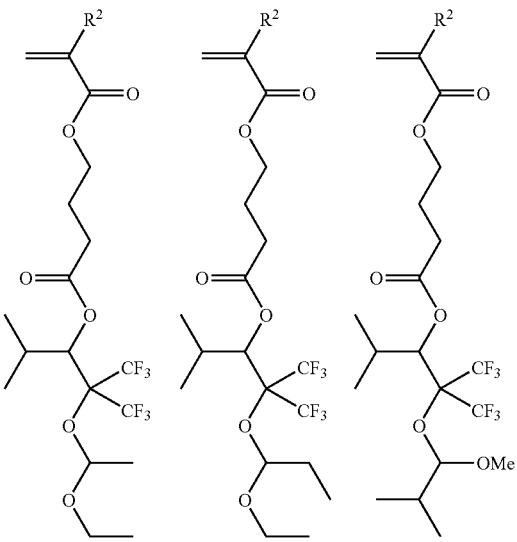
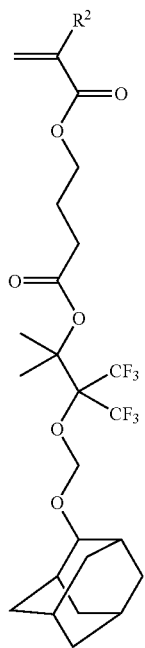
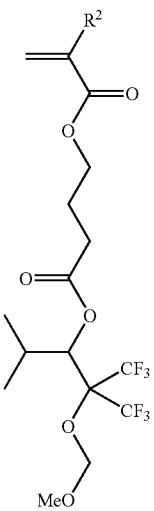
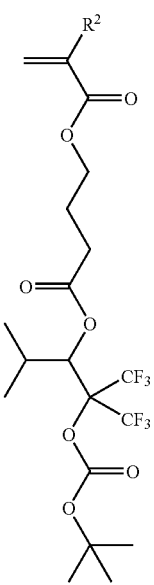
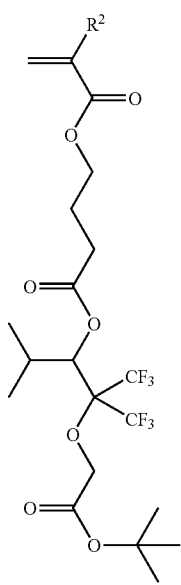

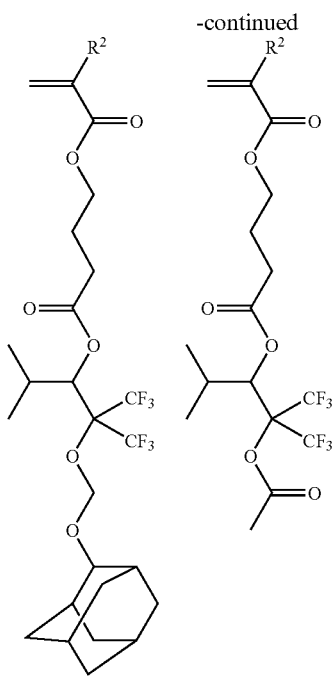

Note that $R^2$ is as defined above.

The fluorinated monomer of formula (1) can be prepared according to the following reaction scheme, for example, although its preparation is not limited thereto.

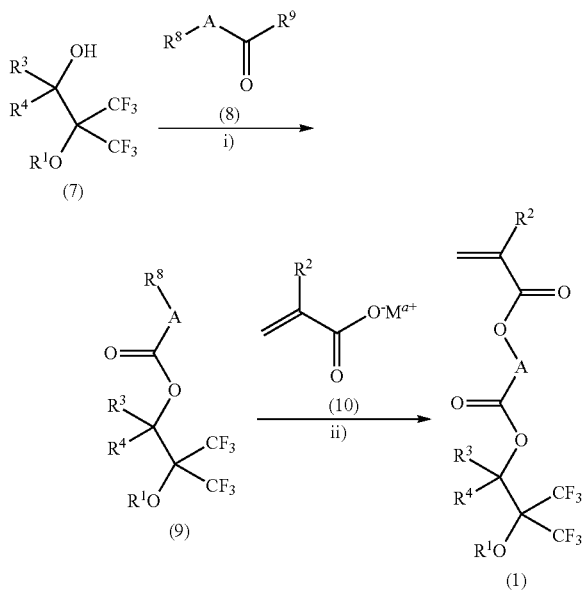

Herein $R^1$ to $R^4$ and A are as defined above, $R^8$ is a halogen atom, $R^9$ is a halogen atom, hydroxyl group or —$OR^{10}$, and $R^{10}$ is methyl, ethyl or a group of the following formula:

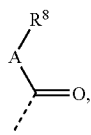

and $M^a$ is Li, Na, K, Mg, Ca or quaternary nitrogen atom. Step i): reaction of fluoroalcohol (7) with esterifying agent (8) to form halo-ester (9)

It is noted that the synthesis of the fluoroalcohol (7) is described in US 2007/179309A (JP Appln. 2006-022319). For example, a fluoroalcohol (7) wherein $R^3$ and $R^4$ are monovalent hydrocarbon groups can be synthesized by reaction of a fluorine compound (11) with corresponding organometallic reagents (12) and (13) according to the following scheme.

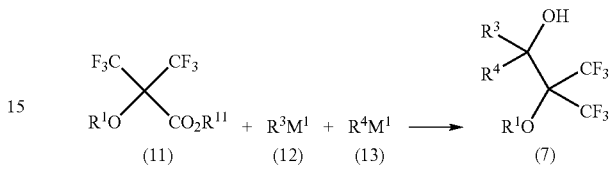

Herein $R^1$ to $R^4$ are as defined above, $R^{11}$ is hydrogen or a straight, branched or cyclic monovalent hydrocarbon group of 1 to 6 carbon atoms, $M^1$ is Li, Na, K, MgX or ZnX which may be substituted, and X is a halogen atom.

Step i) or esterification reaction takes place readily by a well-known technique. The esterifying agent (8) used herein is preferably an acid chloride (corresponding to formula (8) wherein $R^9$ is chlorine) or a carboxylic acid (corresponding to formula (8) wherein $R^9$ is hydroxyl). Where an acid chloride is used, the reaction may be conducted in a solventless system or in a solvent such as methylene chloride, toluene, hexane, diethyl ether, tetrahydrofuran or acetonitrile, by sequentially or simultaneously adding the fluoroalcohol (7), the corresponding acid chloride (e.g., 2-chloroacetic acid chloride or 2-bromoacetic acid chloride), and a base (e.g., triethylamine, pyridine or 4-dimethylaminopyridine) or a metal hydride (e.g., sodium hydride) or an organometallic (e.g., butyllithium and ethylmagnesium bromide), and allowing the reaction to take place while cooling or heating if necessary. Where a carboxylic acid is used, the reaction may be conducted in a solvent such as toluene or hexane, by adding the fluoroalcohol (7), the corresponding carboxylic acid (e.g., 2-chloroacetic acid or 2-bromoacetic acid), a mineral acid (e.g., hydrochloric acid, sulfuric acid, nitric acid or perchloric acid), and an organic acid (e.g., p-toluenesulfonic acid or benzenesulfonic acid), heating the system, and removing the water resulting from reaction out of the system, if necessary.

Step ii): Reaction of halo-ester (9) with carboxylic acid Salt (10) to Form Fluorinated Monomer (1)

The reaction may be carried out by a standard technique. The carboxylic acid salt (10) used herein may be any of commercially available carboxylic acid salts including metal salts of various carboxylic acids as such, or a carboxylic acid salt may be prepared in a reaction system using a corresponding carboxylic acid such as methacrylic acid or acrylic acid and a base. The amount of carboxylic acid salt (10) used is preferably 0.5 to 10 moles, and more preferably 1.0 to 3.0 moles per mole of the reactant, halo-ester (9). Less than 0.5 mole of carboxylic acid salt may lead to significantly reduced yields because a larger amount of the reactant is left unreacted. Using more than 10 moles of carboxylic acid salt may be uneconomical due to increased material costs and reduced pot yields. Where the carboxylic acid salt is prepared in a reaction system using a corresponding carboxylic acid and a base, examples of the base which can be used herein include amines such as ammonia, triethylamine, pyridine, lutidine, collidine and N,N-dimethylaniline; hydroxides such as sodium hydroxide, potassium hydroxide and tetramethylammonium hydroxide; carbonates such as potassium carbonate and sodium hydrogencarbonate; metals such as sodium; metal hydrides such as sodium hydride; metal alkoxides such as sodium methoxide and potassium t-butoxide; organometallics such as butyllithium and ethylmagnesium bromide; and metal amides such as lithium diisopropylamide, and mixtures of two or more of the foregoing. The amount of base used is preferably 0.2 to 10 moles, and more preferably 0.5 to 2.0 moles per mole of the corresponding carboxylic acid. Less than 0.2 mole of the base may lead to an economical disadvantage because a larger amount of the carboxylic acid runs to waste. More than 10 moles of the base may promote side reactions, leading to substantially reduced yields.

Examples of the solvent which can be used for the reaction of step ii) include hydrocarbons such as toluene, xylene, hexane and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethylsulfoxide; and water, alone or in admixture. A phase transfer catalyst such as tetrabutylammonium hydrogen sulfate may be added to the reaction system. The amount of phase transfer catalyst used may be preferably 0.0001 to 1.0 mole, and more preferably 0.001 to 0.5 mole per mole of the reactant halo-ester. Less than 0.0001 mole of the catalyst may fail to achieve the desired addition effect whereas more than 1.0 mole may be uneconomical due to an increased material cost.

The esterification reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is preferred. Since substantial side reactions may occur at elevated temperatures, it is crucial in achieving high yields to carry out the reaction at a temperature as low as possible within the range where reaction proceeds at a practically acceptable rate. It is desired for higher yields that the reaction time be determined by monitoring the progress of reaction by thin-layer chromatography (TLC) or gas chromatography (GC). The reaction time is usually about 30 minutes to about 40 hours. The fluorinated monomer (1) may be recovered from the reaction mixture by ordinary aqueous work-up. If necessary, it can be purified by any standard technique such as distillation, recrystallization or chromatography.

In a second embodiment of the invention, the fluorinated monomer has the general formula (2).

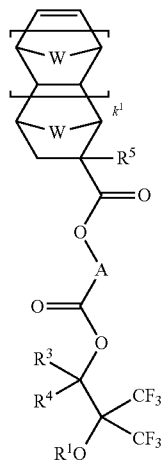

(2)

Herein $R^1$, $R^3$, $R^4$, and A are as defined above, $R^5$ is a hydrogen atom, fluorine atom, methyl group or trifluoromethyl group, W is —$CH_2$— or —O—, and $k^1$ is equal to 0 or 1.

Illustrative, non-limiting examples of the compound having formula (2) are given below.

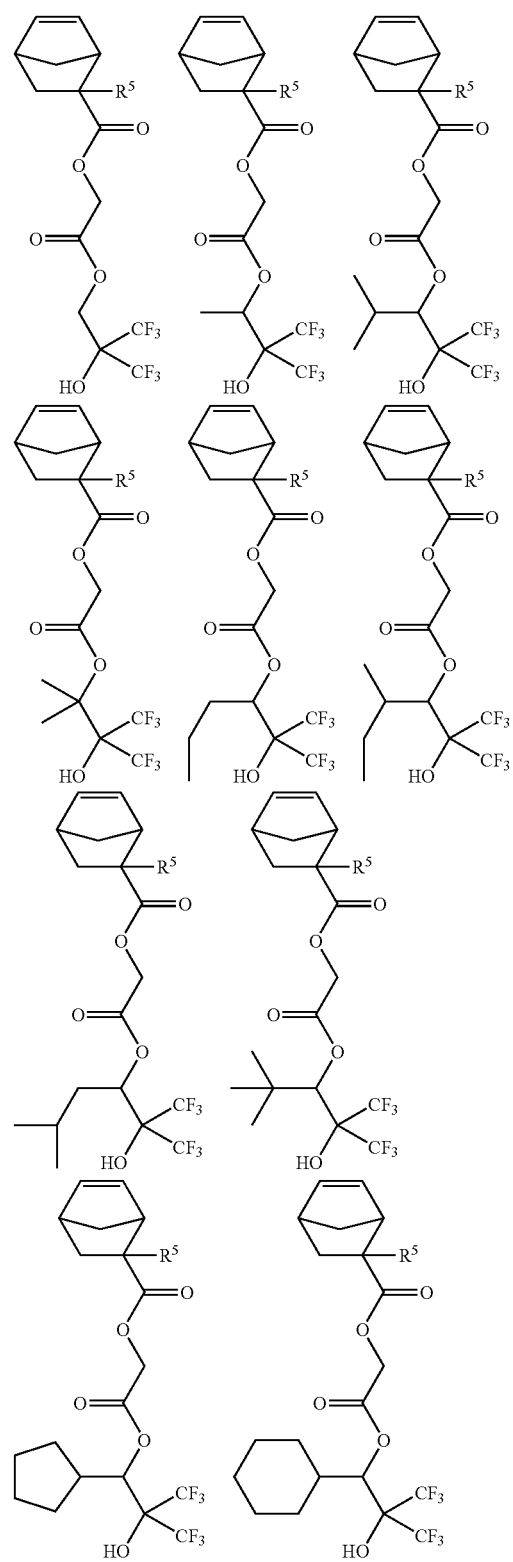

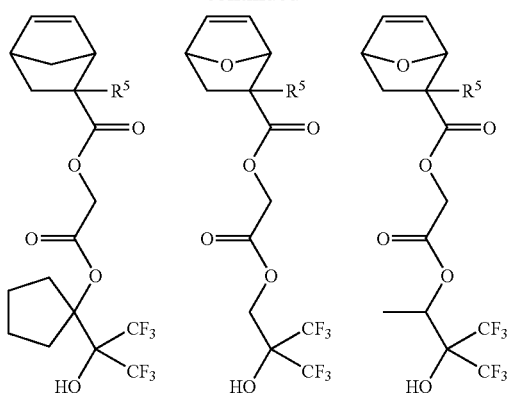
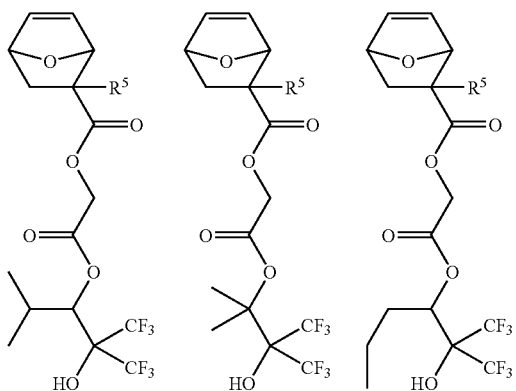
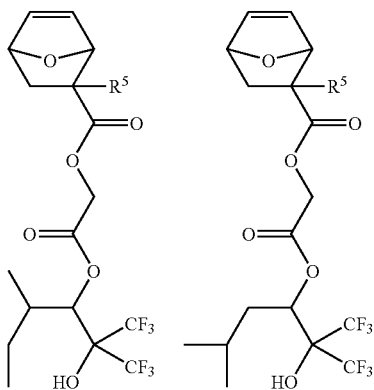
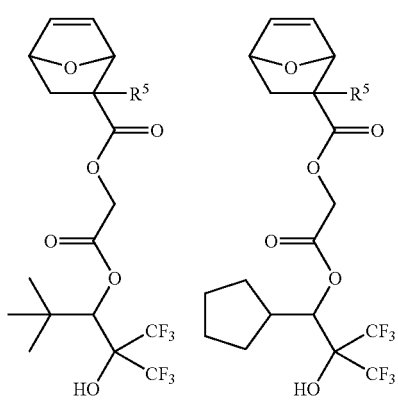
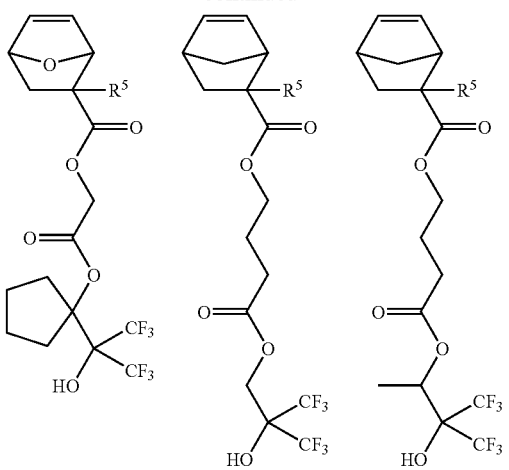
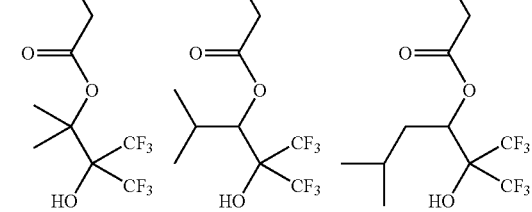
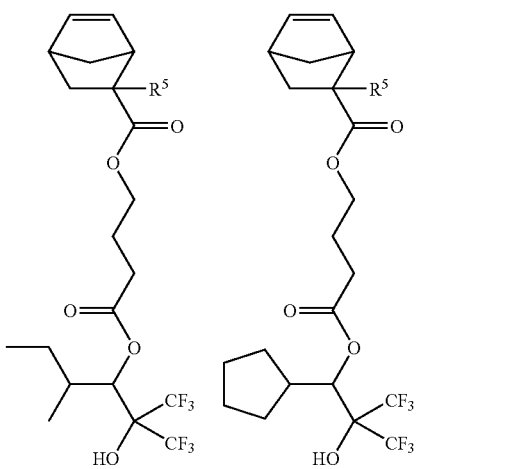

29
-continued
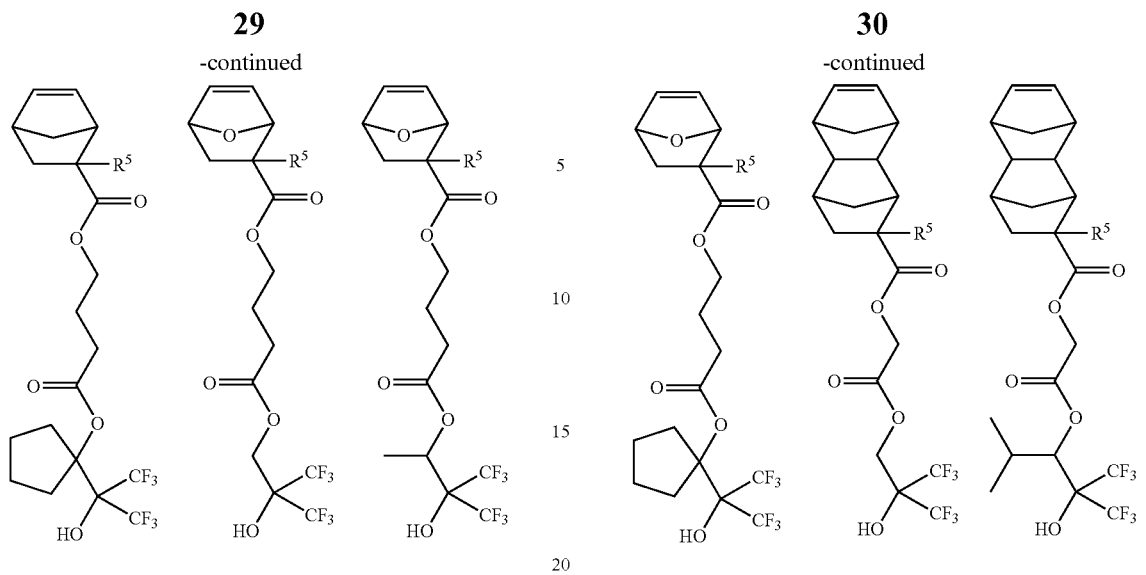
30
-continued
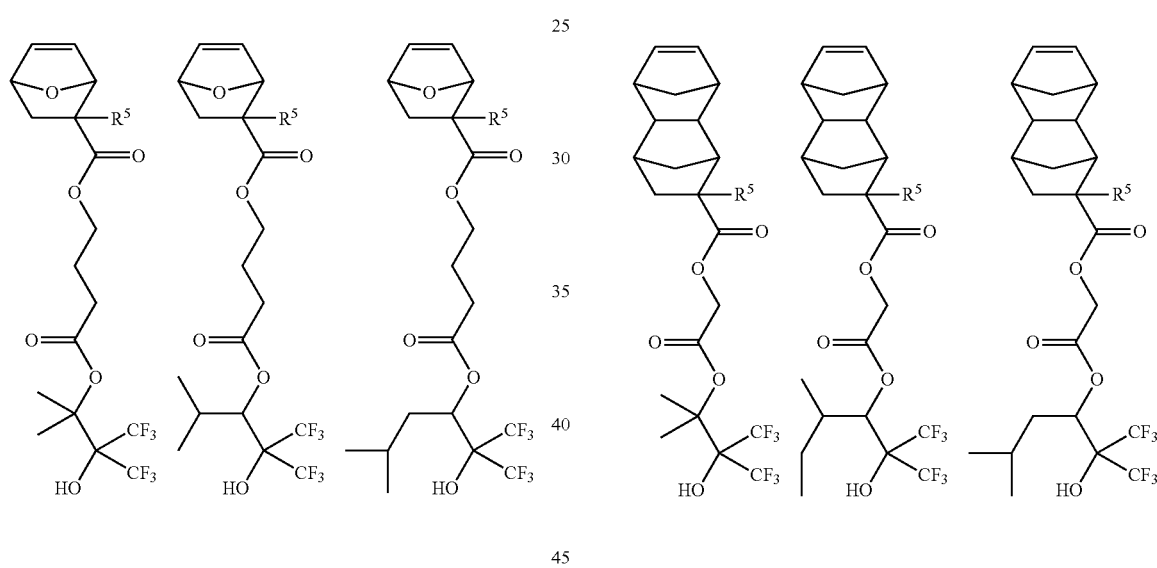
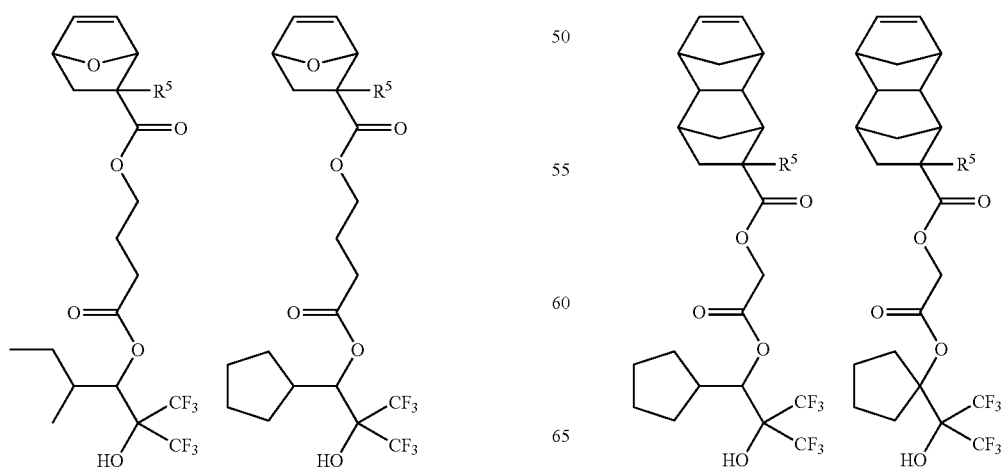

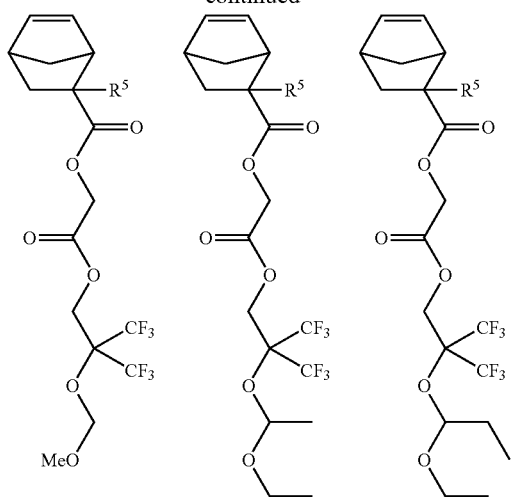
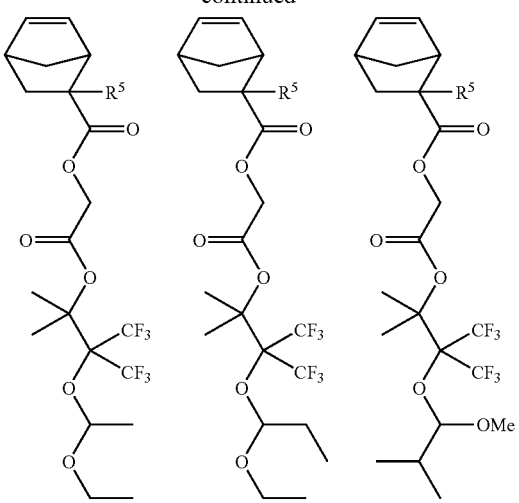
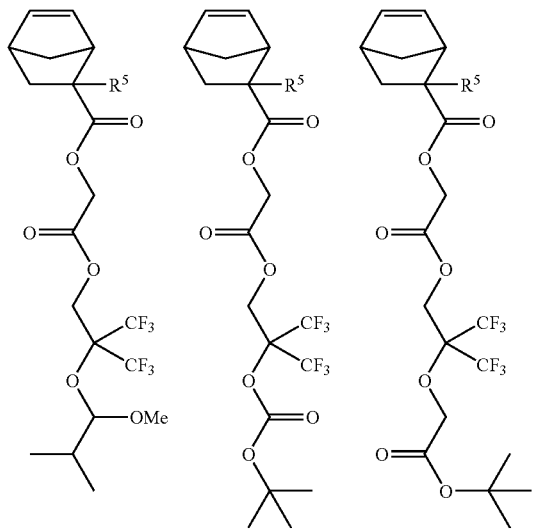
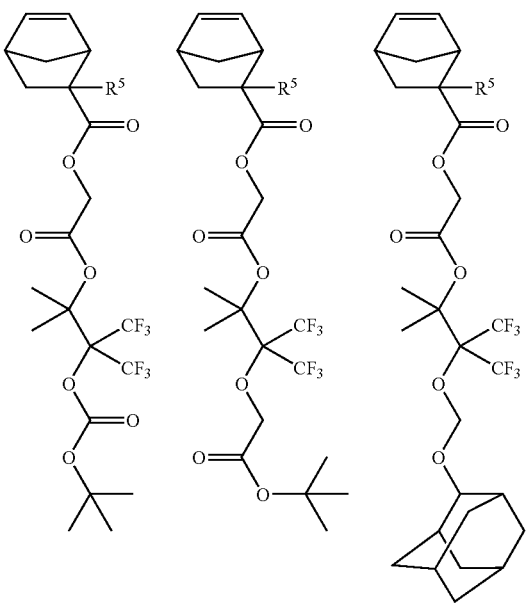
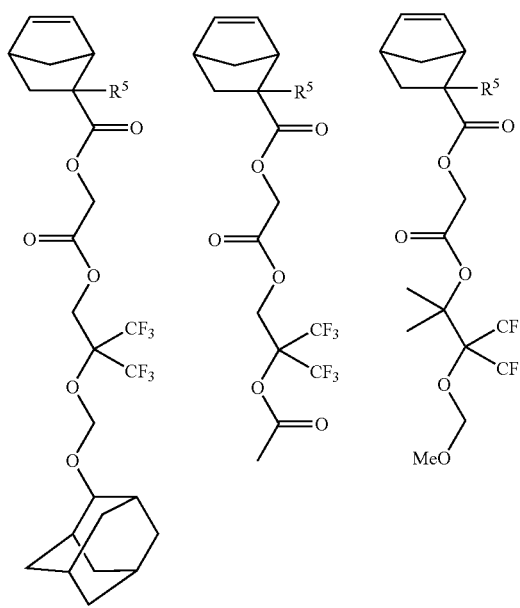
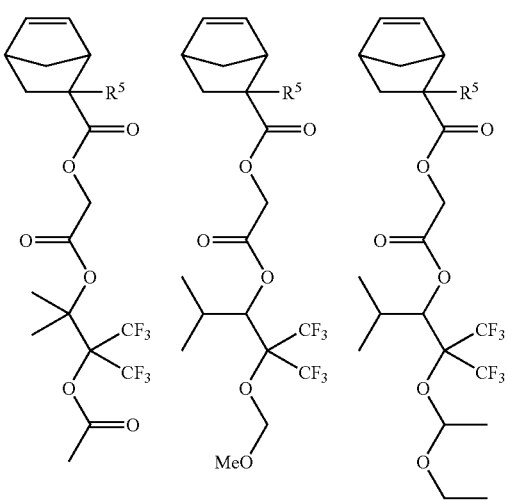

-continued

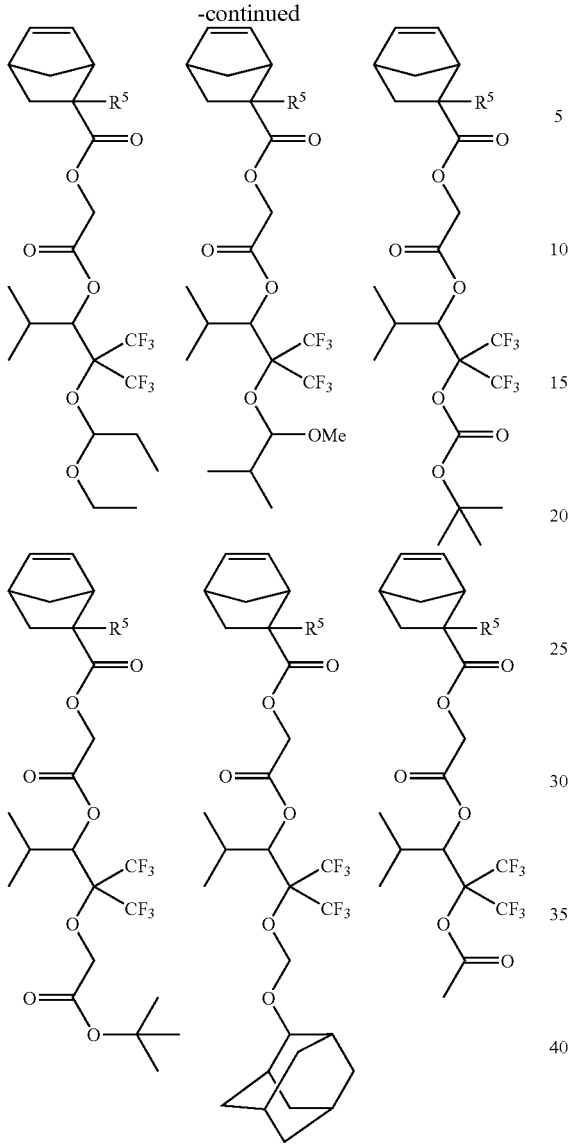

Note that $R^5$ is as defined above.

The fluorinated monomer of formula (2) can be prepared according to the following reaction scheme, for example, although its preparation is not limited thereto.

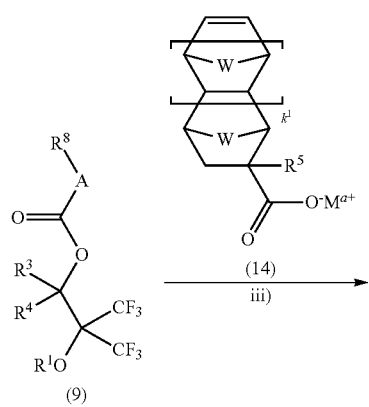

-continued

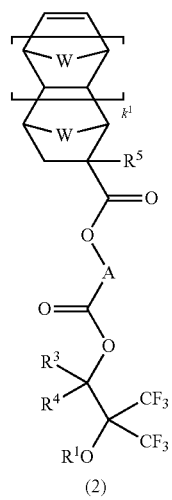

Herein $R^1$, $R^3$, $R^4$, $R^5$, $R^8$, A, W, $k^1$ and $M^a$ are as defined above.

Step iii): Reaction of halo-ester (9) with carboxylic acid Salt (14) to Form Fluorinated Monomer (2)

The reaction may be carried out by a standard technique. The carboxylic acid salt (14) used herein may be any of commercially available carboxylic acid salts including metal salts of various carboxylic acids as such, or a carboxylic acid salt may be prepared in a reaction system using a corresponding carboxylic acid such as 5-norbornene-2-carboxylic acid or 7-oxa-5-norbornene-2-carboxylic acid and a base. The amount of carboxylic acid salt (14) used is preferably 0.5 to 10 moles, and more preferably 1.0 to 3.0 moles per mole of the reactant, halo-ester (9). Less than 0.5 mole of carboxylic acid salt may lead to significantly reduced yields because a larger amount of the reactant is left unreacted. Using more than 10 moles of carboxylic acid salt may be uneconomical due to increased material costs and reduced pot yields. Where the carboxylic acid salt is prepared in a reaction system using a corresponding carboxylic acid and a base, examples of the base which can be used herein include amines such as ammonia, triethylamine, pyridine, lutidine, collidine and N,N-dimethylaniline; hydroxides such as sodium hydroxide, potassium hydroxide and tetramethylammonium hydroxide; carbonates such as potassium carbonate and sodium hydrogencarbonate; metals such as sodium; metal hydrides such as sodium hydride; metal alkoxides such as sodium methoxide and potassium t-butoxide; organometallics such as butyllithium and ethylmagnesium bromide; and metal amides such as lithium diisopropylamide, and mixtures of two or more of the foregoing. The amount of base used is preferably 0.2 to 10 moles, and more preferably 0.5 to 2.0 moles per mole of the corresponding carboxylic acid. Less than 0.2 mole of the base may lead to an economical disadvantage because a larger amount of the carboxylic acid runs to waste. More than 10 moles of the base may promote side reactions, leading to substantially reduced yields.

Examples of the solvent which can be used for the reaction of step iii) include hydrocarbons such as toluene, xylene, hexane and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitrites such as acetonitrile; alcohols such as methanol and ethanol; aprotic polar solvents such as N,N-dimethylformamide, N,N-dimethylacetamide and dimethylsulfoxide; and water, alone or in admixture. A phase transfer catalyst such as tetrabutylammonium hydrogen sulfate may be added to the reaction system. The amount of phase transfer catalyst used may be preferably 0.0001 to 1.0 mole, and more preferably 0.001 to 0.5 mole per mole of the reactant, haloester. Less than 0.0001 mole of the catalyst may fail to achieve the desired addition effect whereas more than 1.0 mole may be uneconomical due to an increased material cost.

The esterification reaction may be carried out preferably at a temperature in the range from −70° C. to approximately the boiling point of a particular solvent used. While an appropriate reaction temperature may be selected in accordance with other reaction conditions, a temperature in the range from 0° C. to approximately the boiling point of a particular solvent used is preferred. Since substantial side reactions may occur at elevated temperatures, it is crucial in achieving high yields to carry out the reaction at a temperature as low as possible within the range where reaction proceeds at a practically acceptable rate. It is desired for higher yields that the reaction time be determined by monitoring the progress of reaction by thin-layer chromatography (TLC) or gas chromatography (GC). The reaction time is usually about 30 minutes to about 40 hours. The fluorinated monomer (2) may be recovered from the reaction mixture by ordinary aqueous work-up. If necessary, it can be purified by any standard technique such as distillation, recrystallization or chromatography.

Alternatively, the end compound (2) can be derived by Diels-Alder reaction of fluorinated monomer (1) with a corresponding diene compound such as furan or cyclopentadiene.

Polymer

The polymer or high molecular weight compound of the invention is characterized by comprising recurring units derived from the fluorinated monomer of formula (1) or (2).

The recurring units derived from the fluorinated monomers of formulas (1) and (2) include those having the general formulas (1a) to (1c).

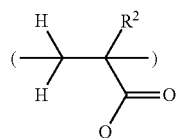
(1a)

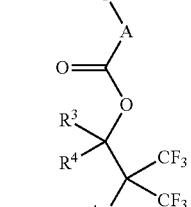
(1b)

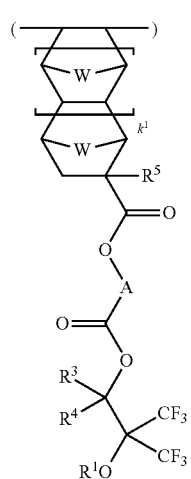

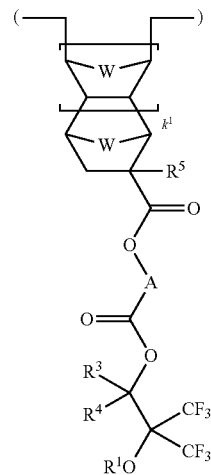
(1c)

Herein $R^1$ to $R^5$, A, W and $k^1$ are as defined above.

In addition to the recurring units derived from the compounds having formulas (1) and (2) such as recurring units having formulas (1a) to (1c), the polymers of the invention may comprise recurring units of at least one type selected from the following general formulas (3) to (6).

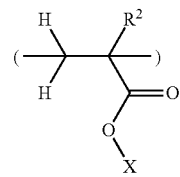
(3)

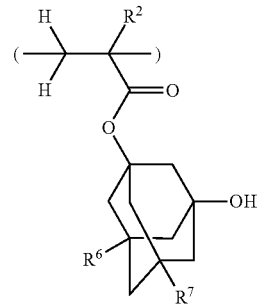
(4)

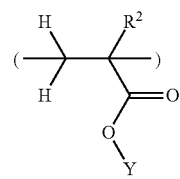
(5)

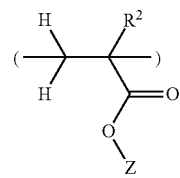
(6)

Herein $R^2$ is as defined above, $R^6$ and $R^7$ are each independently a hydrogen atom or hydroxyl group, X is an acid labile group, Y is a substituent group having a lactone structure, Z is a hydrogen atom, a fluoroalkyl group of 1 to 15 carbon atoms, or a fluoroalcohol-containing substituent group of 1 to 15 carbon atoms.

Under the action of acid, a polymer comprising recurring units of formula (3) is decomposed to generate carboxylic acid, turning to be an alkali soluble polymer. The acid labile group represented by X may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

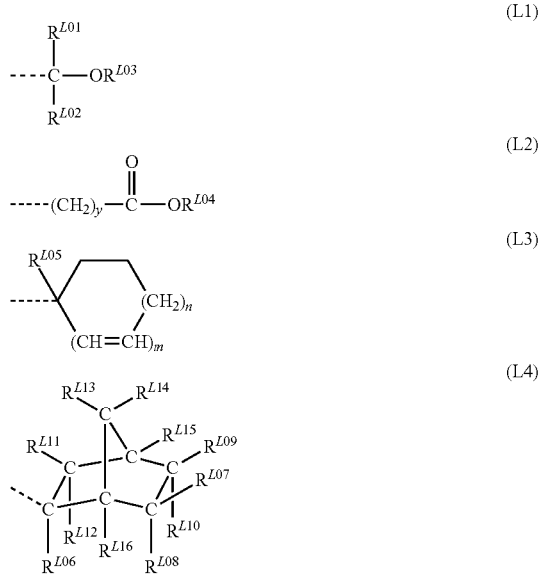

In these formulae, the broken line denotes a valence bond. In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 lo carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

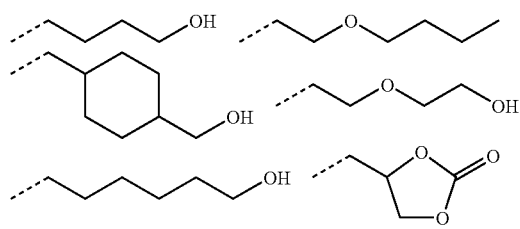

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic alkyl group of 1 to 8 carbon atoms or a substituted or unsubstituted aryl group of 6 to 20 carbon atoms. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a substituted or unsubstituted, straight, branched or cyclic alkyl group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

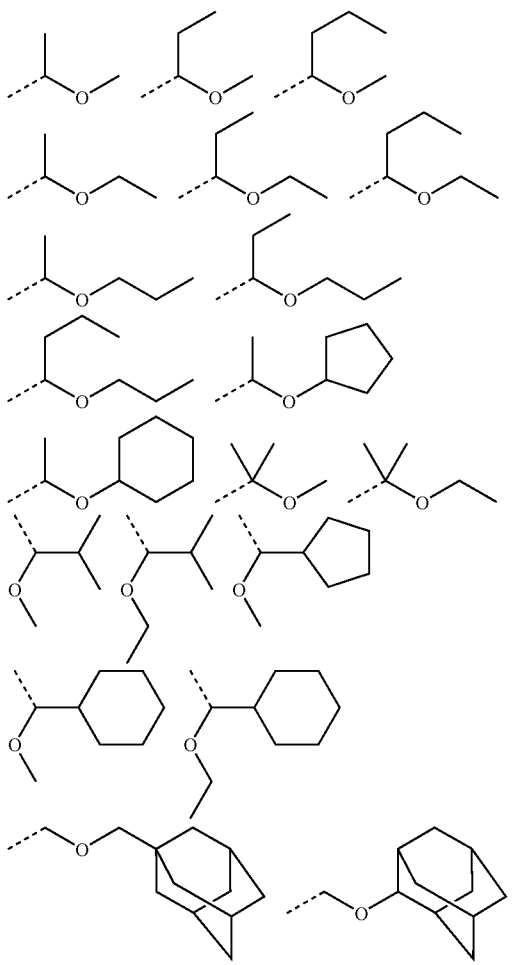

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl,
1,1-diethylpropyloxycarbonyl,
1,1-diethylpropyloxycarbonylmethyl,
1-ethylcyclopentyloxycarbonyl,
1-ethylcyclopentyloxycarbonylmethyl,
1-ethyl-2-cyclopentenyloxycarbonyl,
1-ethyl-2-cyclopentenyloxycarbonylmethyl,
1-ethoxyethoxycarbonylmethyl,
2-tetrahydropyranyloxycarbonylmethyl, and
2-tetrahydrofuranyloxycarbonylmethyl groups.

Examples of the acid labile groups of formula (L3) include 1-methylcyclopentyl, 1-ethylcyclopentyl,
1-n-propylcyclopentyl, 1-isopropylcyclopentyl,
1-n-butylcyclopentyl, 1-sec-butylcyclopentyl,
1-cyclohexylcyclopentyl, 1-(4-methoxy-n-butyl)cyclopentyl,
1-methylcyclohexyl, 1-ethylcyclohexyl,
3-methyl-1-cyclopenten-3-yl, 3-ethyl-1-cyclopenten-3-yl,
3-methyl-1-cyclohexen-3-yl, and
3-ethyl-1-cyclohexen-3-yl groups.

Of the acid labile groups having formula (L4), groups having the following formulas (L4-1) to (L4-4) are preferred.

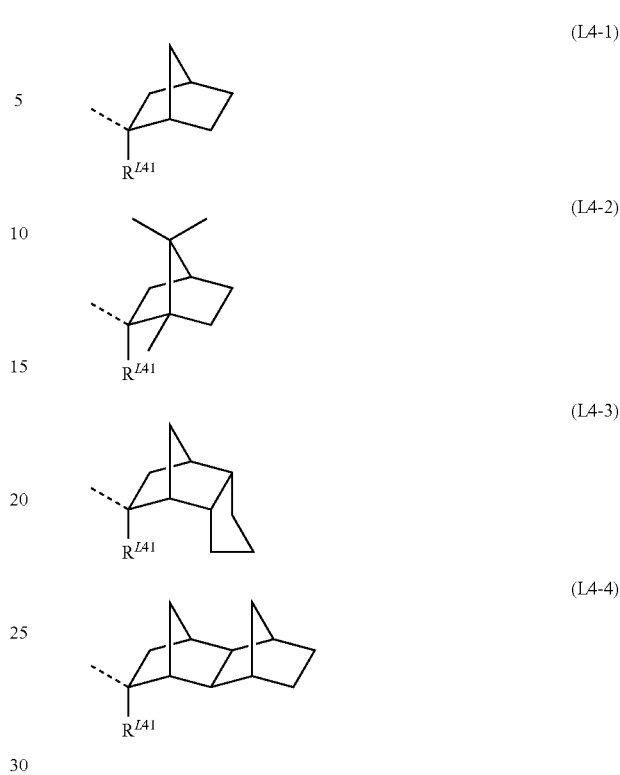

In formulas (L4-1) to (L4-4), the broken line denotes a bonding site and direction. $R^{L41}$ is each independently a monovalent hydrocarbon group, typically a straight, branched or cyclic alkyl group of 1 to 10 carbon atoms, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereolsomers may be used alone or in admixture.

For example, the general formula (L4-3) represents one or a mixture of two or more selected from groups having the following general formulas (L4-3-1) and (L4-3-2).

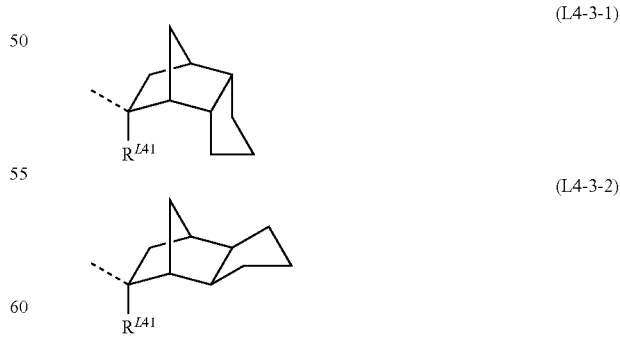

$R^{L41}$ is as defined above.

Similarly, the general formula (L4-4) represents one or a mixture of two or more selected from groups having the following general formulas (L4-4-1) to (L4-4-4).

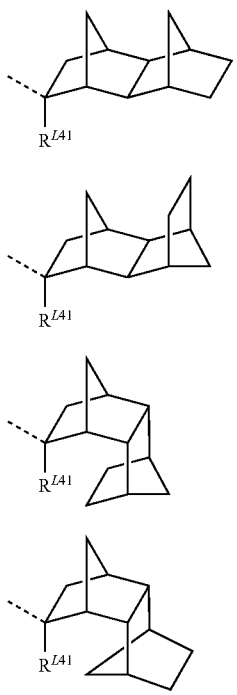

(L4-4-1)

(L4-4-2)

(L4-4-3)

(L4-4-4)

$R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

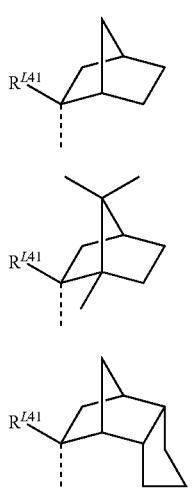

(L4-1-endo)

(L4-2-endo)

(L4-3-endo)

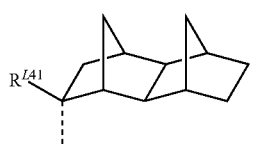

(L4-4-endo)

$R^{L41}$ is as defined above.

Illustrative examples of the acid labile group of formula (L4) are given below

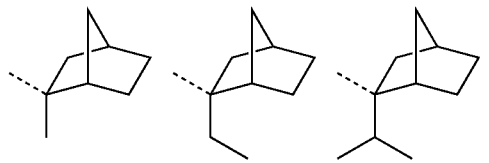

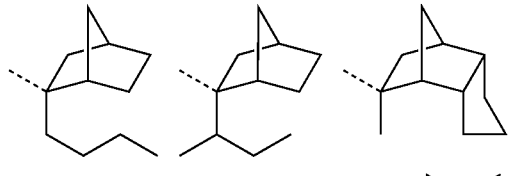

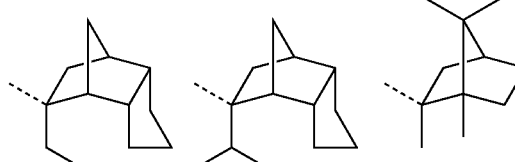

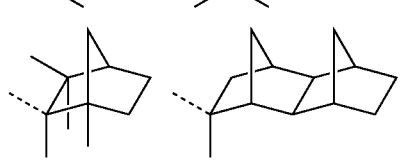

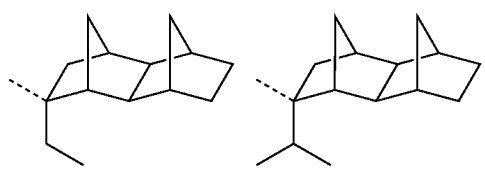

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative, non-limiting examples of the recurring units of formula (3) are given below.

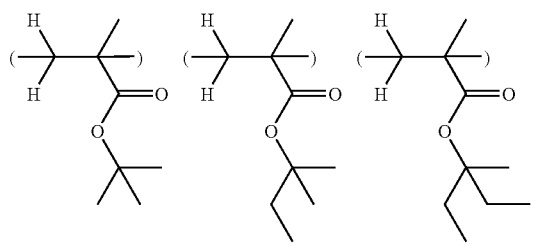

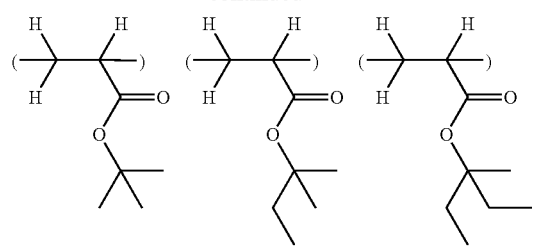
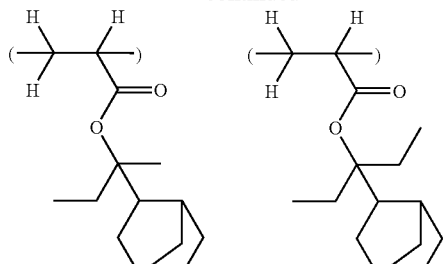
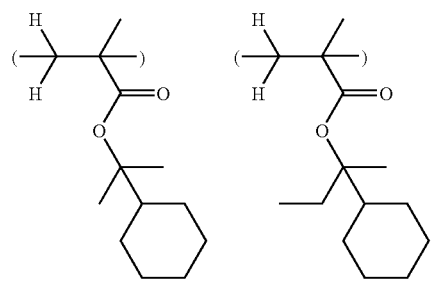
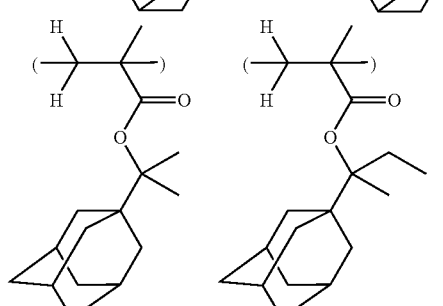
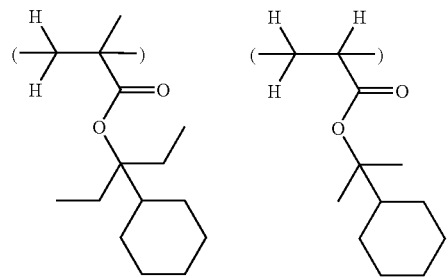
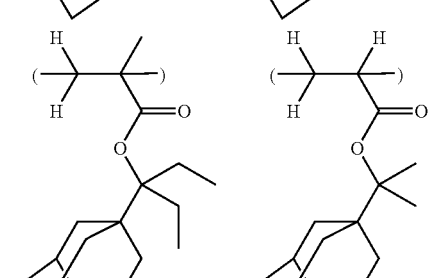
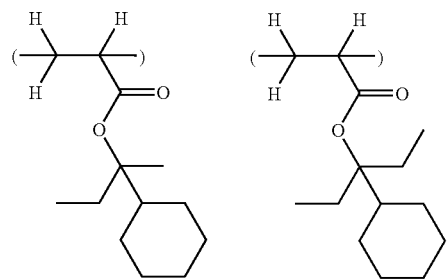
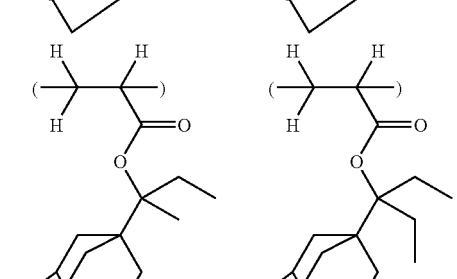
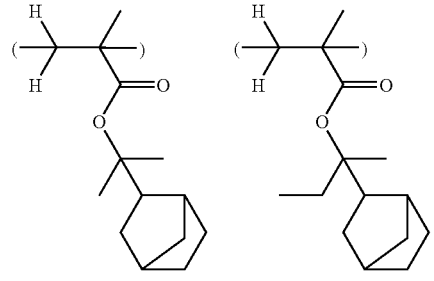
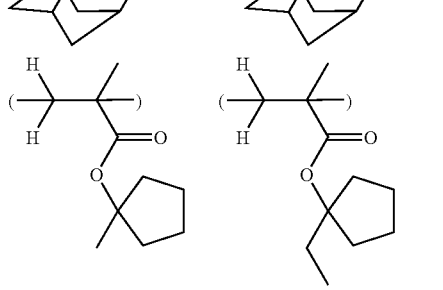
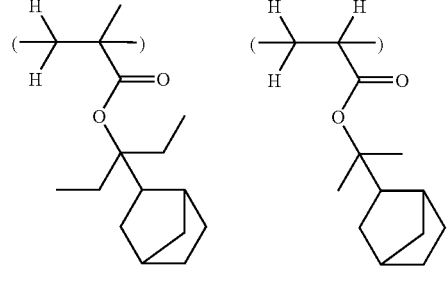
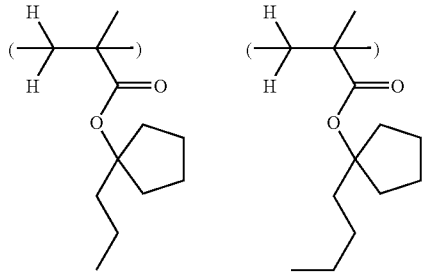

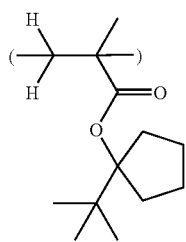 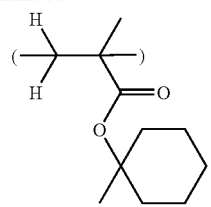 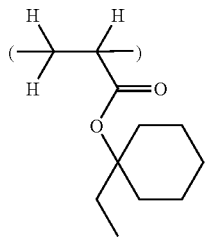 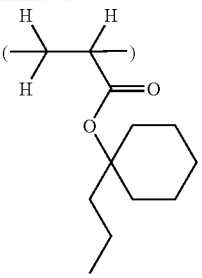
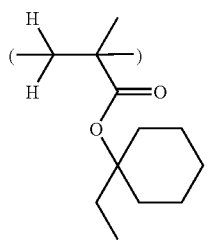 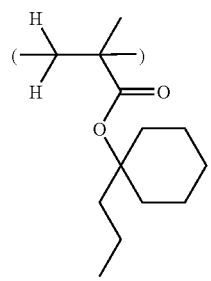 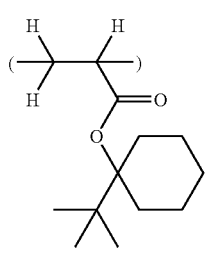 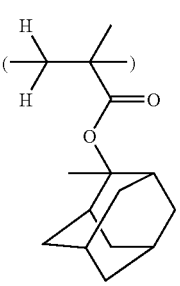
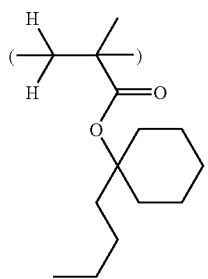 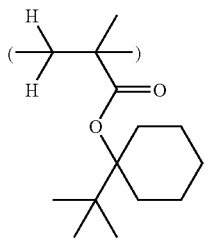 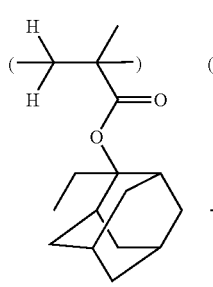 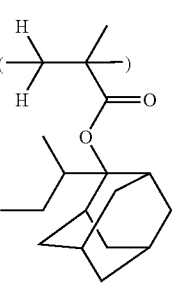
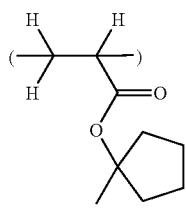 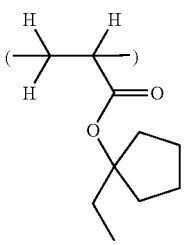 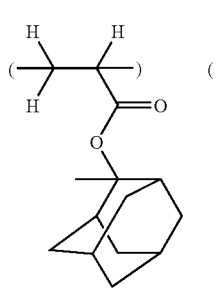 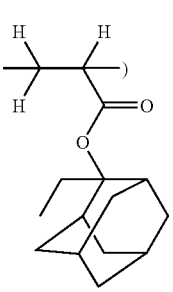
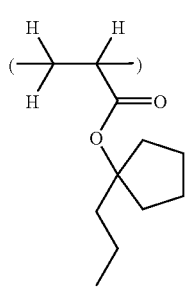 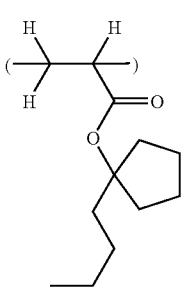 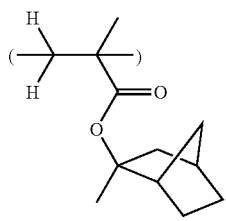 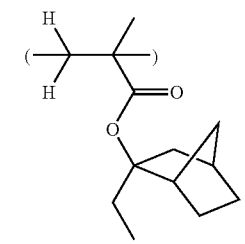
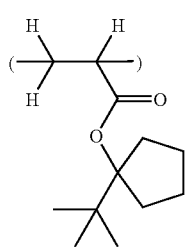 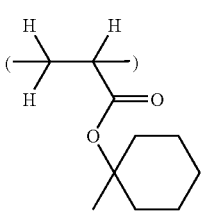 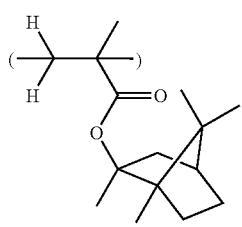 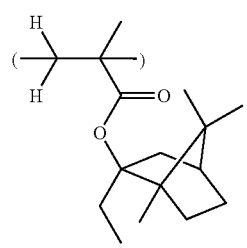

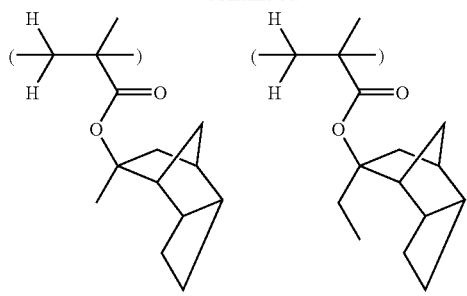
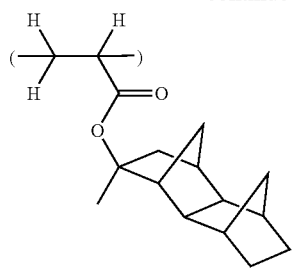
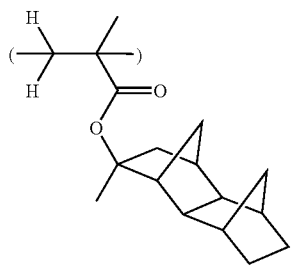
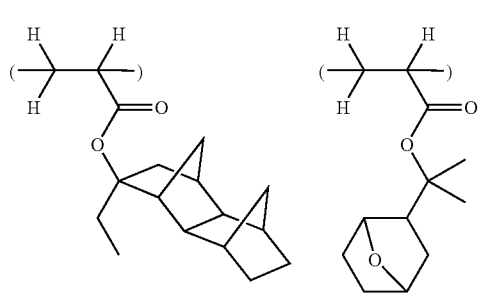
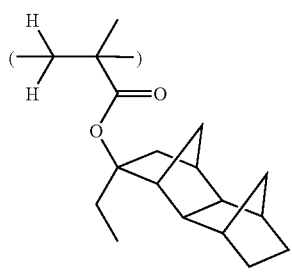
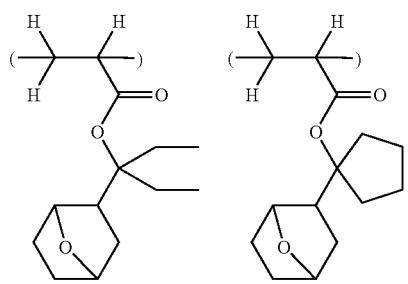
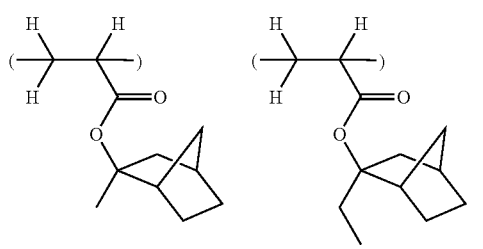
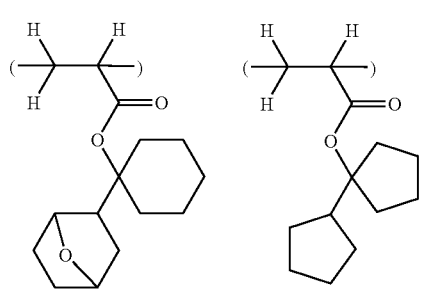
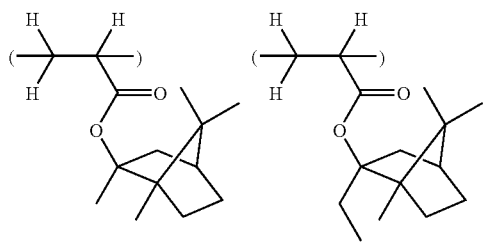
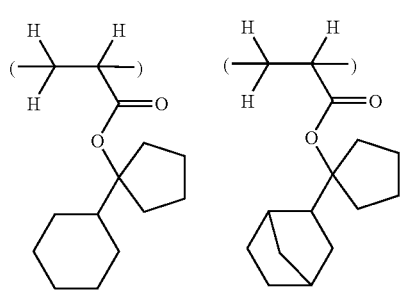
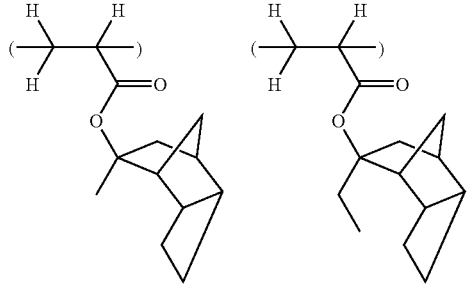

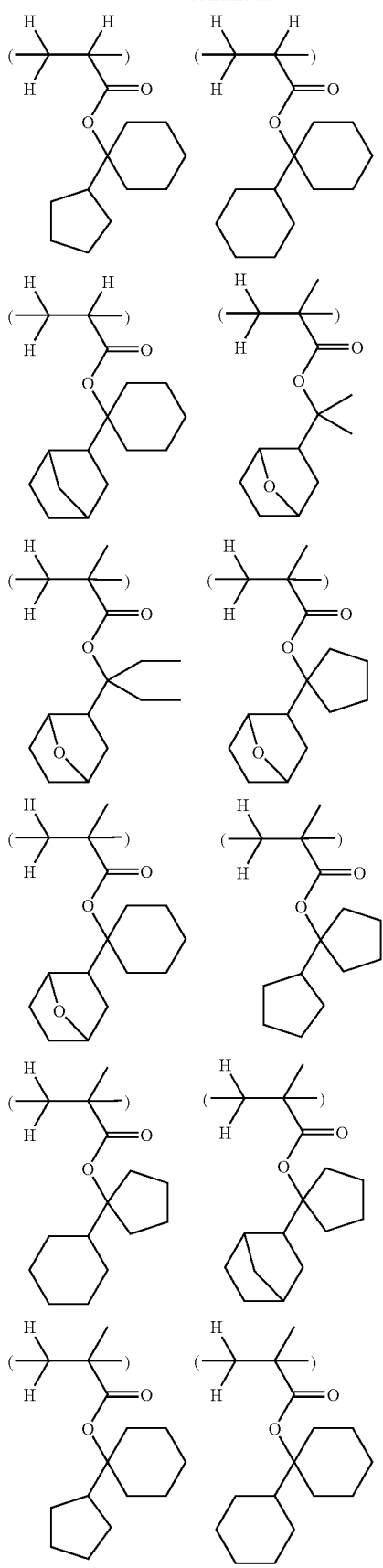
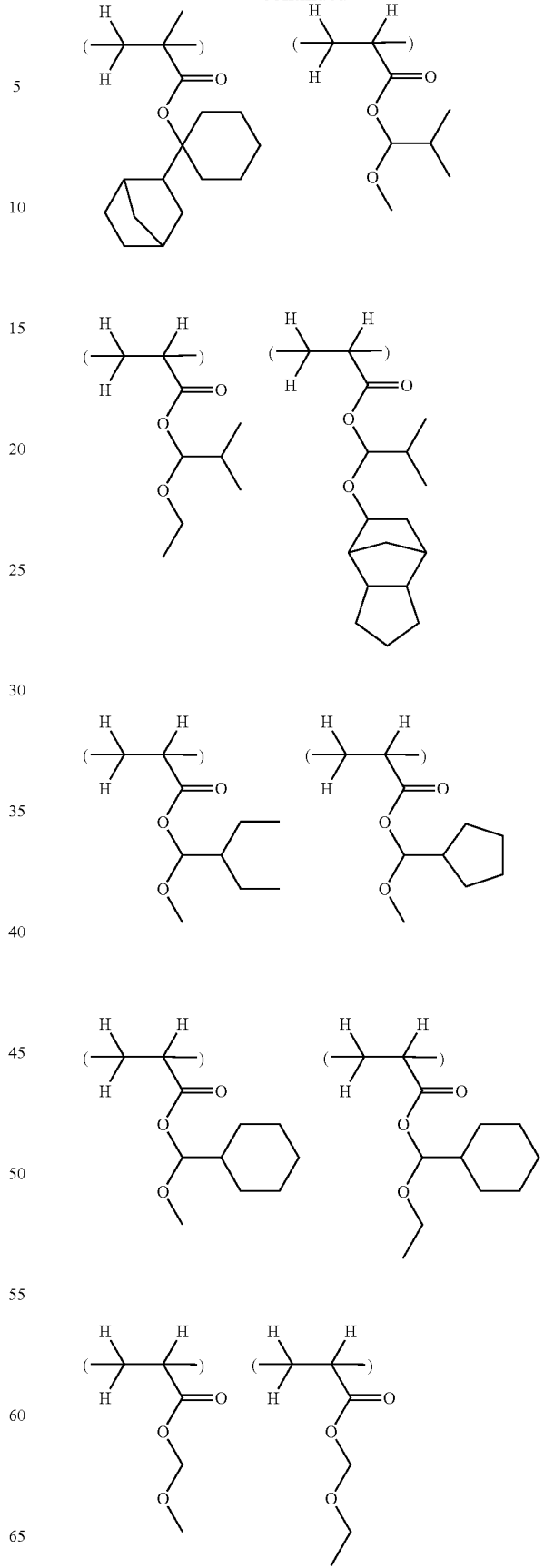

51
-continued
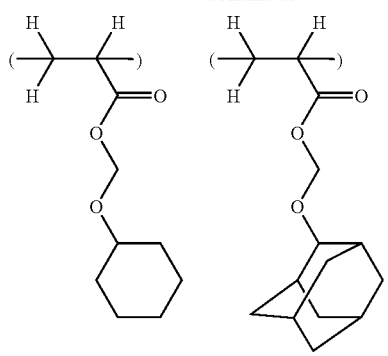
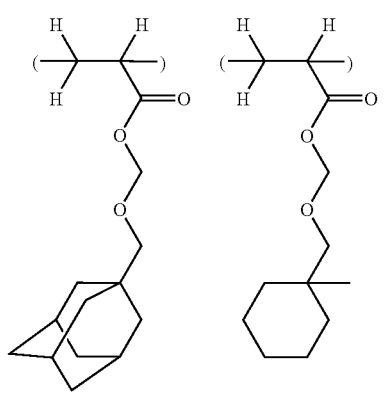
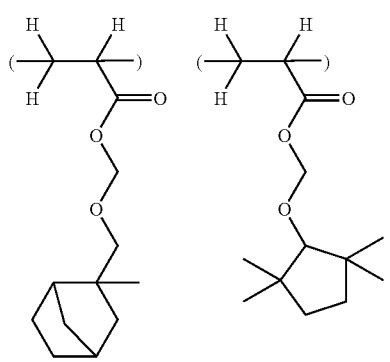
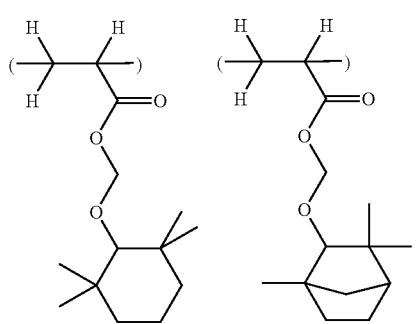
52
-continued
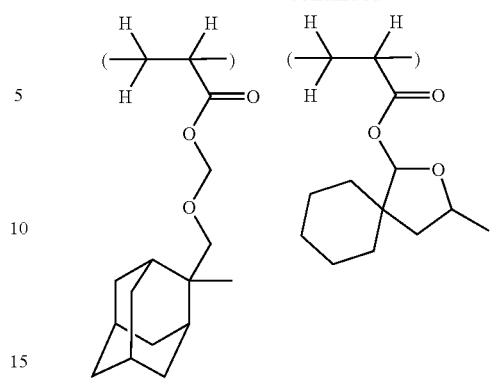
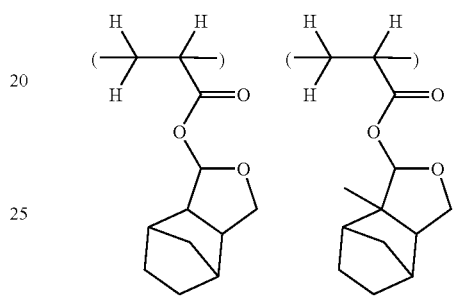
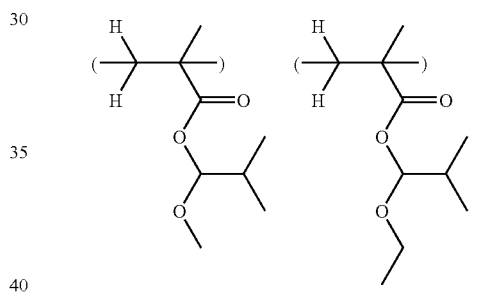
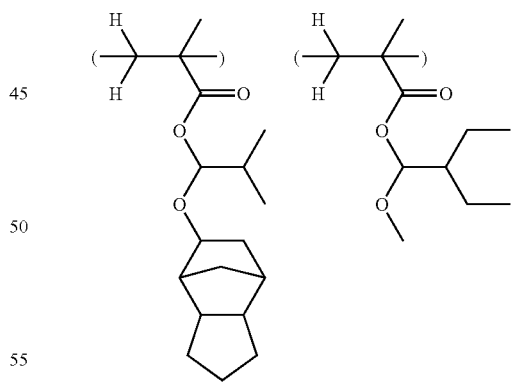
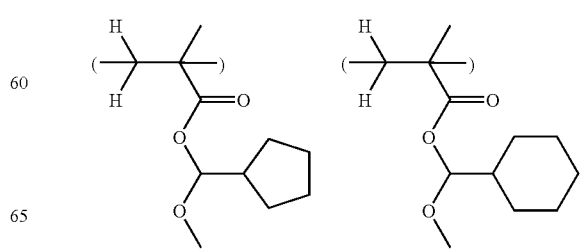

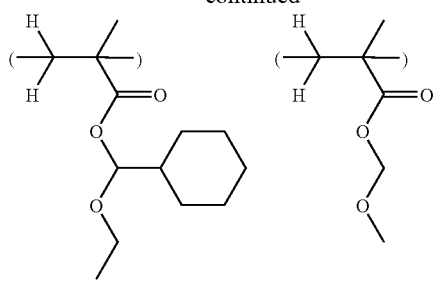
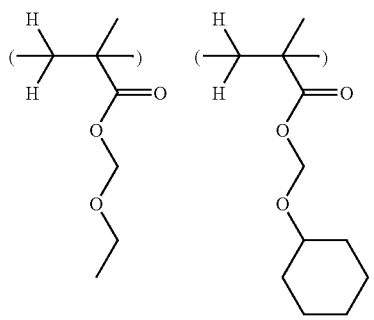
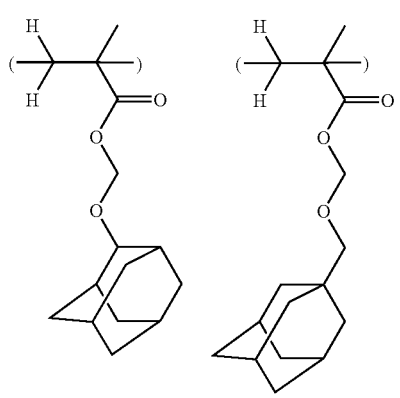
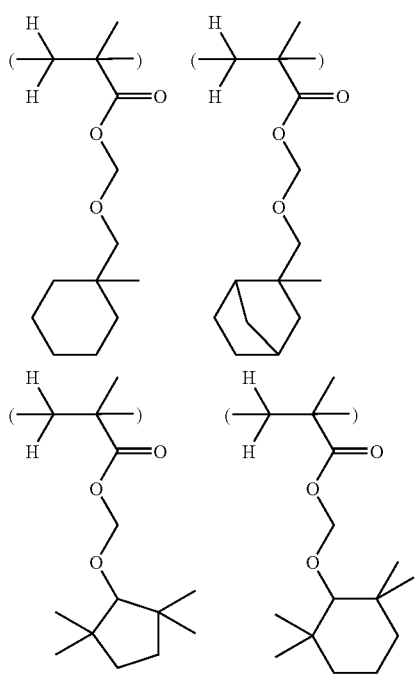
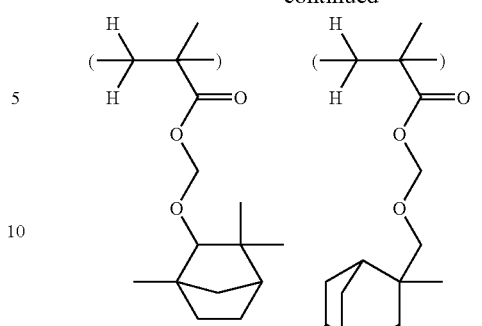
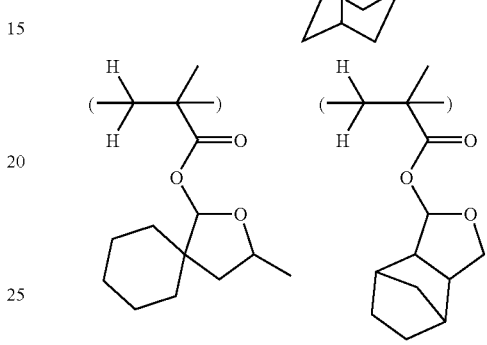
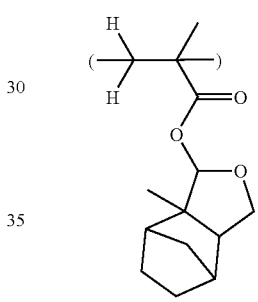
Illustrative, non-limiting examples of the recurring units of formula (4) are given below.
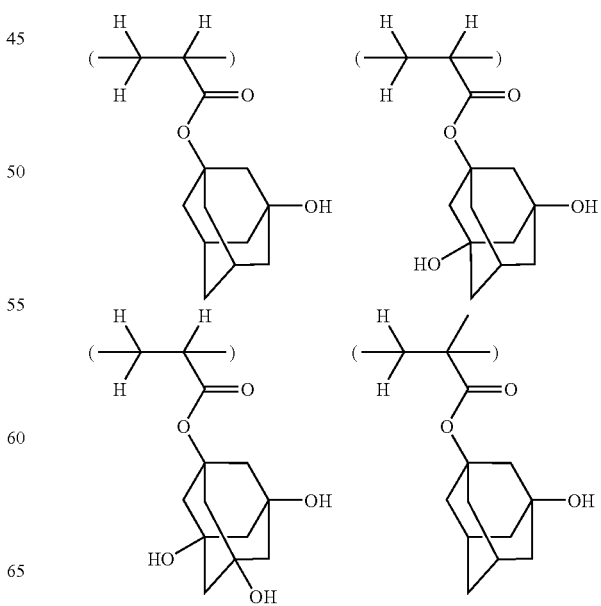

-continued
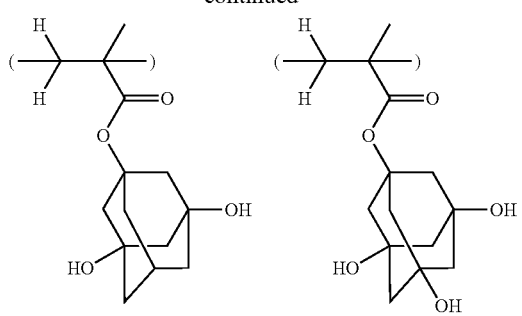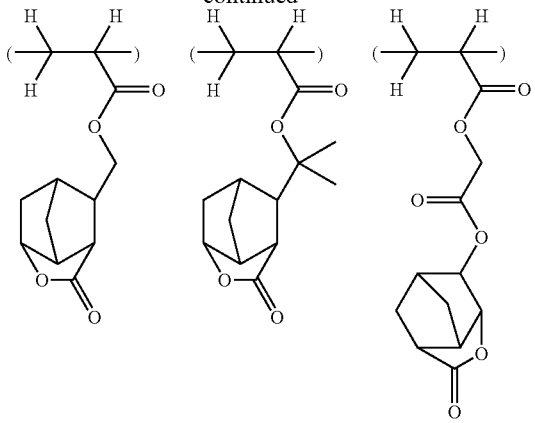
Illustrative, non-limiting examples of the recurring units of formula (5) are given below.
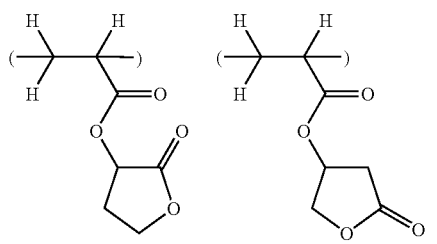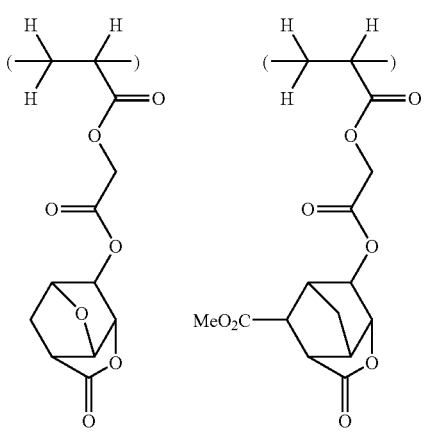
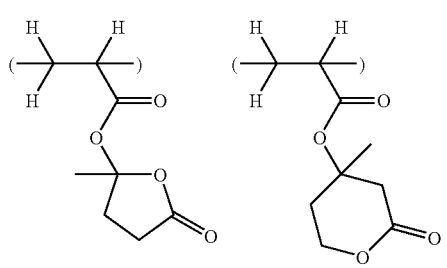
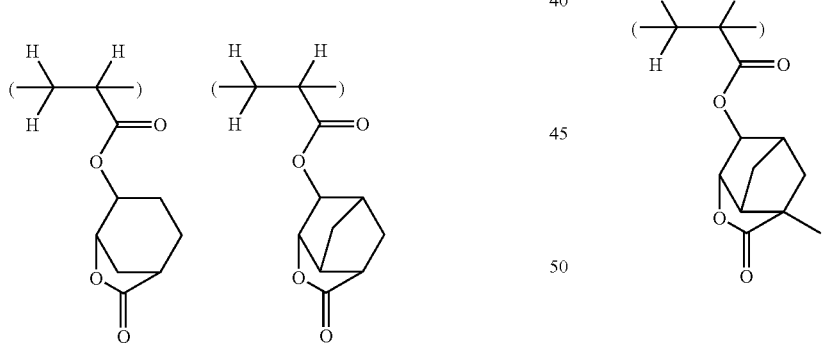
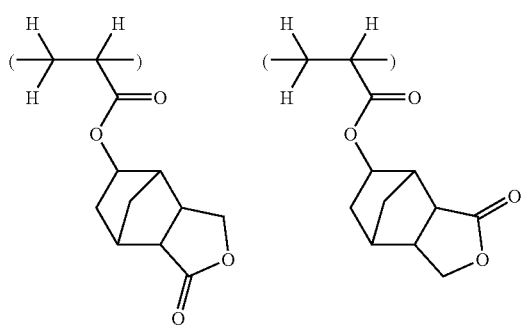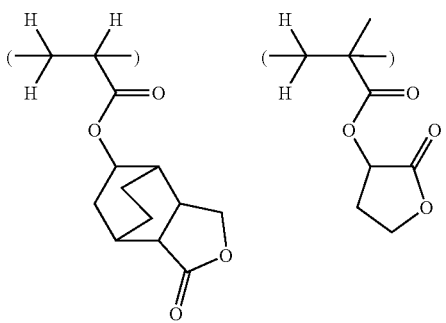

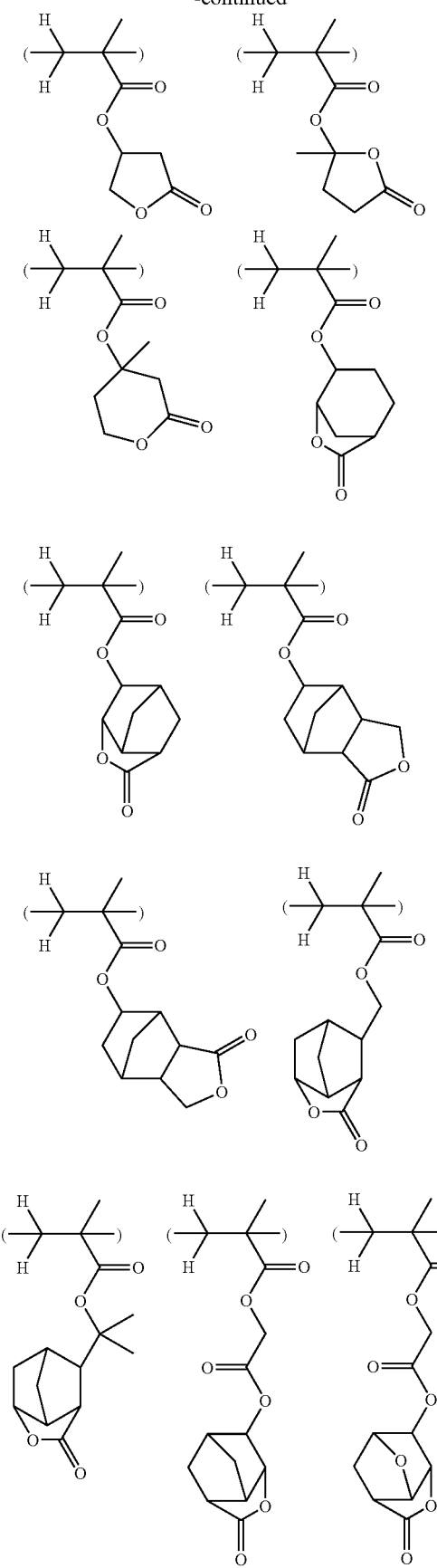
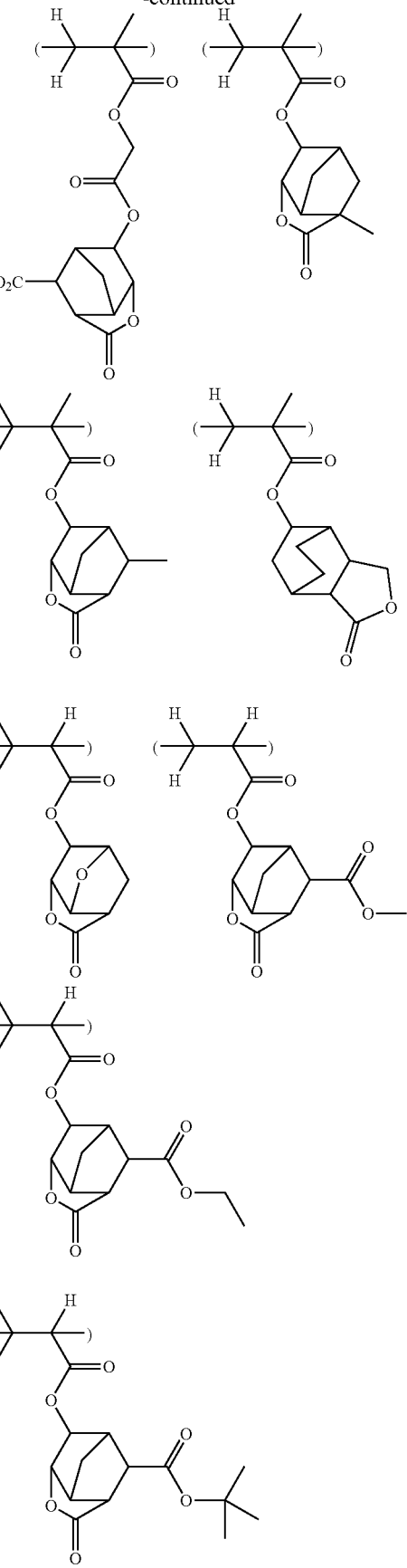

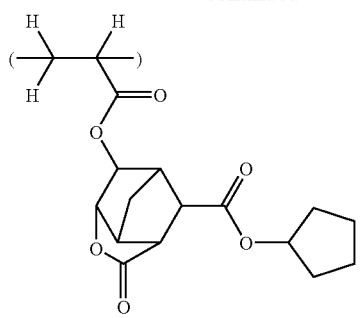
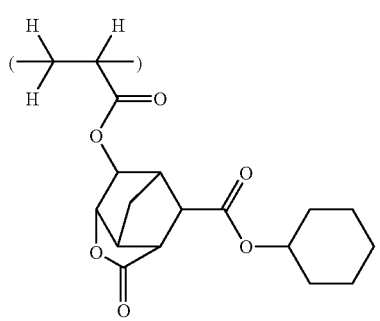
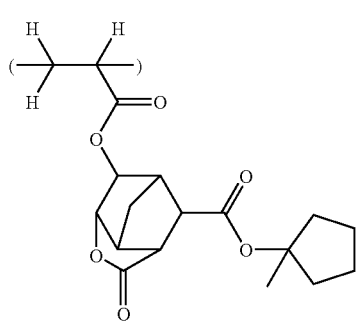
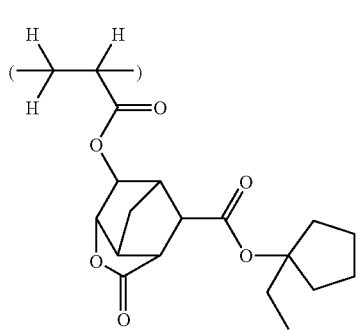
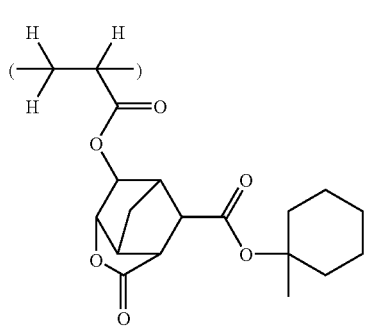
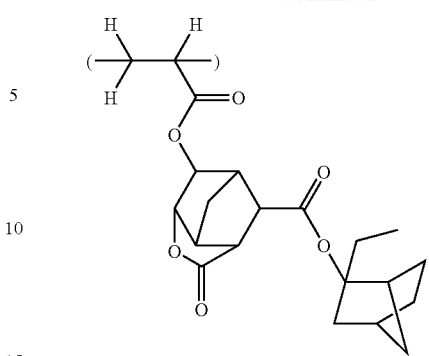
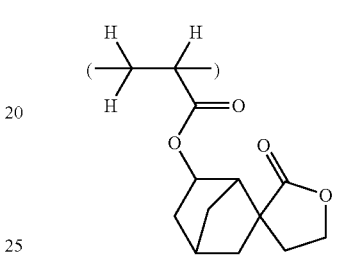
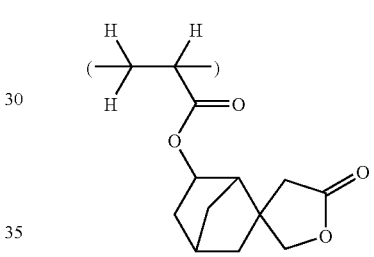
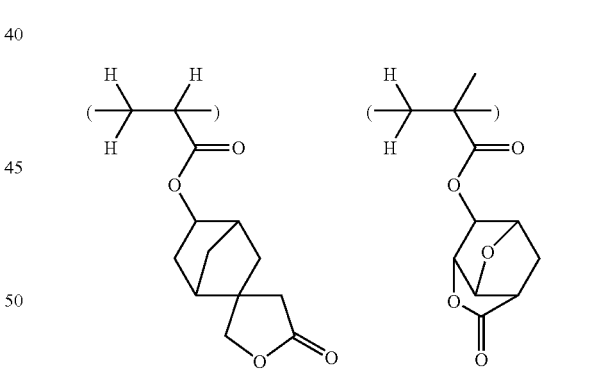
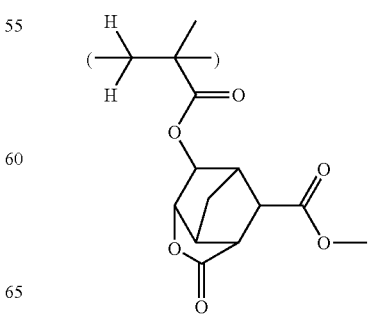

-continued
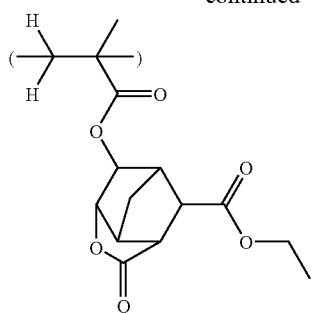
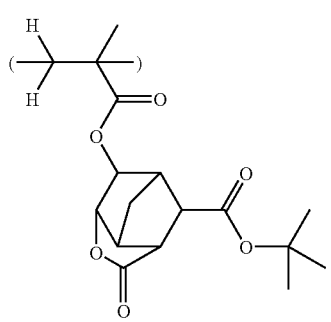
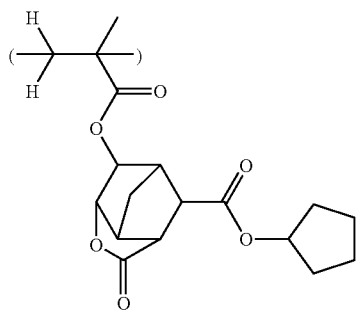
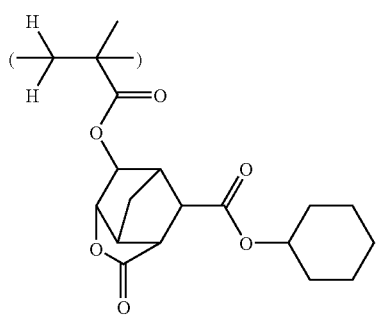
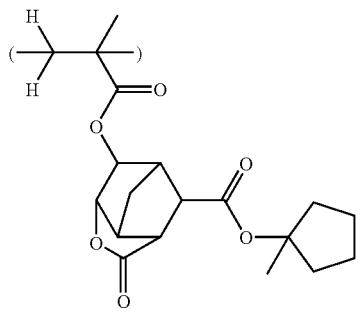
-continued
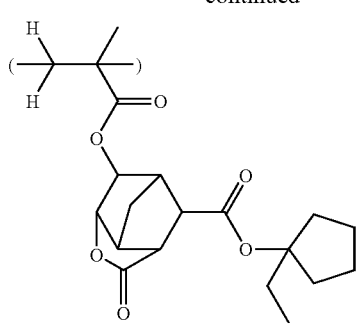
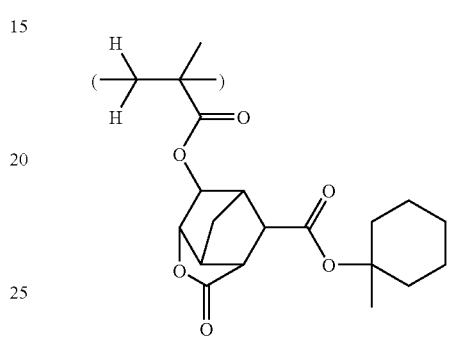
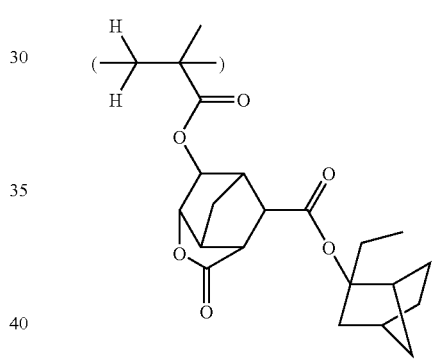
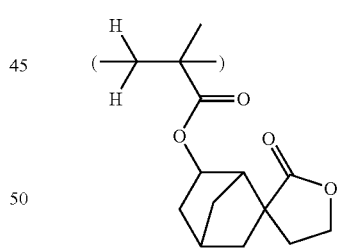
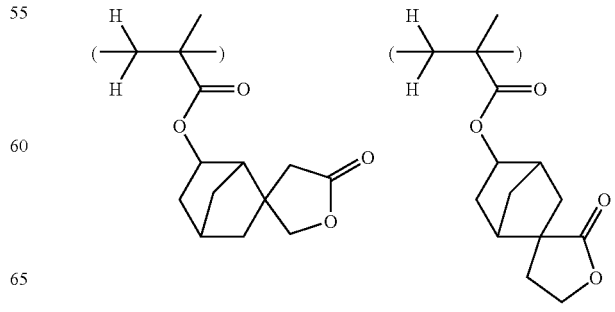

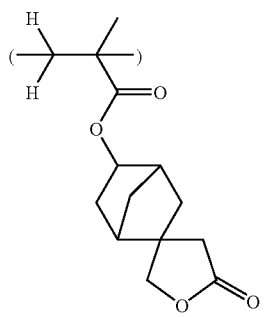
Illustrative, non-limiting examples of the recurring units of formula (6) are given below.
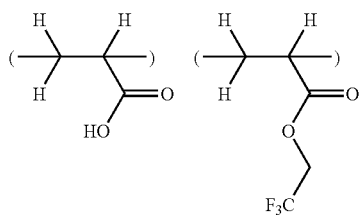
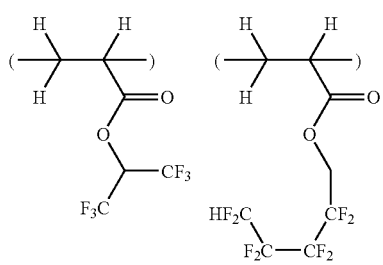
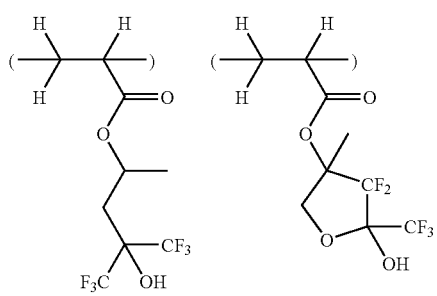
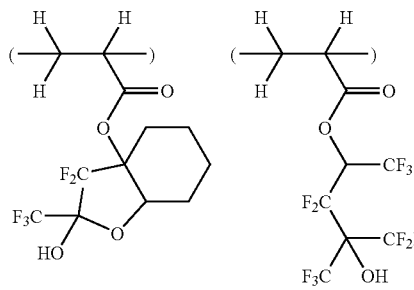
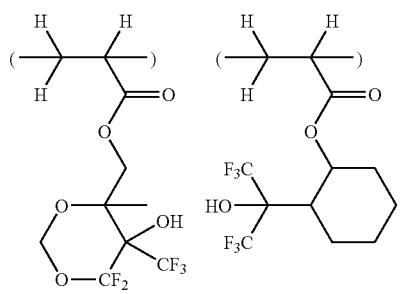
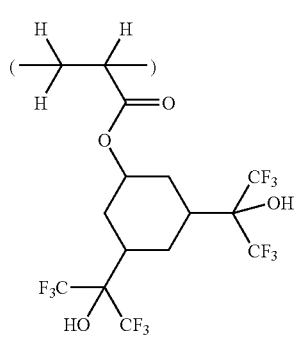
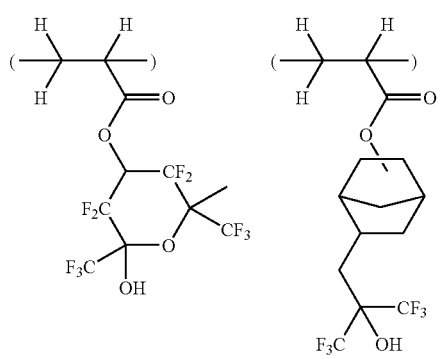
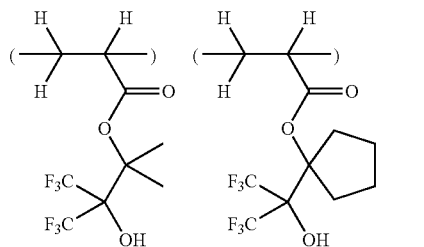
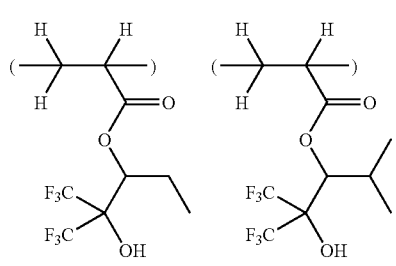

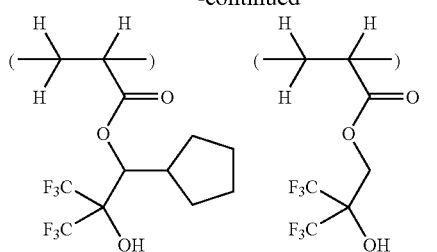
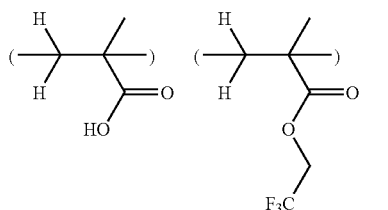
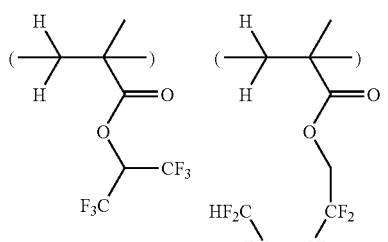
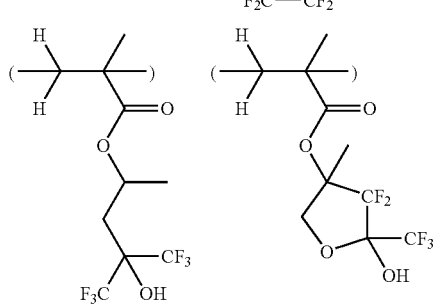
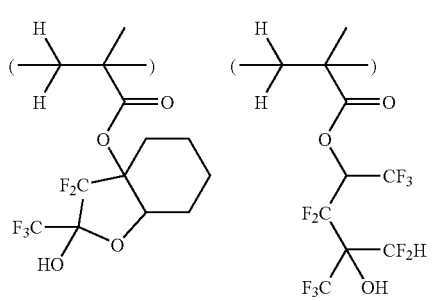
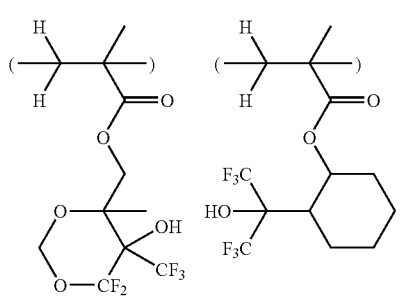

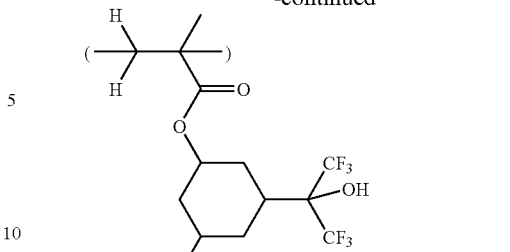
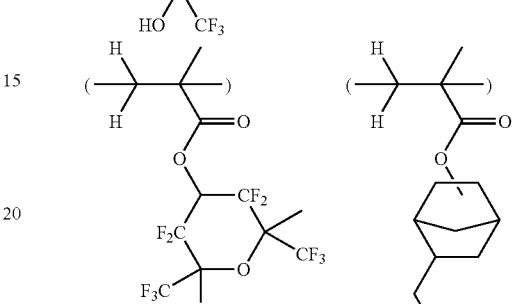
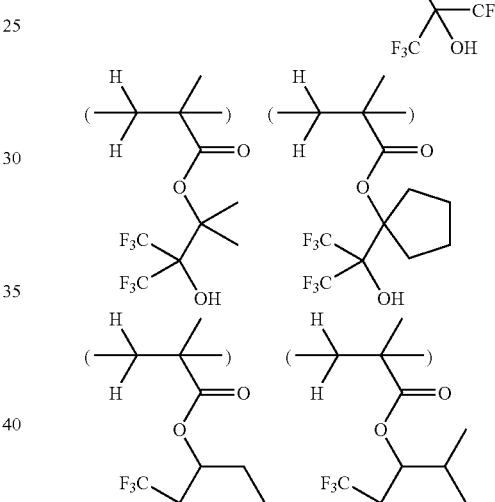
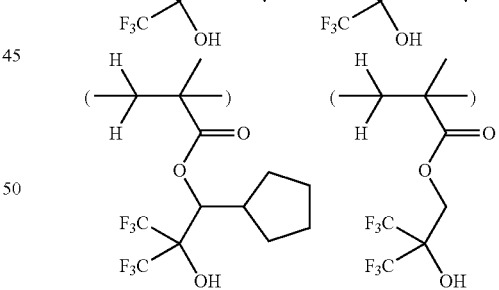

In addition to the foregoing units, the polymers of the invention may further comprise recurring units derived from monomers having a carbon-carbon double bond, for example, substituted acrylic acid esters such as methyl methacrylate, methyl chrotonate, dimethyl maleate and dimethyl itaconate, unsaturated carboxylic acids such as maleic acid, fumaric acid, and itaconic acid, cyclic olefins such as norbornene, norbornene derivatives, and tetracyclo[$4.4.0.1^{2,5}.17^{7,10}$] dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formulas (1a) to (1c) derived from monomers of formulas (1) and (2) in a porportion of more than 0 mol % to 100 mol %, preferably 5 to 70 mol %, and more preferably 10 to 50 mol %, (II) constituent units of one or more types having formulas (3) to (6) in a proportion of 0 mol % to less than 100 mol %, preferably 1 to 95 mol %, and more preferably 20 to 80 mol %, and (III) constituent units of one or more types derived from other monomers in a proportion of 0 to 80 mol %, αpreferably 0 to 70 mol %, and more preferably 0 to 50 mol %, based on the total moles of constituent units.

The polymers of the invention are prepared by copolymerization reaction using the compound of formula (1) or (2) as a first monomer and polymerizable double bond-bearing compounds as second and subsequent monomers.

The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the resist composition contains (A) the inventive polymer as a base resin, (B) an acid generator, (C) an organic solvent, and optionally (D) an organic nitrogen-containing compound and (E) a surfactant.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymers, and (iv) vinyl ether-maleic anhydride-(meth)acrylic acid derivative copolymers.

Of these the hydrogenated products of ring-opening metathesis polymers are synthesized by the method illustrated in JP-A 2003-66612. Illustrative examples of such hydrogenated polymers include those polymers having the recurring units shown below, but are not limited thereto.

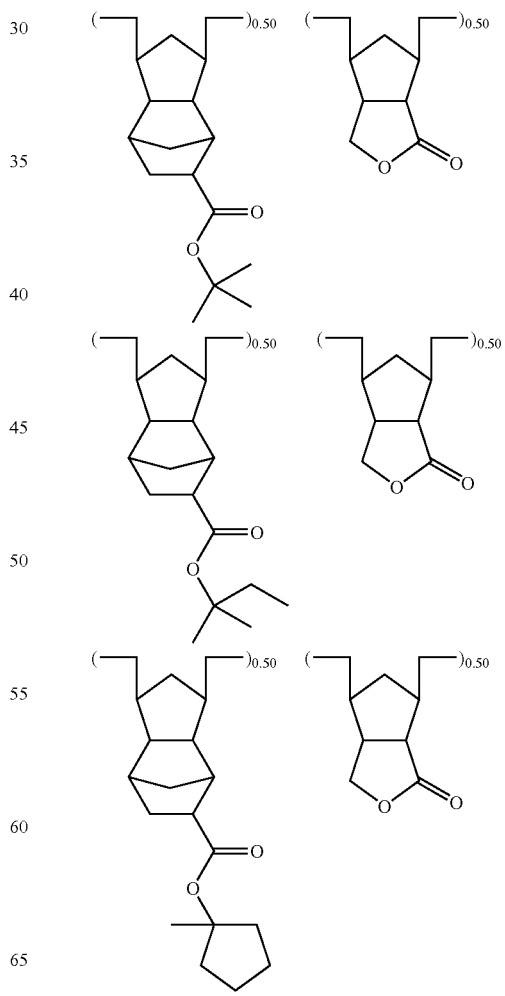

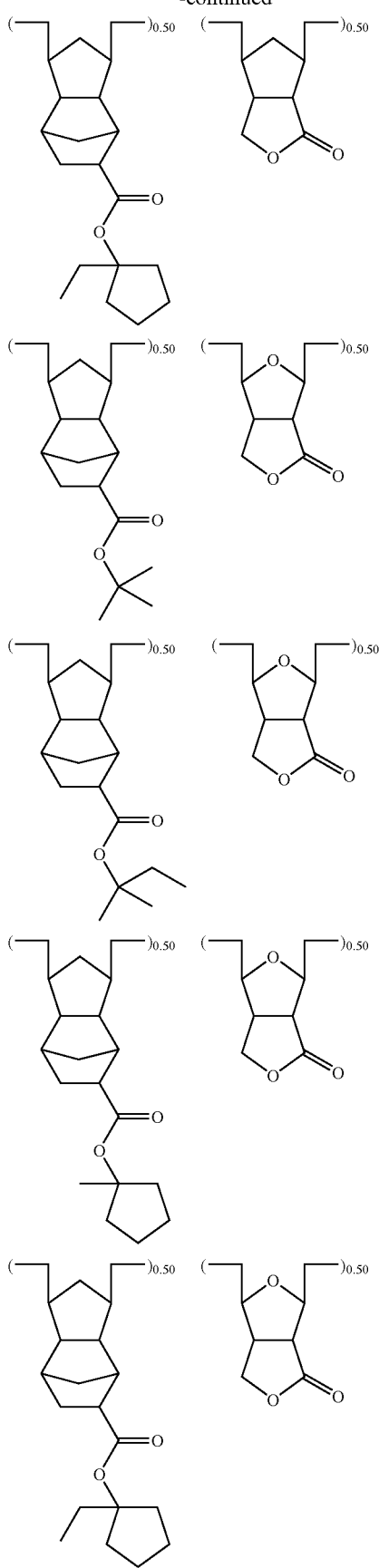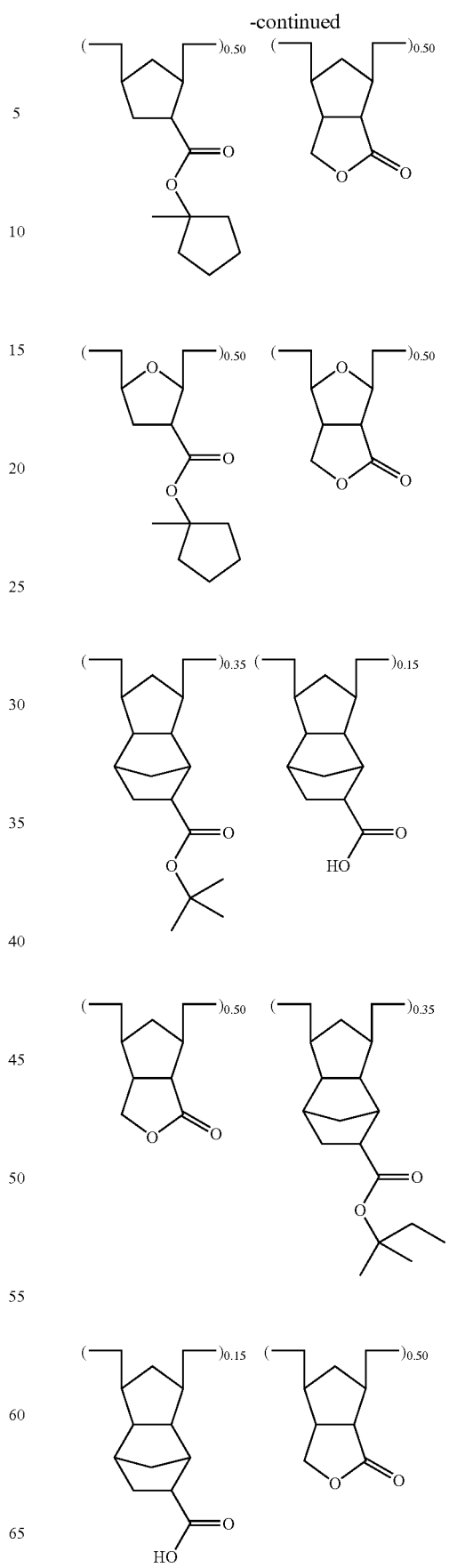

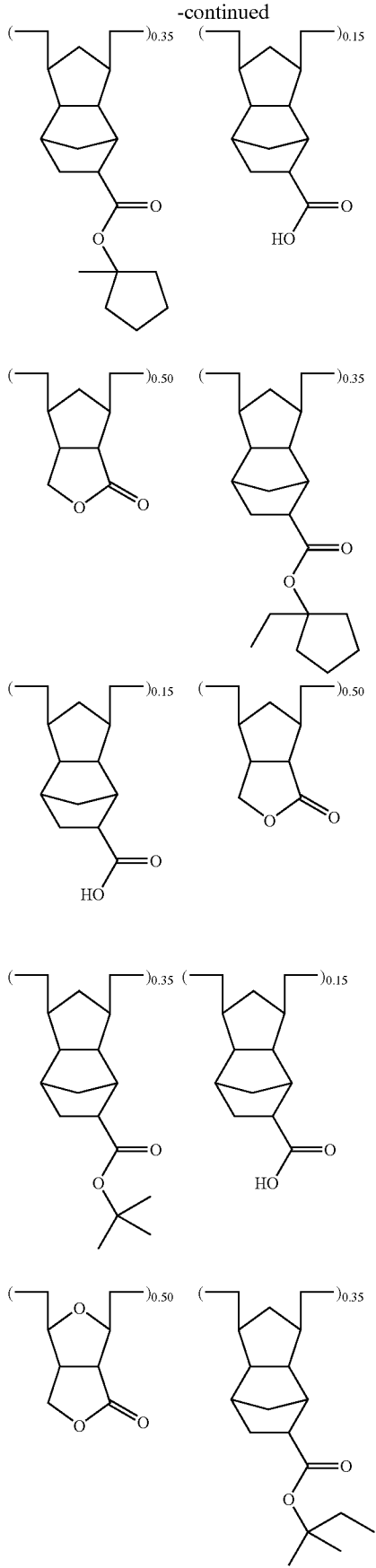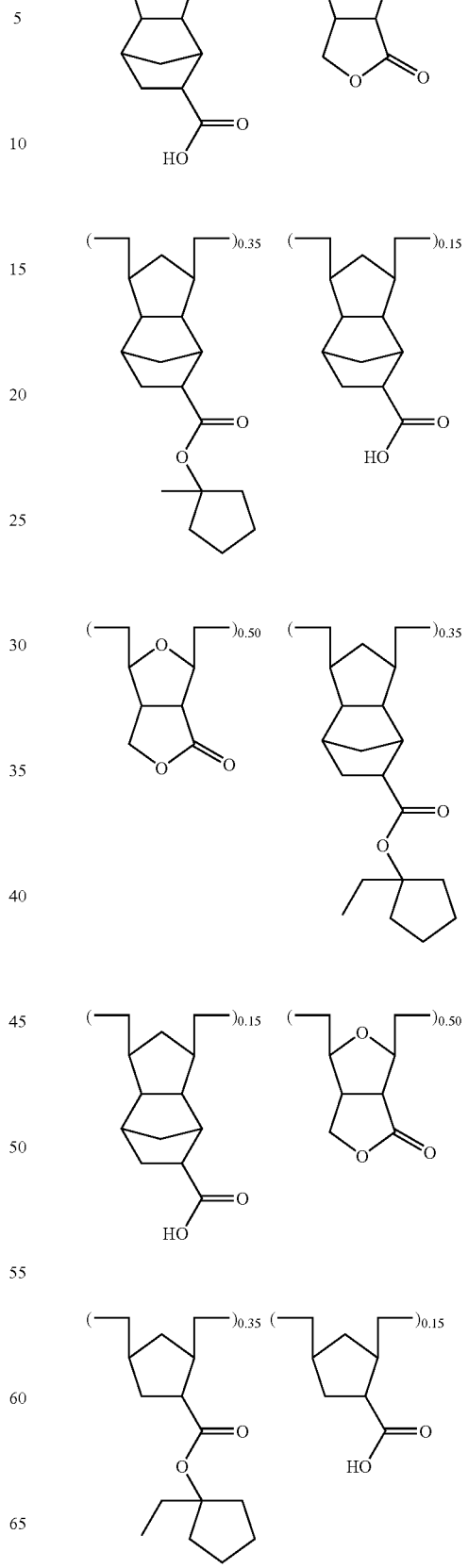

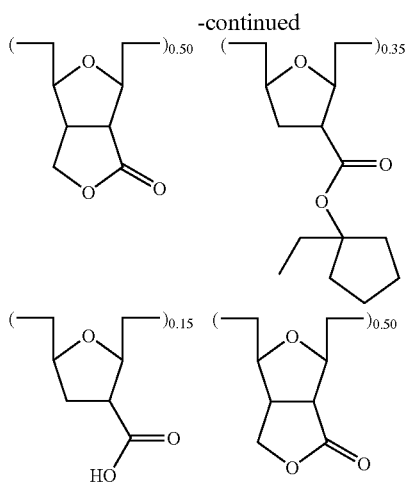

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Acid Generator

Typical of the acid generator (B) used herein is a photoacid generator (PAG). It is any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium,
(4-tert-butoxyphenyl)diphenylsulfonium,
bis(4-tert-butoxyphenyl)phenylsulfonium,
tris(4-tert-butoxyphenyl)sulfonium,
(3-tert-butoxyphenyl)diphenylsulfonium,
bis(3-tert-butoxyphenyl)phenylsulfonium,
tris(3-tert-butoxyphenyl)sulfonium,
(3,4-di-tert-butoxyphenyl)diphenylsulfonium,
bis(3,4-di-tert-butoxyphenyl)phenylsulfonium,
tris(3,4-di-tert-butoxyphenyl)sulfonium,
diphenyl(4-thiophenoxyphenyl)sulfonium,
(4-tert-butoxycarbonylmethyloxyphenyl)diphenylsulfonium,
tris(4-tert-butoxycarbonylmethyloxyphenyl)sulfonium,
(4-tert-butoxyphenyl)bis(4-dimethylaminophenyl)sulfonium,
tris(4-dimethylaminophenyl)sulfonium,
2-naphthyldiphenylsulfonium, dimethyl-2-naphthylsulfonium,
4-hydroxyphenyldimethylsulfonium,
4-methoxyphenyldimethylsulfonium, trimethylsulfonium,
2-oxocyclohexylcyclohexylmethylsulfonium,
trinaphthylsulfonium, tribenzylsulfonium,
diphenylmethylsulfonium, dimethylphenylsulfonium,
2-oxo-2-phenylethylthiacyclopentanium,
4-n-butoxynaphthyl-1-thiacyclopentanium, and
2-n-butoxynaphthyl-1-thiacyclopentanium.

Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(41-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafloropropanasulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl) ethanesulfonate.

Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo

[4.4.0.1$^{2,5}$.1$^{7,10}$]dodec-3-en-8-yl)ethanesulfonate.

Exemplary bis(substituted alkylsulfonyl)imides include bistrifluoromethylsulfonylimide, bispentafluoroethylsulfonylimide, bisheptafluoropropylsulfonylimide, and 1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bis-sulfonyldiazomethane compounds and sulfonyl-carbonyldiazomethane compounds such as
bis(ethylsulfonyl)diazomethane,
bis(1-methylpropylsulfonyl)diazomethane,
bis(2-methylpropylsulfonyl)diazomethane,
bis(1,1-dimethylethylsulfonyl)diazomethane,
bis(cyclohexylsulfonyl)diazomethane,
bis(perfluorcisopropylsulfonyl)diazomethane,
bis(phenylsulfonyl)diazomethane,
bis(4-methylphenylsulfonyl)diazomethane,
bis(2,4-dimethylphenylsulfonyl)diazomethane,
bis(2-naphthylsulfonyl)diazomethane,
bis(4-acetyloxyphenylsulfonyl)diazomethane,
bis(4-methanesulfonyloxyphenylsulfonyl)diazomethane,
bis(4-(4-toluenesulfonyloxy)phenylsulfonyl)diazomethane,
bis(4-(n-hexyloxy)phenylsulfonyl)diazomethane,
bis(2-methyl-4-(n-hexyloxy)phenylsulfonyl)diazomethane,
bis(2,5-dimethyl-4-(n-hexyloxy)phenylsulfonyl)diazomethane,
bis(3,5-dimethyl-4-(n-hexyloxy)phenylsulfonyl)diazomethane,
bis(2-methyl-5-isopropyl-4-(n-hexyloxy)phenylsulfonyl)diazomethane,
4-methylphenylsulfonylbenzoyldiazomethane,
tert-butylcarbonyl-4-methylphenylsulfonyldiazomethane,
2-naphthylsulfonylbenzoyldiazomethane,
4-methylphenylsulfonyl-2-naphthoyldiazomethane,
methylsulfonylbenzoyldiazomethane, and
tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo[2.2.1]-5-heptene-2,3-dicarboxylic acid imide. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate., 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8-yl)ethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucinol, catechol, resorcinol, and hydroquinone, in which all the hydroxyl groups are substituted by trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$.1$^{7,10}$]dodec-3-en-8 yl)ethanesulfonate.

Nitrobenzyl sulfonate photoacid generators include 2,4-dinitrobenzyl sulfonates, 2-nitrobenzyl sulfonates, and 2,6-dinitrobenzyl sulfonates, with exemplary sulfonates including trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3, 3-pentafluoro-2-tosyloxypropanesulfonate, 1,1-difluoro-2-naphthylethanesulfonate, 1,1,2,2-tetrafluoro-2-(norbornan-2-yl)ethanesulfonate, and 1,1,2,2-tetrafluoro-2-(tetracyclo[4.4.0.1$^{2,5}$. 1$^{7,10}$]dodec-3-en-8-yl)ethanesulfonate. Also useful are analogous nitrobenzyl sulfonate compounds in which the nitro group on the benzyl side is substituted by a trifluoromethyl group.

Sulfone photoacid generators include
bis(phenylsulfonyl)methane,
bis(4-methylphenylsulfonyl)methane,
bis(2-naphthylsulfonayl)methane,
2,2-bis(phenylsulfonyl)propane, 2,2-bis(4-methylphenylsulfonyl)propane,
2,2-bis(2-naphthylsulfonyl)propane,
2-methyl-2-(p-toluenesulfonyl)propiophenone,
2-cyclohexylcarbonyl-2-(p-toluenesulfonyl)propane, and
2,4-dimethyl-2-(p-toluenesulfonyl)pentan-3-one.

Photoacid generators in the form of glyoxime derivatives are described in Japanese Patent No. 2,906,999 and JP-A 9-301948 and include
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-O-(p-toluenesulfonyl)-2,3-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(methanesulfonyl)-α-dimethylglyoxime,
bis-O-(trifluoromethanesulfonyl)-α-dimethylglyoxime,
bis-O-(2,2,2-trifluoroethanesulfonyl)-α-dimethylglyoxime,
bis-O-(10-camphorsulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-trifluoromethylbenzenesulfonyl)-α-dimethylglyoxime,
bis-O-(xylenesulfonyl)-α-dimethylglyoxime,
bis-O-(trifluoromethanesulfonyl)-nioxime,
bis-O-(2,2,2-trifluoroethanesulfonyl)-nioxime,
bis-O-(10-camphorsulfonyl)-nioxime,
bis-O-(benzenesulfonyl)-nioxime,
bis-O-(p-fluorobenzenesulfonyl)-nioxime,
bis-O-(p-trifluoromethylbenzenesulfonyl)-nioxime, and
bis-O-(xylenesulfonyl)-nioxime.

Also included are the oxime sulfonates described in U.S. Pat. No. 6,004,724, for example,
(5-(4-toluenesulfonyl)oxyimino-5H-thiophen-2-ylidene)phenyl-acetonitrile,
(5-(10-camphorsulfonyl)oxyimino-5H-thiophen-2-ylidene)phenyl-acetonitrile,
(5-n-octanesulfonyloxyimino-5H-thiophen-2-ylidene)phenyl-acetonitrile,
(5-(4-toluenesulfonyl)oxyimino-5H-thiophen-2-ylidene)(2-methylphenyl)acetonitrile,
(5-(10-camphorsulfonyl)oxyimino-5H-thiophen-2-ylidene)(2-methylphenyl)acetonitrile,
(5-n-octanesulfonyloxyimino-5H-thiophen-2-ylidene)(2-methyl-phenyl) acetonitrile, etc. Also included are the oxime sulfonates described in U.S. Pat. No. 6,916,591, for example,
(5-(4-(4-toluenesulfonyloxy)benzenesulfonyl)oxyimino-5H-thiophen-2-ylidene)phenylacetonitrile and
(5-(2,5-bis(4-toluenesulfonyloxy)benzenesulfonyl)oxyimino-5H-thiophen-2-ylidene)phenylacetonitrile.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanoneoxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethyl-phenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethyl-phenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)sulfonate; 2,2,2-trifluoro-1-(4-methoxyphenyl)-ethanone oxime-O-octylsulfonate; 2,2,2-trifluoro-1-(4-thiomethylphenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethylphenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propylsulfonate; 2,2,2-trifluoro-1-[4-methylsulfonylphenyl]-ethanone oxime-O-propylsulfonate; 1,3-bis[1-(4-phenoxy-phenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propyl-sulfonate; 2,2,2-trifluoro-1-[4-methoxycarbonyl-methoxy-phenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; 2,2,2-trifluoro-1-[1-dioxa-thiophen-2-yl)]-ethanone oxime-O-propylsulfonate; 2,2,2-trifluoro-1-(4-(3-(4-(2,2,2-trifluoro-1-(trifluoromethanesulfonyloxy-imino)-ethyl)-phenoxy)-propoxy)-phenyl)ethanone oxime (trifluoromethanesulfonate); 2,2,2-trifluoro-1-(4-(3-(4-(2,2,2-trifluoro-1-(1-propanesulfonyloxyimino)-ethyl)-phenoxy)-propoxy)-phenyl)ethanone oxime(1-propanesulfonate); and 2,2,2-trifluoro-1-(4-(3-(4-(2,2,2-trifluoro-1-(1-butane-sulfonyloxyimino)-ethyl)-phenoxy)-propoxy)-phenyl)ethanone oxime(1-butanesulfonate). Also included are the oxime sulfonates described in U.S. Pat. No. 6,916,591, for example, 2,2,2-trifluoro-1-(4-(3-(4-(2,2,2-trifluoro-1-(4-(4-methyl-phenylsulfonyloxy)phenylsulfonyloxyimino)-ethyl)-phenoxy)-propoxy)-phenyl)ethanone oxime(4-(4-methylphenylsulfonyloxy)-phenylsulfonate) and 2,2,2-trifluoro-1-(4-(3-(4-(2,2,2-trifluoro-1-(2,5-bis(4-methylphenylsulfonyloxy)benzene-sultonyloxy)phenylsulfonyloxyimino)-ethyl)-phenoxy)-propoxy)-phenyl)ethanone oxime(2,5-bis(4-methylphenylsulfonyloxy)-benzenesulfonyloxy)phenylsulfonate).

Also included are the oxime sulfonates described in JP-A 9-95479 and JP-A 9-230588 and the references cited therein, for example, α-(p-toluenesulfonyloxyimino)-phenylacetonitrile,
α-(p-chlorobenzenesulfonyloxyimino)-phenylacetonitrile,
α-(4-nitrobenzenesulfonyloxyimino)-phenylacetonitrile,
α-(4-nitro-2-trifluoromethylbenzenesulfonyloxyimino)-phenylacetonitrile,
α-(benzenesulfonyloxyimino)-4-chlorophenylacetonitrile,
α-(benzenesulfonyloxyimino)-2,4-dichlorophenylacetonitrile,
α-(benzenesulfonyloxyimino)-2,6-dichlorophenylacetonitrile,
α-(benzenesulfonyloxyimino)-4-methoxyphenylacetonitrile,
α-(2-chlorobenzenesulfonyloxyimino)-4-methoxyphenylacetonitrile,
α-(benzenesulfonyloxyimino)-2-thienylacetonitrile,
α-(4-dodecylbenzenesulfonyloxyimino)-phenylacetonitrile,
α-[(4-toluenesulfonyloxyimino)-4-methoxyphenyl]acetonitrile,
α-[(dodecylbenzenesulfonyloxyimino)-4-methoxyphenyl] acetonitrile,
α-(tosyloxyimino)-3-thienylacetonitrile,
α-(methylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile, and
α-(n-butylsulfonyloxyimino)-1-cyclohexenylacetonitrile.

Also included are oxime sulfonates having the formula:

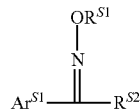

wherein $R^{s1}$ is a substituted or unsubstituted haloalkylsulfonyl or halobenzenesulfonyl group of 1 to 10 carbon atoms, $R^{s2}$ is a haloalkyl group of 1 to 11 carbon atoms, and $Ar^{s1}$ is substituted or unsubstituted aromatic or hetero-aromatic group, as described in WO 2004/074242. Examples include
2-[2,2,3,3,4,4,5,5-octafluoro-1-(nonafluorobutylsulfonyloxyimino)-pentyl]-fluorene,
2-[2,2,3,3,4,4-pentafluoro-1-(nonafluorobutylsulfonyloxy-imino)-butyl]-fluorene,
2-[2,2,3,3,4,4,5,5,6,6-decafluoro-1-(nonafluorobutylsulfonyl-oxyimino)-hexyl]-fluorene,
2-[2,2,3,3,4,4,5,5-octafluoro-1-(nonafluorobutylsulfonyloxy-imino)- pentyl]-4-biphenyl,
2-[2,2,3,3,4,4-pentafluoro-1-(nonafluorobutylsulfonyloxy-imino)-butyl]-4-biphenyl, and
2-[2,2,3,3,4,4,5,5,6,6-decafluoro-1-(nonafluorobutylsulfonyl-oxyimino)-hexyl]-4-biphenyl.

Suitable bisoxime sulfonates include those described in JP-A 9-208554, for example,
bis(α-(4-toluenesulfonyloxy)imino)-p-phenylenediacetonitrile,
bis(α-(benzenesulfonyloxy)imino)-p-phenylenediacetonitrile,
bis(α-(methanesulfonyloxy)imino)-p-phenylenediacetonitrile,
bis(α-(butanesulfonyloxy)imino)-p-phenylenediacetonitrile,
bis(α-(10-camphorsulfonyloxy)imino)-p-phenylenediacetonitrile,
bis(α-(4-toluenesulfonyloxy)imino)-p-phenylenediacetonitrile,
bis(α-(trifluoromethanesulfonyloxy)imino)-p-phenylenediacetonitrile,
bis(α-(4-methoxybenzenesulfonyloxy)imino)-p-phenylenediacetonitrile,
bis(α-(4-toluenesulfonyloxy)imino)-m-phenylenediacetonitrile,
bis(α-(benzenesulfonyloxy)imino)-m-phenylenediacetonitrile,
bis(α-(methanesulfonyloxy)imino)-m-phenylenediacetonitrile,
bis(α-(butanesulfonyloxy)imino)-m-phenylenediacetonitrile,
bis(α-(10-camphorsulfonyloxy)imino)-m-phenylenediacetonitrile,
bis(α-(4-toluenesulfonyloxy)imino)-m-phenylenediacetonitrile,
bis(α-(trifluoromethanesulfonyloxy)imino)-m-phenylenediacetonitrile,
bis(α-(4-methoxybenzenesulfonyloxy)imino)-m-phenylenediacetonitrile, etc.

Of these, preferred photoacid generators are sulfonium salts, bissulfonyldiazomethanes, N-sulfonyloxyimides, oxime-O-sulfonates and glyoxime derivatives. More preferred photoacid generators are sulfonium salts, bissulfonyldiazomethanes, N-sulfonyloxyimides, and oxime-O-sulfonates. Typical examples include
triphenylsulfonium p-toluenesulfonate,
triphenylsulfonium camphorsulfonate,
triphenylsulfonium pentafluorobenzenesulfonate, triphenylsulfonium nonafluorobutanesulfonate,
triphenylsulfonium 4-(4'-toluenesulfonyloxy)benzenesulfonate,
triphenylsulfonium 2,4,6-triisopropylbenzenesulfonate,
4-tert-butoxyphenyldiphenylsulfonium p-toluenesulfonate,
4-tert-butoxyphenyldiphenylsulfonium camphorsulfonate,
4-tert-butoxyphenyldiphenylsulfonium 4(4'-toluenesulfonyl-oxy)benzenesulfonate,
tris(4-methylphenyl)sulfonium camphorsulfonate,
tris(4-tert-butylphenyl)sulfonium camphorsulfonate,
4-tert-butylphenyldiphenylsulfonium camphorsulfonate,
4-tert-butylphenyldiphenylsulfonium nonafluoro-1-butanesulfonate,
4-tert-butylphenyldiphenylsulfonium pentafluoroethyl-perfluorocyclohexanesulfonate,
4-tert-butylphenyldiphenylsulfonium perfluoro-1-octanesulfonate,
triphenylsulfonium 1,1-difluoro-2-naphthyl-ethanesulfonate,
triphenylsulfonium 1,1,2,2-tetrafluoro-2-(norbornan-2-yl)-ethanesulfonate,
bis(tert-butylsulfonyl)diazomethane,
bis(cyclohexylsulfonyl)diazomethane,
bis(2,4-dimethylphenylsulfonyl)diazomethane,
bis(4-(n-hexyloxy)phenylsulfonyl)diazomethane,
bis(2-methyl-4-(n-hexyloxy)phenylsulfonyl)diazomethane,
bis(2,5-dimethyl-4-(n-hexyloxy)phenylsulfonyl)diazomethane,
bis(3,5-dimethyl-4-(n-hexyloxy)phenylsulfonyl)diazomethane,
bis(2-methyl-5-isopropyl-4-(n-hexyloxy)phenylsulfonyl)diazo-methane,
bis(4-tert-butylphenylsulfonyl)diazomethane,
N-camphorsulfonyloxy-5-norbornene-2,3-dicarboxylic acid imide,
N-p-toluenesulfonyloxy-5-norbornene-2,3-dicarboxylic acid imide,
2-[2,2,3,3,4,4,5,5-octafluoro-1-(nonafluorobutylsulfonyloxy-imino)-pentyl]-fluorene,
2-[2,2,3,3,4,4-pentafluoro-1-(nonafluorobutylsulfonyloxy-imino)-butyl]-fluorene, and
2-[2,2,3,3,4,4,5,5,6,6-decafluoro-1-(nonafluorobutylsulfonyl-oxyimino)-hexyl]-fluorene.

In the resist composition, an appropriate amount of the photoacid generator is, but not limited to, 0.1 to 20 parts, and especially 0.1 to 10 parts by weight per 100 parts by weight of the base resin. Too high a proportion of the photoacid generator may give rise to problems of degraded resolution and foreign matter upon development and resist film peeling. The photoacid generators may be used alone or in admixture of two or more. The transmittance of the resist film can be controlled by using a photoacid generator having a low transmittance at the exposure wavelength and adjusting the amount of the photoacid generator added.

In the resist composition, there may be added a compound which is decomposed with an acid to generate an acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is about 200 to 1,000 parts, especially about 400 to 800 parts by weight per 100 parts by weight of the base resin in the resist composition.

Nitrogen-Containing Compound

In the resist composition, an organic nitrogen-containing compound or compounds (D) may be compounded. The organic nitrogen-containing compound used herein is preferably a compound capable of suppressing the rate of diffusion when the acid generated by the acid generator diffuses within the resist film. The inclusion of this type of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

In addition, organic nitrogen-containing compounds of the following general formula (B)-1 may also be included alone or in admixture.

$$N(X)_n(Y)_{3-n} \quad (B)\text{-}1$$

In the formula, n is equal to 1, 2 or 3; side chain Y is independently hydrogen or a straight, branched or cyclic $C_1$-$C_{20}$ alkyl group which may contain an ether or hydroxyl group; and side chain X is independently selected from groups of the following general formulas (X)-1 to (X)-3, and two or three X's may bond together to form a ring.

$$-[R^{300}-O-R^{301}] \quad (X)\text{-}1$$

$$-[R^{302}-O-R^{303}-\underset{\underset{O}{\|}}{C}-R^{304}] \quad (X)\text{-}2$$

$$-[R^{305}-\underset{\underset{O}{\|}}{C}-O-R^{306}] \quad (X)\text{-}3$$

In the formulas, $R^{300}$, $R^{302}$ and $R^{305}$ are independently straight or branched $C_1$-$C_4$ alkylene groups; $R^{301}$ and $R^{304}$ are independently hydrogen, straight, branched or cyclic $C_1$-$C_{20}$ alkyl groups, which may contain at least one hydroxyl, ether, ester group or lactone ring; $R^{303}$ is a single bond or a straight or branched $C_1$-$C_4$ alkylene group; and $R^{306}$ is a straight, branched or cyclic $C_1$-$C_{20}$ alkyl group, which may contain at least one hydroxyl, ether, ester group or lactone ring.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine,
tris[2-(2-oxopropoxy)ethyl]amine,
tris[2-(methoxycarbonylmethyl)oxyethyl]amine,
tris[2-(tert-butoxycarbonylmethyloxy)ethyl]amine,
tris[2-(cyclohexyloxycarbonylmethyloxy)ethyl]amine,
tris(2-methoxycarbonylethyl)amine,
tris(2-ethoxycarbonylethyl)amine,
N,N-bis(2-hydroxyethyl)-2-(methoxycarbonyl)ethylamine,
N,N-bis(2-acetoxyethyl)-2-(methoxycarbonyl)ethylamine,
N,N-bis(2-hydroxyethyl)-2-(ethoxycarbonyl)ethylamine,
N,N-bis(2-acetoxyethyl)-2-(ethoxycarbonyl)ethylamine,
N,N-bis(2-hydroxyethyl)-2-(2-methoxyethoxycarbonyl)ethylamine,
N,N-bis(2-acetoxyethyl)-2-(2-methoxyethoxycarbonyl)ethylamine,
N,N-bis(2-hydroxyethyl)-2-(2-hydroxyethoxycarbonyl)ethylamine,
N,N-bis(2-acetoxyethyl)-2-(2-acetoxyethoxycarbonyl)ethylamine,
N,N-bis(2-hydroxyethyl)-2-[(methoxycarbonyl)methoxycarbonyl]-ethylamine,
N,N-bis(2-acetoxyethyl)-2-[(methoxycarbonyl)methoxycarbonyl]-ethylamine,
N,N-bis(2-hydroxyethyl)-2-(2-oxopropoxycarbonyl)ethylamine,
N,N-bis(2-acetoxyethyl)-2-(2-oxopropoxycarbonyl)ethylamine,
N,N-bis(2-hydroxyethyl)-2-(tetrahydrofurfuryloxycarbonyl)-ethylamine,
N,N-bis(2-acetoxyethyl)-2-(tetrahydrofurfuryloxycarbonyl)-ethylamine,
N,N-bis(2-hydroxyethyl)-2-[(2-oxotetrahydrofuran-3-yl)oxy-carbonyl]ethylamine,
N,N-bis(2-acetoxyethyl)-2-[(2-oxotetrahydrofuran-3-yl)oxy-carbonyl]ethylamine,
N,N-bis(2-hydroxyethyl)-2-(4-hydroxybutoxycarbonyl)ethylamine,
N,N-bis(2-formyloxyethyl)-2-(4-formyloxybutoxycarbonyl)-ethylamine,
N,N-bis(2-formyloxyethyl)-2-(2-formyloxyethoxycarbonyl)-ethylamine,
N,N-bis(2-methoxyethyl)-2-(methoxycarbonyl)ethylamine,
N-(2-hydroxyethyl)-bis[2-(methoxycarbonyl)ethyl]amine,
N-(2-acetoxyethyl)-bis[2-(methoxycarbonyl)ethyl]amine,
N-(2-hydroxyethyl)-bis[2-(ethoxycarbonyl)ethyl]amine,
N-(2-acetoxyethyl)-bis[2-(ethoxycarbonyl)ethyl]amine,
N-(3-hydroxy-1-propyl)-bis[2-(methoxycarbonyl)ethyl]amine,
N-(3-acetoxy-1-propyl)-bis[2-(methoxycarbonyl)ethyl]amine,
N-(2-methoxyethyl)-bis[2-(methoxycarbonyl)ethyl]amine,
N-butyl-bis[2-(methoxycarbonyl)ethyl]amine,
N-butyl-bis[2-(2-methoxyethoxycarbonyl)ethyl]amine,
N-methyl-bis(2-acetoxyethyl)amine,
N-ethyl-bis(2-acetoxyethyl)amine,
N-methyl-bis(2-pivaloyloxyethyl)amine,
N-ethyl-bis[2-(methoxycarbonyloxy)ethyl]amine,
N-ethyl-bis[2-(tert-butoxycarbonyloxy)ethyl]amine,
tris(methoxycarbonylmethyl)amine,
tris(ethoxycarbonylmethyl)amine,
N-butyl-bis(methoxycarbonylmethyl)amine,
N-hexyl-bis(methoxycarbonylmethyl)amine, and
β-(diethylamino)-δ-valerolactone.

Also useful are one or more organic nitrogen-containing compounds having cyclic structure represented by the following general formula (B)-2.

Herein X is as defined above, and $R^{307}$ is a straight or branched alkylene group of 2 to 20 carbon atoms which may contain one or more carbonyl, ether, ester or sulfide groups.

Illustrative examples of the organic nitrogen-containing compounds having formula (B)-2 include
1-[2-(methoxymethoxy)ethyl]pyrrolidine,
1-[2-(methoxymethoxy)ethyl]piperidine,
4-[2-(methoxymethoxy)ethyl]morpholine,
1-[2-[(2-methoxyethoxy)methoxy]ethyl]pyrrolidine,
1-[2-[(2-methoxyethoxy)methoxy]ethyl]piperidine,
4-[2-[(2-methoxyethoxy)methoxy]ethyl]morpholine,
2-(1-pyrrolidinyl)ethyl acetate, 2-piperidinoethyl acetate,
2-morpholinoethyl acetate, 2-(1-pyrrolidinyl)ethyl formate,
2-piperidinoethyl propionate,
2-morpholinoethyl acetoxyacetate,
2-(1-pyrrolidinyl)ethyl methoxyacetate,
4-[2-(methoxycarbonyloxy)ethyl]morpholine,
1-[2-(t-butoxycarbonyloxy)ethyl]piperidine,
4-[2-(2-methoxyethoxycarbonyloxy)ethyl]morpholine,
methyl 3-(1-pyrrolidinyl)propionate,
methyl 3-piperidinopropionate, methyl 3-morpholinopropionate,
methyl 3-(thiomorpholino)propionate,
methyl 2-methyl-3-(1-pyrrolidinyl)propionate,
ethyl 3-morpholinopropionate,
methoxycarbonylmethyl 3-piperidinopropionate,
2-hydroxyethyl 3-(1-pyrrolidinyl)propionate,
2-acetoxyethyl 3-morpholinopropionate,
2-oxotetrahydrofuran-3-yl 3-(1-pyrrolidinyl)propionate,
tetrahydrofurfuryl 3-morpholinopropionate,
glycidyl 3-piperidinopropionate,
2-methoxyethyl 3-morpholinopropionate,
2-(2-methoxyethoxy)ethyl 3-(1-pyrrolidinyl)propionate,
butyl 3-morpholinopropionate,
cyclohexyl 3-piperidinopropionate,
α-(1-pyrrolidinyl)methyl-γ-butyrolactone,
β-piperidino-γ-butyrolactone, β-morpholino-δ-valerolactone,
methyl 1-pyrrolidinylacetate, methyl piperidinoacetate,
methyl morpholinoacetate, methyl thiomorpholinoacetate,
ethyl 1-pyrrolidinylacetate, 2-methoxyethyl morpholinoacetate,
2-morpholinoethyl 2-methoxyacetate,
2-morpholinoethyl 2-(2-methoxyethoxy)acetate,
2-morpholinoethyl 2-[2-(2-methoxyethoxy)ethoxy]acetate,
2-morpholinoethyl hexanoate, 2-morpholinoethyl octanoate,
2-morpholinoethyl decanoate, 2-morpholinoethyl laurate,
2-morpholinoethyl myristate, 2-morpholinoethyl palmitate, and
2-morpholinoethyl stearate.

Also, one or more organic nitrogen-containing compounds having cyano group represented by the following general formulae (B)-3 to (B)-6 may be blended.

$$(X)_{3-n}-N-(R^{308}-CN)_n \qquad \text{(B)-3}$$

-continued

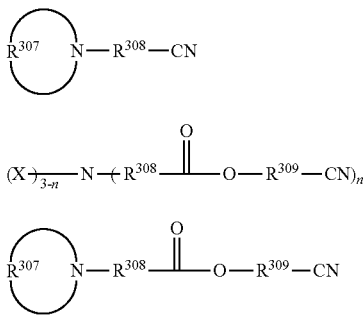

Herein, X, $R^{307}$ and n are as defined above, and $R^{308}$ and $R^{309}$ are each independently a straight or branched $C_1$-$C_4$ alkylene group.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate., cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds having an imidazole structure and a polar functional group, represented by the general formula (B)-7.

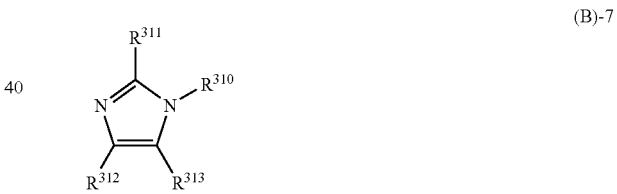

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are organic nitrogen-containing compounds having a benzimidazole structure and a polar functional group, represented by the general formula (B)-8.

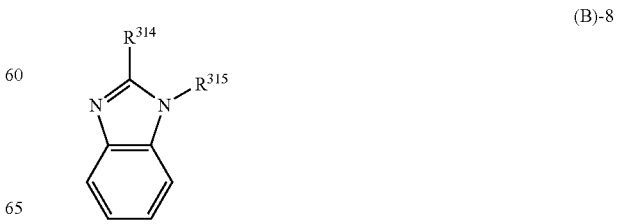

Herein, $R^{314}$ is a hydrogen atom, a straight, branched or cyclic alkyl group, aryl group or aralkyl group having 1 to 10 carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

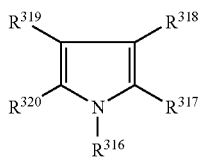
(B)-9

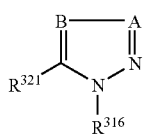
(B)-10

Herein, A is a nitrogen atom or $\equiv C-R^{322}$, B is a nitrogen atom or $\equiv C-R^{323}$, $R^{316}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic alkyl group or aryl group having 1 to 10 carbon atoms, or a pair of $R^{317}$ and $R^{318}$ and a pair of $R^{319}$ and $R^{320}$ may bond together to form a benzene, naphthalene or pyridine ring with the carbon atom to which they are attached; $R^{321}$ is a hydrogen atom, a straight, branched or cyclic alkyl group or aryl group having 1 to 10 carbon atoms; $R^{322}$ and $R^{323}$ each are a hydrogen atom, a straight, branched or cyclic alkyl group or aryl group having 1 to 10 carbon atoms, or a pair of $R^{321}$ and $R^{323}$, taken together, may form a benzene or naphthalene ring.

Also included are organic nitrogen-containing compounds of aromatic carboxylic ester structure having the general formulae (B)-11 to (B)-14.

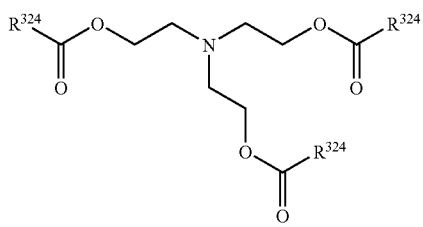
(B)-11

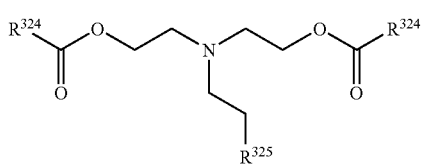
(B)-12

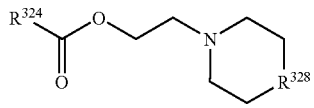
(B)-13

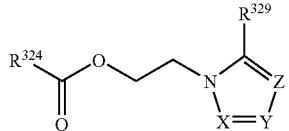
(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{236}$ is a $C_1$-$C_{10}$ alkyl group in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring.

Further included are organic nitrogen-containing compounds of 7-oxanorbornane-2-carboxylic ester structure having the general formula (B)-15.

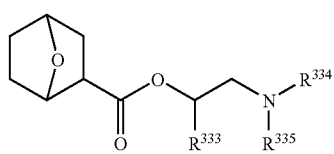
(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the entire base resin. Less than 0.001 part of the nitrogen-containing compound achieves no or little addition effect whereas more than 2 parts would result in too low a sensitivity.

The resist composition of the invention may include optional ingredients, for example, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

Optionally, a polymer may be added to the resist composition of the invention which will be locally distributed at the top of a coating and functions to adjust a hydrophilic/hydrophobic balance at the surface, to enhance water repellency, or to prevent low-molecular-weight components from flowing into or out of the coating when the coating comes in contact with water or similar liquids. The amount of functional polymer added is as used in resist compositions of this type as long as it does not compromise the objects of the invention, and is preferably up to 15 parts, and more preferably up to 10 parts by weight per 100 parts by weight of the base polymer.

Preferred examples of the functional polymer which will be localized at the coating top include polymers and copolymers comprising fluorinated units of one or more types, and copolymers comprising fluorinated units and other units. Illustrative examples of suitable fluorinated units and other units are shown below, but not limited thereto.

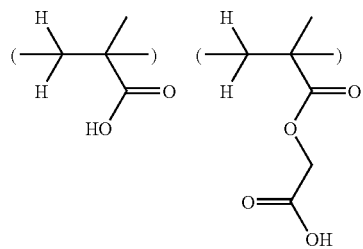

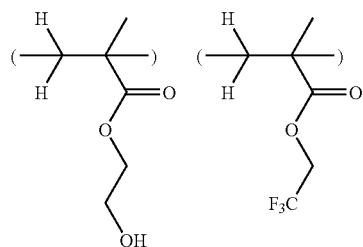

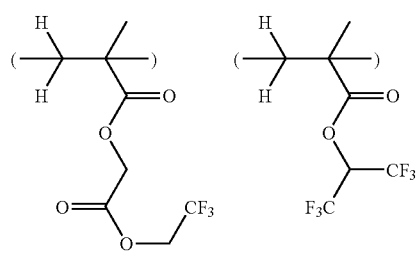

-continued

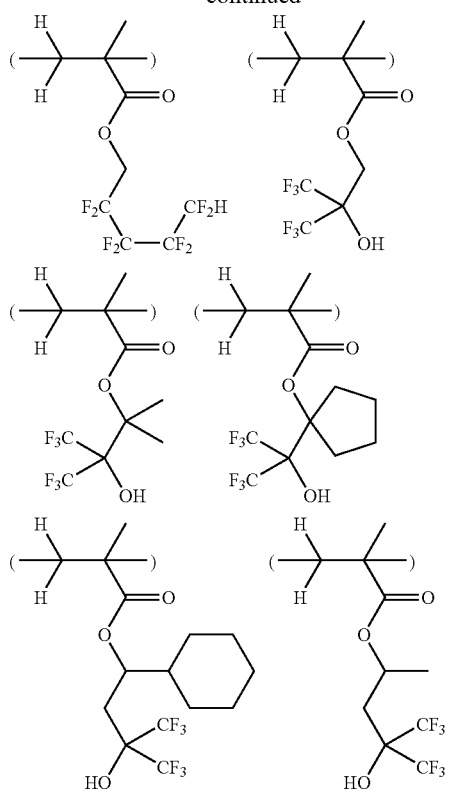

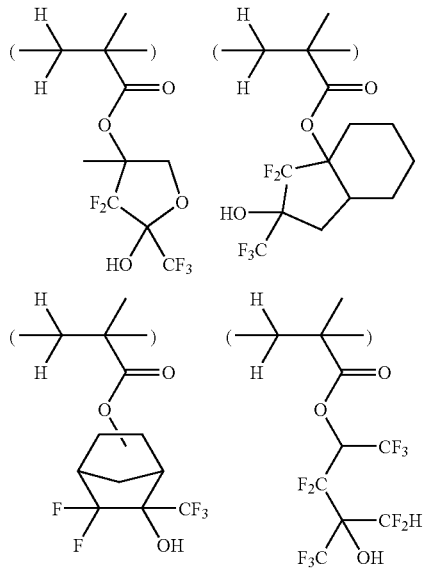

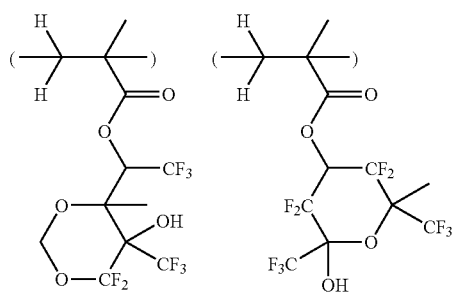

-continued
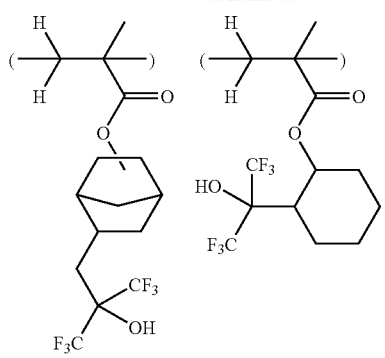
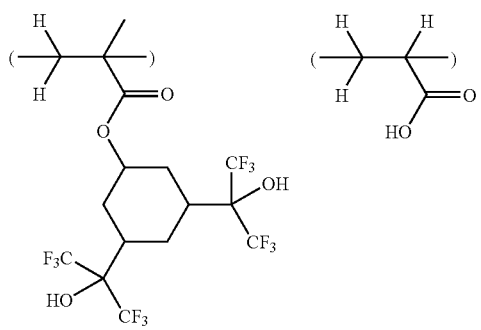
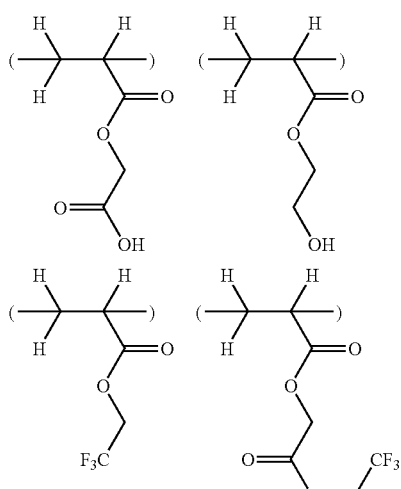
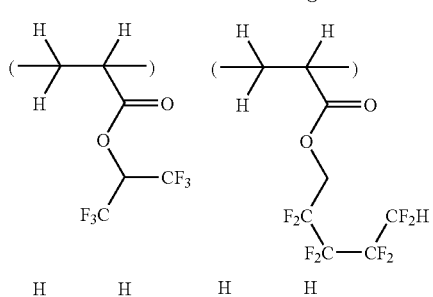
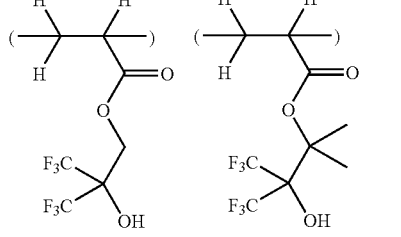
-continued
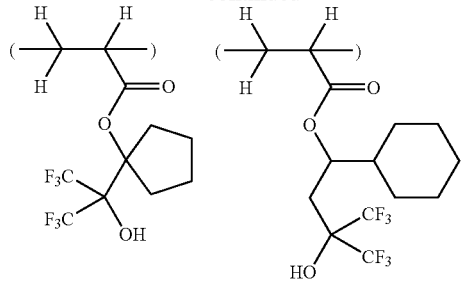
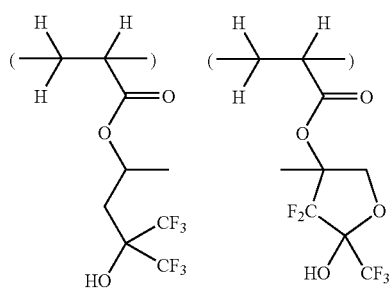
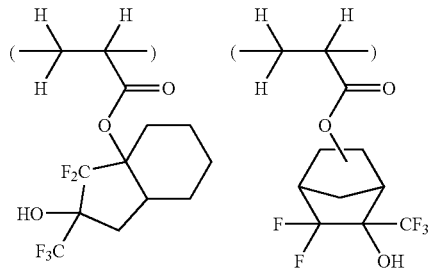
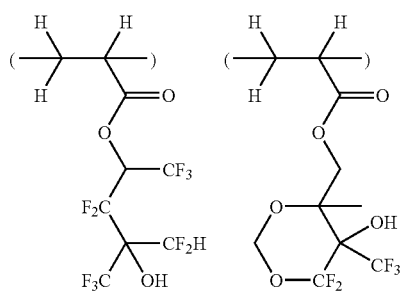
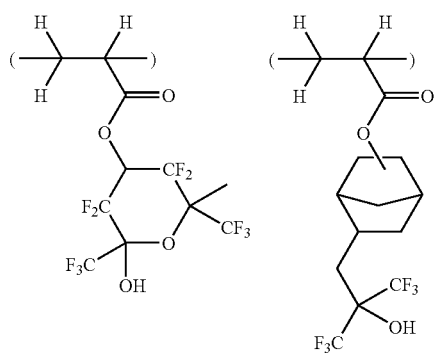

-continued

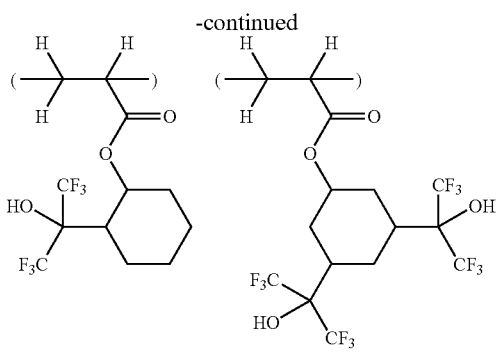

The functional polymer which will be localized at the coating top should preferably have a weight average molecular weight of 1,000 to 50,000, more preferably 2,000 to 20,000, as measured by GPC versus polystyrene standards. Outside the range, the polymer may have insufficient surface-modifying effect or cause development defects.

While the resist composition of the invention typically comprises a polymer, acid generator, organic solvent and organic nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

For pattern formation, the resist composition is first applied onto a substrate (on which an integrated circuit is to be formed, e.g., Si, $SiO_2$, SiN, SiON, TiN, WSi, BPSG, SOG, organic antireflective coating, Cr, CrO, CrON, MonSi, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 140° C. for 1 to 5 minutes. The resulting resist film is generally 0.01 to 2.0 µm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom. On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist and the organic film in this case may be an organic antireflective coating. After the photoresist film is formed, deionized water rinsing (or post-soaking) may be carried out for extracting the photoacid generator and the like from the film surface or washing away particles, or a protective film may be coated.

With a mask having a desired pattern placed above the resist film, the resist film is then exposed to actinic radiation such as UV, deep-UV, electron beams, x-rays, excimer laser light, γ-rays and synchrotron radiation. The exposure dose is preferably about 1 to 200 $mJ/cm^2$, more preferably about 10 to 100 $mJ/cm^2$. The film is further baked on a hot plate at 60 to 150° C. for 1 to 5 minutes, preferably 80 to 120° C. for 1 to 3 minutes (post-exposure baking=PEB). Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate. It is appreciated that the resist composition of the invention is suited for micro-patterning using such high-energy radiation as deep UV with a wavelength of 254 to 193 nm, vacuum UV with a wavelength of 157 nm, electron beams, soft x-rays, x-rays, excimer laser light, γ-rays and synchrotron radiation, and best suited for micro-patterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves prebaking a resist film and exposing the resist film to light through a projection lens, with deionized water or similar liquid interposed between the resist film and the projection lens. Since this allows projection lenses to be designed to a numerical aperture (NA) of 1.0 or higher, formation of finer patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking for preventing any dissolution from the resist and improving water slip on the film surface.

The resist protective coating used in the immersion lithography is preferably formed from a solution of a polymer having 1,1,1,3,3,3-hexafluoro-2-propanol residue which is insoluble in water, but dissolvable in an alkaline developer liquid, in a solvent selected from alcohols of at least 4 carbon atoms, ethers of 8 to 12 carbon atoms, and mixtures thereof.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

EXAMPLE

Synthesis Examples and Examples are given below by way of illustration and not by way of limitation. The abbreviation Mw is a weight average molecular weight as measured by GPC using polystyrene standards. PGMEA is propylene glycol monomethyl ether acetate. Me stands for methyl and Et for ethyl.

Synthesis Example 1

Fluorinated monomers within the scope of the invention were synthesized according to the following formulation.

Synthesis Example 1-1

Synthesis of Monomer 1

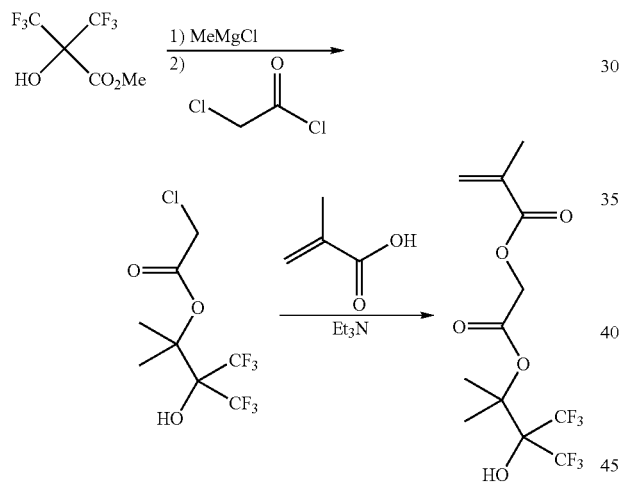

Synthesis Example 1-1-1

Synthesis of 4,4,4-trifluoro-3-hydroxy-2-methyl-3-(trifluoromethyl)butan-2-yl chloroacetate A flask was charged with 3,600 ml of a tetrahydrofuran solution of 1M methylmagnesium chloride, to which 226 g of methyl 2-hydroxy-3,3,3-trifluoro-2-trifluoromethylpropionate was added dropwise below 50° C. The contents were stirred at room temperature for one hour, after which 226 g of chloroacetic acid chloride was added dropwise, and 1000 g of 10% hydrochloric acid added. This was followed by ordinary work-up and recrystallization from n-heptane, obtaining 218 g of the target compound (yield 72%).

$^1$H-NMR (600 MHz in DMSO-$d_6$): δ=1.71 (6H, s), 4.26 (3H, d), 8.38 (1H, s) ppm $^{19}$F-NMR (565 MHz in DMSO-$d_6$, trifluoroacetic acid standard): δ=−70.0 (6F, s) ppm Synthesis Example 1-1-2

Synthesis of (4,4,4-trifluoro-3-hydroxy-2-methyl-3-trifluoromethylbutan-2-yloxycarbonyl)methyl methacrylate A mixture of 137 g of triethylamine and 100 g of dimethylformamide was added dropwise to a mixture of 129 g of methacrylic acid, 113 g of the chloroacetic ester obtained in [1-1-1], 22.0 g of sodium iodide and 400 g of dimethylformamide below 25° C. The reaction solution was stirred for 8 hours at the temperature. 300 g of 10% hydrochloric acid was added below 30° C. This was followed by ordinary work-up and vacuum distillation, obtaining 107 g of the target compound (yield 81%).

boiling point: 65-66° C./20 Pa

IR (thin film): ν=3322, 1770, 1729, 1637, 1421, 1384, 1326, 1228, 1193, 1145, 989, 941, 813 cm$^{-1}$ $^1$H-NMR (600 MHz in DMSO-$d_6$): δ=1.70 (6H, s), 1.88 (3H, s), 4.63 (2H, s), 5.76 (1H, t-like), 6.08 (1H, t-like), 8.40 (1H, s) ppm $^{19}$F-NMR (565 MHz in DMSO-$d_6$, trifluoroacetic acid standard): δ=−70.1 (6F, s) ppm Synthesis Example 1-2

Synthesis of Monomer 2

The procedure of Synthesis Example 1-1-2 was repeated aside from using acrylic acid instead of methacrylic acid. There was obtained (4,4,4-trifluoro-3-hydroxy-2-methyl-3-trifluoromethylbutan-2-yloxycarbonyl)methyl acrylate (two step yield 55%).

Synthesis Example 1-3

Synthesis of Monomer 3

The procedure of Synthesis Example 1-1-2 was repeated aside from using α-trifluoromethylacrylic acid instead of methacrylic acid. There was obtained (4,4,4-trifluoro-3-hydroxy-2-methyl-3-trifluoromethylbutan-2-yloxycarbonyl)-methyl α-trifluoromethylacrylate (two step yield 47%).

Synthesis Example 1-4

Synthesis of Monomer 4

The procedure of Synthesis Example 1-1-2 was repeated aside from using 5-norbornene-2-carboxylic acid instead of methacrylic acid. There was obtained (4,4,4-trifluoro-3-hydroxy-2-methyl-3-trifluoromethylbutan-2-yloxycarbonyl)-methyl 5-norbornene-2-carboxylate (two step yield 60%).

Synthesis Example 1-5

Synthesis of Monomer 5

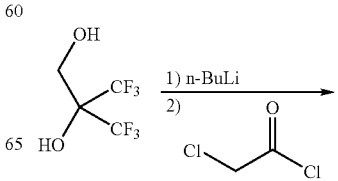

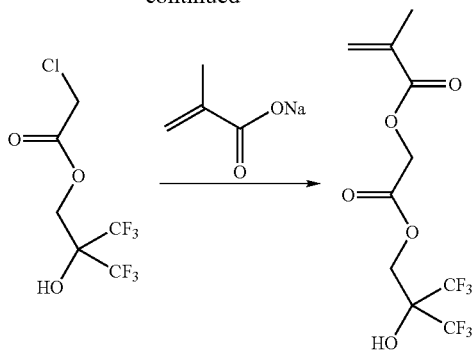

Synthesis Example 1-5-1

Synthesis of 3,3,3-trifluoro-2-hydroxy-2-trifluoromethylpropan-2-yl chloroacetate A flask was charged with 220 ml of a n-hexane solution of 1M n-butyllithium and 200 ml of tetrahydrofuran, to which a mixture of 19.8 g of 3,3,3-trifluoro-2-trifluoromethyl-1,2-propane diol and 20 ml of tetrahydrofuran was added dropwise below 10° C. The mixture was stirred for one hour below 10° C., after which 22.6 g of chloroacetic acid chloride was added dropwise and 200 ml of 10t hydrochloric acid added. This was followed by ordinary work-up, obtaining 22.2 g of the target compound (yield 81%).

Synthesis Example 1-5-2

Synthesis of (3,3,3-trifluoro-2-hydroxy-2-trifluoromethylpropan-2-yloxycarbonyl)methyl methacrylate A mixture of 13.8 g of the chloroacetic ester obtained in [1-5-1] and 20 g of dimethylformamide was added dropwise to a mixture of 10.8 g of sodium methacrylate, 1.5 g of sodium iodide, and 50 g of dimethylformamide below 30° C. The reaction solution was stirred for 8 hours at the temperature. 100 ml of 10% hydrochloric acid was added below 30° C. This was followed by ordinary work-up, obtaining 12.3 g of the target compound (yield 76%).

Synthesis Example 1-6

Synthesis of Monomer 6

The procedure of Synthesis Examples 1-1-1 and 1-1-2 was repeated aside from using isopropylmagnesium chloride instead of methylmagnesium chloride. There was obtained (5,5,5-trifluoro-4-hydroxy-2-methyl-4-trifluoromethylpentan-3-yloxycarbonyl)methyl methacrylate (two step yield 62%).

Synthesis Example 1-7

Synthesis of Monomer 7

The procedure of Synthesis Examples 1-1-1 and 1-1-2 was repeated aside from using isobutylmagnesium chloride instead of methylmagnesium chloride. There was obtained (1,1,1-trifluoro-2-hydroxy-5-methyl-2-trifluoromethylhexan-3-yloxycarbonyl)methyl methacrylate (two step yield 52%).

boiling point: 92-94° C./36 Pa

IR (thin film): ν=3407, 2966, 2875, 1762, 1733, 1637, 1423, 1390, 1301, 1214, 1153, 1081, 991, 948, 813 cm$^{-1}$ 3H-NMR (600 MHz in DMSO-$d_6$): δ=0.88 (6H, dd), 1.50 (1H, m), 1.60 (2H, m), 1.89 (3H, s), 4.75 (1H, d), 4.83 (1H, d), 5.40 (1H, m), 5.78 (1H, t-like), 6.10 (1H, t-like), 8.53 (1H, s) ppm $^{19}$F-NMR (565 MHz in DMSO-$d_6$, trifluoroacetic acid standard): δ=−74.4 (3F, m), -72.0 (3F, m) ppm

Synthesis Example 1-8

Synthesis of Monomer 8

The procedure of Synthesis Examples 1-1-1 and 1-1-2 was repeated aside from using cyclopentylmagnesium chloride instead of methylmagnesium chloride. There was obtained (1-cyclopentyl-3,3,3-trifluoro-2-hydroxy-2-trifluoromethylpropan-1-yloxycarbonyl)methyl methacrylate (two step yield 61%).

boiling point: 104-105° C./21 Pa

IR (thin film): ν=3411, 2962, 2875, 1762, 1731, 1637, 1456, 1421, 1388, 1274, 1216, 1149, 1058, 950, 813 cm$^{-1}$ $^1$H-NMR (600 MHz in DMSO-$d_6$): δ=1.28-1.62 (6H, m), 1.65 (1H, m), 1.82 (1H, m), 1.89 (3H, s), 2.27 (1H, m), 4.75 (1H, d), 4.83 (1H, d), 5.30 (1H, d), 5.77 (1H, s), 6.10 (1H, s), 8.43 (1H, s) ppm $^{19}$F-NMR (565 MHz in DMSO-$d_6$, trifluoroacetic acid standard): δ=−74.8 (3F, m), −72.1 (3F, m) ppm

Synthesis Example 1-9

Synthesis of Monomer 9

The procedure of Synthesis Examples 1-5-1 and 1-5-2 was repeated aside from using 4-chlorobutanoic acid chloride instead of chloroacetic acid chloride. There was obtained 3-(3,3,3-trifluoro-2-hydroxy-2-trifluoromethylpropan-2-yloxycarbonyl)propyl methacrylate (two step yield 56%).

Synthesis Example 1-10

Synthesis of Monomer 10

The procedure of Synthesis Examples 1-1-1 and 1-1-2 was repeated aside from using 4-chlorobutanoic acid chloride instead of chloroacetic acid chloride. There was obtained 3-(4,4,4-trifluoro-3-hydroxy-2-methyl-3-trifluoromethylbutan-2-yloxycarbonyl)propyl methacrylate (two step yield 52%).

Synthesis Example 1-11

Synthesis of Monomer 11

The procedure of Synthesis Examples 1-1-1 and 1-1-2 was repeated aside from using isopropylmagnesium chloride and 4-chlorobutanoic acid chloride instead of methylmagnesium chloride and chloroacetic acid chloride, respectively. There was obtained (5,5,5-trifluoro-4-hydroxy-2-methyl-4-trifluoro-methylpentan-3-yloxycarbonyl)propyl methacrylate (two step yield 54%).

The monomers prepared above are identified below.

Monomer 1
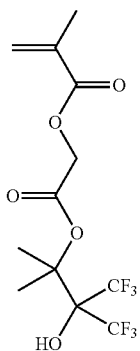
Monomer 5
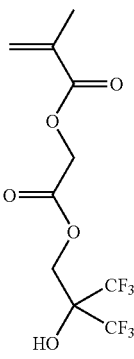
Monomer 2
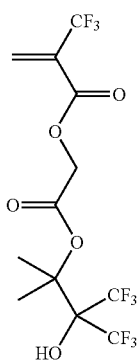
Monomer 6
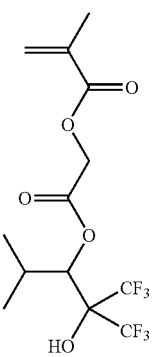
Monomer 3
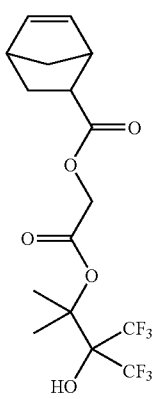
Monomer 7
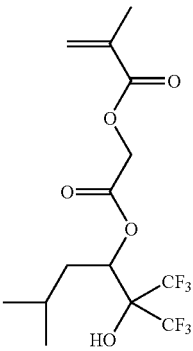
Monomer 4
Monomer 8
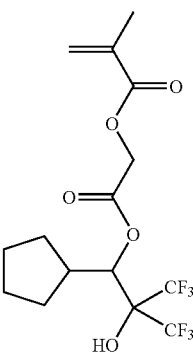

-continued

Monomer 9

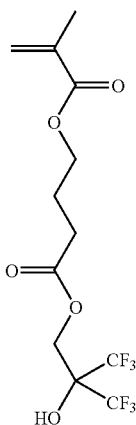

Monomer 10

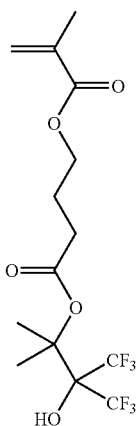

Monomer 11

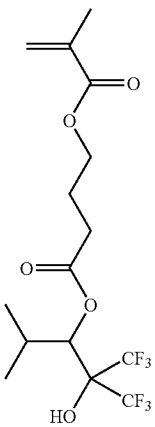

Synthesis Example 2

Polymers within the Scope of the Invention Were Synthesized According to the Following Formulation.

Synthesis Example 2-1

Synthesis of Polymer 1

In a nitrogen atmosphere, 28.1 g of Monomer 1, 21.9 g of 3-ethyl-3-exo-tetracyclo[$4.4.0.1^{2,5}.1^{7,10}$]dodecanyl methacrylate, 1048 mg of 2,2'-azobisisobutyronitrile, and 187 mg of 2-mercaptoethanol were dissolved in 87.5 g of PGMEA, and this solution was added dropwise over 4 hours to 29.2 g of PGMEA while stirring and heating at 80° C. The solution was stirred at 80° C. for a further 2 hours. The reaction solution was cooled to room temperature, and with vigorous stirring, added dropwise to 1,000 ml of n-hexane. The resulting solids were collected by filtration and dried in vacuum at 50° C. for 15 hours, obtaining 45.5 g (yield 91%) of a white powder solid designated Polymer 1. Polymer 1 had the compositional proportion and Mw shown in Table 1.

Polymer 1

[chemical structure of Polymer 1]

($c = 0.50$, $d = 0.50$, Mw = 7,400)

Synthesis Examples 2-2 to 2-19 and Comparative Synthesis

Examples 1-1 to 1-3

Synthesis of Polymers 2 to 22

Polymers 2 to 22 were synthesized by the same procedure as Synthesis Example 2-1 except that the type and proportion of monomers were changed, with their compositional proportion and Mw being shown in Table 1. The structure of the units is shown in Tables 2 to 5.

TABLE 1

| Resin | | Unit 1 (ratio) | Unit 2 (ratio) | Unit 3 (ratio) | Unit 4 (ratio) | Unit 5 (ratio) | Mw |
|---|---|---|---|---|---|---|---|
| Synthesis Example 2-1 | Polymer 1 | F-1M (0.50) | A-1M (0.50) | — | — | — | 7,400 |

TABLE 1-continued

|  | Resin | Unit 1 (ratio) | Unit 2 (ratio) | Unit 3 (ratio) | Unit 4 (ratio) | Unit 5 (ratio) | Mw |
|---|---|---|---|---|---|---|---|
| Synthesis Example 2-2 | Polymer 2 | F-2M (0.50) | A-1M (0.50) | — | — | — | 7,200 |
| Synthesis Example 2-3 | Polymer 3 | F-3M (0.50) | A-1M (0.50) | — | — | — | 7,500 |
| Synthesis Example 2-4 | Polymer 4 | F-4M (0.50) | A-1M (0.50) | — | — | — | 7,900 |
| Synthesis Example 2-5 | Polymer 5 | F-5M (0.50) | A-1M (0.50) | — | — | — | 7,800 |
| Synthesis Example 2-6 | Polymer 6 | F-1M (0.40) | A-1M (0.35) | B-1M (0.25) | — | — | 6,900 |
| Synthesis Example 2-7 | Polymer 7 | F-1M (0.35) | A-1M (0.40) | B-2M (0.25) | — | — | 7,000 |
| Synthesis Example 2-8 | Polymer 8 | F-1M (0.40) | A-1M (0.35) | B-3M (0.25) | — | — | 6,700 |
| Synthesis Example 2-9 | Polymer 9 | F-1M (0.10) | A-1M (0.25) | B-1M (0.25) | B-2M (0.40) | — | 6,800 |
| Synthesis Example 2-10 | Polymer 10 | F-1M (0.10) | A-2M (0.25) | B-1M (0.25) | B-2M (0.40) | — | 6,500 |
| Synthesis Example 2-11 | Polymer 11 | F-1M (0.10) | A-3M (0.25) | B-1M (0.25) | B-2M (0.40) | — | 6,600 |
| Synthesis Example 2-12 | Polymer 12 | F-1M (0.10) | A-4M (0.25) | B-1M (0.25) | B-2M (0.40) | — | 6,800 |
| Synthesis Example 2-13 | Polymer 13 | F-1M (0.10) | A-5M (0.25) | B-1M (0.25) | B-2M (0.40) | — | 6,400 |
| Synthesis Example 2-14 | Polymer 14 | F-1M (0.10) | A-6M (0.25) | B-1M (0.25) | B-2M (0.40) | — | 6,900 |
| Synthesis Example 2-15 | Polymer 15 | F-2M (0.10) | A-1M (0.25) | B-1M (0.25) | B-2M (0.40) | — | 7,400 |
| Synthesis Example 2-16 | Polymer 16 | F-3M (0.10) | A-1M (0.25) | B-1M (0.25) | B-2M (0.40) | — | 6,600 |
| Synthesis Example 2-17 | Polymer 17 | F-4M (0.10) | A-1M (0.25) | B-1M (0.25) | B-2M (0.40) | — | 7,100 |
| Synthesis Example 2-18 | Polymer 18 | F-5M (0.10) | A-1M (0.25) | B-1M (0.25) | B-2M (0.40) | — | 6,700 |
| Synthesis Example 2-19 | Polymer 19 | F-1M (0.10) | A-1M (0.25) | B-1M (0.25) | B-2M (0.30) | C-1M (0.10) | 6,800 |
| Comparative Synthesis Example 1-1 | Polymer 20 | — | A-1M (0.25) | B-1M (0.25) | B-2M (0.40) | C-2M (0.10) | 6,700 |
| Comparative Synthesis Example 1-2 | Polymer 21 | — | A-1M (0.25) | B-1M (0.25) | B-2M (0.40) | C-3M (0.10) | 7,000 |
| Comparative Synthesis Example 1-3 | Polymer 22 | — | A-1M (0.25) | B-1M (0.25) | B-2M (0.40) | C-4M (0.10) | 6,800 |

TABLE 2

| F-1M (R = CH$_3$) | F-2M (R = CH$_3$) | F-3M (R = CH$_3$) |
|---|---|---|
| 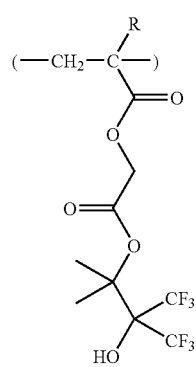 | 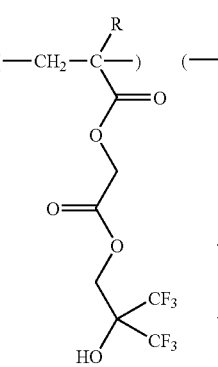 | 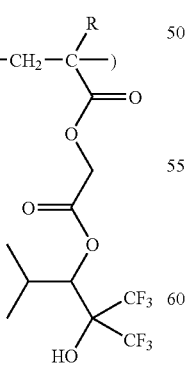 |

TABLE 2-continued

| R-4M (R = CH$_3$) | F-5M (R = CH$_3$) |
|---|---|
| 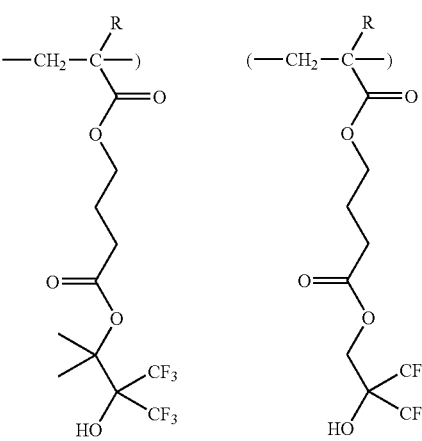 | |

TABLE 3

A-1M (R = CH₃), A-2M (R = CH₃), A-3M (R = CH₃), A-4M (R = CH₃), A-5M (R = CH₃), A-6M (R = CH₃)

TABLE 4

B-1M (R = CH₃), B-2M (R = CH₃), B-3M (R = CH₃)

TABLE 5

C-1M (R = CH₃), C-2M (R = CH₃), C-3M (R = CH₃), C-4M (R = CH₃)

Preparation of Resist Compositions

Examples 1-1 to 1-10 & Comparative Examples 1-1 and 1-2

Resist compositions were prepared by using inventive Polymers 9 to 18 or comparative Polymers 21 and 22 as the base resin, and dissolving the polymer, an acid generator (PAG), and a basic compound (Base) in a solvent mixture (PGMEA and CyHO) containing 0.01 wt % of surfactant KH-20 (Asahi Glass Co., Ltd.) in accordance with the recipe shown in Table 6. These compositions were each filtered through a Teflon® filter having a pore diameter 0.2 Mm, thereby giving inventive resist solutions R-01 to 10 and comparative resist solutions R-11 and 12.

TABLE 6

| | Resist | Resin (pbw) | PAG (pbw) | Base (pbw) | Solvent 1 (pbw) | Solvent 2 (pbw) |
|---|---|---|---|---|---|---|
| Example 1-1 | R-01 | Polymer 9 (80) | PAG-1 (4.4) | Base-1 (0.94) | PGMEA (560) | CyHO (240) |
| Example 1-2 | R-02 | Polymer 10 (80) | PAG-1 (4.4) | Base-1 (0.94) | PGMEA (560) | CyHO (240) |
| Example 1-3 | R-03 | Polymer 11 (80) | PAG-1 (4.4) | Base-1 (0.94) | PGMEA (560) | CyHO (240) |
| Example 1-4 | R-04 | Polymer 12 (80) | PAG-1 (4.4) | Base-1 (0.94) | PGMEA (560) | CyHO (240) |
| Example 1-5 | R-05 | Polymer 13 (80) | PAG-1 (4.4) | Base-1 (0.94) | PGMEA (560) | CyHO (240) |
| Example 1-6 | R-06 | Polymer 14 (80) | PAG-1 (4.4) | Base-1 (0.94) | PGMEA (560) | CyHO (240) |
| Example 1-7 | R-07 | Polymer 15 (80) | PAG-1 (4.4) | Base-1 (0.94) | PGMEA (560) | CyHO (240) |
| Example 1-8 | R-08 | Polymer 16 (80) | PAG-1 (4.4) | Base-1 (0.94) | PGMEA (560) | CyHO (240) |
| Example 1-9 | R-09 | Polymer 17 (80) | PAG-1 (4.4) | Base-1 (0.94) | PGMEA (560) | CyHO (240) |
| Example 1-10 | R-10 | Polymer 18 (80) | PAG-1 (4.4) | Base-1 (0.94) | PGMEA (560) | CyHO (240) |
| Comparative Example 1-1 | R-11 | Polymer 21 (80) | PAG-1 (4.4) | Base-1 (0.94) | PGMEA (560) | CyHO (240) |
| Comparative Example 1-2 | R-12 | Polymer 22 (80) | PAG-1 (4.4) | Base-1 (0.94) | PGMEA (560) | CyHO (240) |

The acid generator, base and solvent shown in Table 6 have the following meanings.
PAG-1: triphenylsulfonium 1,1,3,3,3-pentafluoro-2-cyclo-hexylcarboxypropanesulfonate
Base-1: tri(2-methoxymethoxyethyl)amine
PGMEA: 1-methoxyisopropyl acetate
CyHO: cyclohexanone Evaluation of Immersion Liquid Penetration Preventing Effect

Examples 2-1 to 2-10 & Comparative Examples 2-1 and 2-2

A resist composition comprising the inventive polymer as a base resin was evaluated for the effect of preventing immersion liquid (water) from penetrating into a resist film. Specifically, the resist composition (R-01 to 10) of Example 1 or comparative resist composition (R-11 and 12) was coated onto a silicon wafer pretreated with hexamethyl disilazane (HMDS) and baked at 100° C. for 60 seconds to form a resist film of 50 nm thick.

An inclination contact angle meter Drip Master 500 by Kyowa Interface Science Co., Ltd. was used. While the resist-coated wafer was kept horizontal, 50 microliters (µl) of deionized water was dripped thereon to form a droplet. While the wafer was gradually inclined, the angle (sliding angle) at which the droplet started sliding down was determined as well as receding contact angle. The results are shown in Table 7.

TABLE 7

| | Resist | Sliding angle (°) | Receding contact angle (°) |
|---|---|---|---|
| Example 2-1 | R-01 | 21 | 66 |
| Example 2-2 | R-02 | 22 | 63 |
| Example 2-3 | R-03 | 22 | 64 |
| Example 2-4 | R-04 | 21 | 65 |
| Example 2-5 | R-05 | 26 | 56 |
| Example 2-6 | R-06 | 26 | 57 |
| Example 2-7 | R-07 | 27 | 54 |
| Example 2-8 | R-08 | 21 | 66 |
| Example 2-9 | R-09 | 20 | 67 |
| Example 2-10 | R-10 | 28 | 55 |
| Comparative Example 2-1 | R-11 | 35 | 46 |
| Comparative Example 2-2 | R-12 | 28 | 54 |

As seen from Table 7, the resist compositions comprising the inventive polymers as the base resin have a smaller sliding angle and a larger receding contact angle, indicating that the resist films are effective for preventing penetration of immersion liquid (water). A smaller sliding angle also indicates an easier flow of water on the film, advantageously allowing for a higher scanning speed during scan exposure. A larger receding contact angle indicates that fewer liquid droplets are left during high-speed scan exposure.

Evaluation of Resist Composition

Examples 3-1 to 3-10 & Comparative Examples 3-1 and 3-2

Each of inventive resist compositions (R-01 to 10) and comparative resist compositions (R-11 and 12) was spin coated on a silicon wafer having an antireflective coating (ARC-29A, Nissan Chemical Co., Ltd.) of 78 nm thick and baked at 110° C. for 60 seconds, forming a resist film of 170 nm thick. The wafer was exposed by means of an ArF excimer laser stepper (Nikon Corp., NA 0.68), post-exposure baked (PEB) for 60 seconds, and puddle developed with a 2.38 wt % tetramethylammonium hydroxide aqueous solution for 30 seconds, forming a 1:1 line-and-space pattern. During the PEB, an optimum temperature for each resist composition was employed. The wafer as developed was observed under a top-down scanning electron microscope (SEM). The optimum exposure (Eop, mJ/cm$^2$) was defined as the exposure dose which provided a 1:1 resolution at the top and bottom of a 0.11-μm 1:1 line-and-space pattern. The maximum resolution of the resist was defined as the minimum line width (in increments of 0.01 μm) of the lines and spaces that separated at the optimum exposure, with smaller values indicating better resolution.

The evaluation results (Eop and maximum resolution) of the resist compositions are shown in Table 8.

TABLE 8

|  | Resist | PEB temp. | Eop | Maximum resolution |
|---|---|---|---|---|
| Example 3-1 | R-01 | 105° C. | 31.0 mJ/cm$^2$ | 0.09 μm |
| Example 3-2 | R-02 | 115° C. | 35.0 mJ/cm$^2$ | 0.09 μm |
| Example 3-3 | R-03 | 110° C. | 33.0 mJ/cm$^2$ | 0.09 μm |
| Example 3-4 | R-04 | 115° C. | 35.0 mJ/cm$^2$ | 0.10 μm |
| Example 3-5 | R-05 | 110° C. | 33.0 mJ/cm$^2$ | 0.09 μm |
| Example 3-6 | R-06 | 105° C. | 35.0 mJ/cm$^2$ | 0.09 μm |
| Example 3-7 | R-07 | 100° C. | 31.0 mJ/cm$^2$ | 0.09 μm |
| Example 3-8 | R-08 | 105° C. | 31.0 mJ/cm$^2$ | 0.09 μm |
| Example 3-9 | R-09 | 105° C. | 30.0 mJ/cm$^2$ | 0.09 μm |
| Example 3-10 | R-10 | 100° C. | 29.0 mJ/cm$^2$ | 0.10 μm |
| Comparative Example 3-1 | R-11 | 110° C. | 41.0 mJ/cm$^2$ | 0.11 μm |
| Comparative Example 3-2 | R-12 | 110° C. | 38.0 mJ/cm$^2$ | 0.10 μm |

It is evident from Table 8 that the resist compositions within the scope of the invention are improved in resolution and dissolution when processed by ArF excimer laser lithography.

All the aforementioned patent publications are incorporated herein by reference.

Japanese Patent Application No. 2007-196907 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units derived from a fluorinated monomer having the general formula (1):

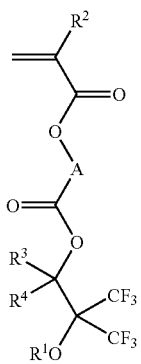

(1)

wherein $R^1$ is hydrogen or a straight, branched or cyclic monovalent hydrocarbon group of 1 to 20 carbon atoms in which any constituent —CH$_2$— moiety may be replaced by —O— or —C(=O)—, $R^2$ is hydrogen, fluorine, methyl or trifluoromethyl, $R^3$ and $R^4$ are each independently hydrogen or a straight, branched or cyclic monovalent hydrocarbon group of 1 to 8 carbon atoms, or $R^3$ and $R^4$ may bond together to form an aliphatic hydrocarbon ring with the carbon atom to which they are attached, and A is a straight, branched or cyclic divalent hydrocarbon group of 1 to 6 carbon atoms.

2. A polymer comprising recurring units derived from a fluorinated monomer having the general formula (2):

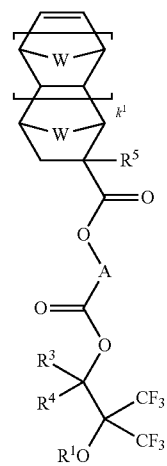

(2)

wherein $R^1$ is hydrogen or a straight, branched or cyclic monovalent hydrocarbon group of 1 to 20 carbon atoms in which any constituent —CH$_2$— moiety may be replaced by —O— or —C(=O)—, $R^3$ and $R^4$ are each independently hydrogen or a straight, branched or cyclic monovalent hydrocarbon group of 1 to 8 carbon atoms, or $R^3$ and $R^4$ may bond together to form an aliphatic hydrocarbon ring with the carbon atom to which they are attached, $R^5$ is hydrogen, fluorine, methyl or trifluoromethyl, A is a straight, branched or cyclic divalent hydrocarbon group of 1 to 6 carbon atoms, W is —CH$_2$— or —O—, and $k^1$ is 0 or 1.

3. A polymer comprising recurring units having any one of the general formulas (1a) to (1c):

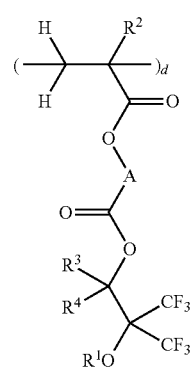

(1a)

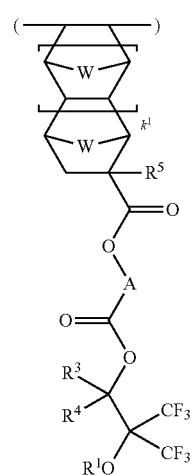

(1b)

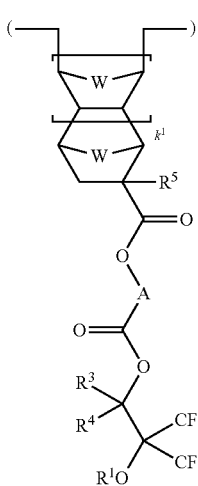

(1c)

wherein $R^1$ is hydrogen or a straight, branched or cyclic monovalent hydrocarbon group of 1 to 20 carbon atoms in which any constituent —$CH_2$— moiety may be replaced by —O— or —C(=O)—, $R^2$ is hydrogen, fluorine, methyl or trifluoromethyl, $R^3$ and $R^4$ are each independently hydrogen or a straight, branched or cyclic monovalent hydrocarbon group of 1 to 8 carbon atoms, or $R^3$ and $R^4$ may bond together to form an aliphatic hydrocarbon ring with the carbon atom to which they are attached, $R^5$ is hydrogen, fluorine, methyl or trifluoromethyl, A is a straight, branched or cyclic divalent hydrocarbon group of 1 to 6 carbon atoms, W is —$CH_2$— or —O—, and $k^1$ is 0 or 1.

4. The polymer of claims 1, 2, or 3, further comprising recurring units of at least one type selected from the general formulas (3) to (6):

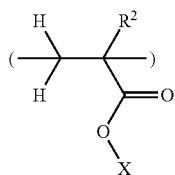

(3)

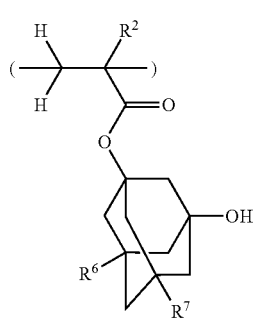

(4)

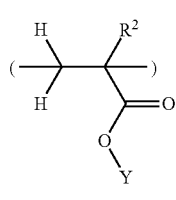

(5)

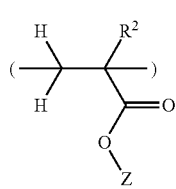

(6)

wherein $R^2$ is as defined above, $R^6$ and $R^7$ are each independently hydrogen or hydroxyl, X is an acid labile group, Y is a substituent group having a lactone structure, and Z is hydrogen, a fluoroalkyl group of 1 to 15 carbon atoms or a fluoroalcohol-containing substituent group of 1 to 15 carbon atoms.

5. A resist composition comprising the polymer of claims 1, 2, or 3 as a base resin.

* * * * *